United States Patent
Quirk

(10) Patent No.: US 12,428,655 B2
(45) Date of Patent: Sep. 30, 2025

(54) BIOREACTOR AND PROCESS FOR FORMING POLYHYDROXYBUTYRATE DIRECTLY FROM DEPOLYMERIZED POLYHYDROXYBUTYRATE

(71) Applicant: Kimberly-Clark Worldwide, Inc., Neenah, WI (US)

(72) Inventor: Stephen Quirk, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 18/558,863

(22) PCT Filed: May 27, 2022

(86) PCT No.: PCT/US2022/031284
§ 371 (c)(1),
(2) Date: Nov. 3, 2023

(87) PCT Pub. No.: WO2022/251591
PCT Pub. Date: Dec. 11, 2022

(65) Prior Publication Data
US 2024/0240212 A1    Jul. 18, 2024

Related U.S. Application Data

(60) Provisional application No. 63/194,445, filed on May 28, 2021.

(51) Int. Cl.
C12P 7/625 (2022.01)
C08J 11/10 (2006.01)
C12N 9/18 (2006.01)

(52) U.S. Cl.
CPC .............. *C12P 7/625* (2013.01); *C08J 11/105* (2013.01); *C08J 2367/04* (2013.01)

(58) Field of Classification Search
CPC ...... C12P 7/625; C08J 11/105; C08J 2367/04; B09B 83/60; C12N 9/18; C12Y 301/01075
See application file for complete search history.

(56) References Cited

U.S. PATENT DOCUMENTS

| | | | |
|---|---|---|---|
| 6,448,473 B1 | 9/2002 | Mitsky et al. | |
| 7,141,400 B2 | 11/2006 | Yu | |
| 7,361,807 B2 | 4/2008 | Zheng et al. | |
| 7,754,943 B2 | 7/2010 | Brumbley et al. | |
| 11,753,618 B2 | 9/2023 | Mitter et al. | |
| 2011/0159556 A1 | 6/2011 | Pieja et al. | |
| 2014/0303278 A1* | 10/2014 | Ferreira et al. | C12N 11/08 523/125 |
| 2017/0253713 A1 | 9/2017 | Ibrahim et al. | |

FOREIGN PATENT DOCUMENTS

| | | |
|---|---|---|
| CN | 104328062 A | 2/2015 |
| CN | 110904161 A | 3/2020 |
| EP | 0719342 B1 | 5/2005 |
| JP | 2002320499 A | 11/2002 |
| WO | WO2001068803 A2 | 9/2001 |
| WO | WO2008113190 A1 | 9/2008 |
| WO | WO2012078127 A1 | 6/2012 |
| WO | WO2012174451 A1 | 12/2012 |
| WO | WO2015097104 A1 | 7/2015 |
| WO | WO2016085396 A1 | 6/2016 |

OTHER PUBLICATIONS

Colombo, B. et al., Enhanced polyhydroxyalkanoate (PHA) production from the organic fraction of municipal solid waste by using mixed microbial culture, Biotechnology for biofuels, 2017, vol. 10, Article No. 201, https://doi.org/10.1186/s13068-017-0888-8.
PCT Search Report Corresponding to Application No. PCT/US2022/031284 on Sep. 20, 2022.
Kaihara et al., Enzymatic Transformation of Bacterial Polyhydroxyalkanoates into Repolymerizable Oligomers Directedtowards Chemical Recycling, Macromolecular Bioscience, vol. 5, Issue 7, 2005, Abstract Only, https://doi.org/10.1002/mabi.200500030.
Myung et al., Disassembly and reassembly of polyhydroxyalkanoates: Recycling through abioticdepolymerization and biotic repolymerization, Bioresource Technology, vol. 170, 2014, pp. 167-175, Abstract Only, https://doi.org/10.1016/j.biortech.2014.07.105.
Roohi et al., PHB (poly-β-hydroxybutyrate) and its enzymatic degradation, Polymers for Advanced Technologies, 2018, vol. 29, Issue 1, pp. 30-40, Abstract Only https://doi.org/10.1002/pat.4126.

* cited by examiner

*Primary Examiner* — Satyendra K Singh
(74) *Attorney, Agent, or Firm* — Dority & Manning, P.A.

(57) ABSTRACT

A bioreactor and process are disclosed for forming polyhydroxybutyrate directly from depolymerized polyhydroxybutyrate. In two bioreactor vessels, a microorganism product, such as one or more enzymes, are combined with the polyhydroxybutyrate-containing post-consumer product materials. The microorganism can naturally secrete the one or more enzymes or can be genetically modified to secrete the enzyme. The combination of enzymes is designed to facilitate a metabolic pathway that can depolymerize PHB, convert the resulting hydroxybutyrate to hydroxybutyryl-CoA, and in turn polymerize it into PHB. Namely, a solution for the recycling of polyhydroxybutyrate to hydroxybutyrate and back to polyhydroxybutyrate.

14 Claims, 6 Drawing Sheets
Specification includes a Sequence Listing.

SEQUENCE LISTING

<160> NUMBER OF SEQ ID NOS: 10

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met His His His His His His Gly Ser Glu Asn Leu Tyr Phe Gln Gly
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met His His His His His His Leu Glu Val Leu Phe Gln Gly Pro
1               5                   10                  15

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5

<210> SEQ ID NO 4
<211> LENGTH: 567
<212> TYPE: PRT
<213> ORGANISM: Pseudomonas sp.

<400> SEQUENCE: 4

Met Asp Asn Asn Ala His Thr Phe Asn Thr Phe Trp Ser Gly Gln Val
1               5                   10                  15

Pro Phe Ile Ala Ser Phe Ala Val Gln Gln Leu Arg Leu Trp Val Ser
                20                  25                  30

Thr Asn Pro Trp Phe Thr Gly Gln Glu Tyr Glu Lys Trp Phe Asp Leu
            35                  40                  45

Pro Arg Thr Thr Leu Glu Ser Leu Gln Ala Glu Tyr Gln Thr Gln Trp
        50                  55                  60

Gly Asp Leu Gly Gln Arg Leu Leu Thr Gly Gln Pro Phe Ser Phe Glu
65                  70                  75                  80

Asp Arg Arg Phe Ser Ser Gly Asn Trp Ser Thr Pro Leu Phe Gly Ser
                85                  90                  95

Leu Ala Ala Phe Tyr Leu Leu Asn Ala Gly Phe Leu Leu Lys Leu Leu
            100                 105                 110

Asp Lys Leu Pro Ile Lys Asp Lys Pro Arg Gln Arg Leu Leu Tyr
        115                 120                 125

Leu Val Glu Gln Ala Ile Ala Ala Gly Ala Pro Ser Asn Phe Leu Ala
    130                 135                 140

```
Ser Asn Pro Asp Ala Leu Gln Arg Val Val Asp Thr Gln Gly Gly Ser
145                 150                 155                 160

Leu Phe Thr Gly Leu Leu His Leu Ala Ser Asp Leu Gln Glu Gly Lys
            165                 170                 175

Met Arg Gln Cys Asp Ser Gly Ala Phe Lys Val Gly Val Asp Leu Ala
        180                 185                 190

Asn Thr Pro Gly Glu Val Val Phe Glu Asn Glu Leu Phe Gln Leu Ile
    195                 200                 205

Gln Tyr Tyr Pro Gln Ser Glu Thr Gln Tyr Arg Arg Pro Val Phe Ile
    210                 215                 220

Val Pro Pro Ser Ile Asn Lys Tyr Tyr Ile Leu Asp Leu Arg Pro Asp
225                 230                 235                 240

Asn Ser Met Val Arg His Leu Leu Gln Gln Gly His Pro Val Phe Leu
                245                 250                 255

Met Ser Trp Arg Asn Phe Asp Gln Ala His Ala Gly Thr Thr Trp Asp
            260                 265                 270

Asp Leu Ile Asp Thr Gly Ile Ile Lys Gly Leu Gln Val Thr Arg Glu
        275                 280                 285

Ile Ser Gly Glu Gln Arg Pro Asn Cys Val Gly Phe Cys Ile Gly Gly
    290                 295                 300

Thr Leu Leu Ser Ser Ala Leu Ala Val Leu Ala Ala Arg Gly Asp Lys
305                 310                 315                 320

Asp Ile Gly Ser Val Ser Leu Leu Thr Thr Phe Leu Asp Tyr Leu Asp
                325                 330                 335

Thr Gly Pro Ile Asp Ile Phe Val Asp Glu Gln Leu Val Ala Tyr Arg
            340                 345                 350

Glu Arg Thr Ile Gly Gly Gln Glu Gly Pro Ile Gly Leu Phe Lys Gly
        355                 360                 365

Glu Asp Met Gly Asn Thr Phe Ser Leu Leu Arg Pro Asn Asp Leu Trp
    370                 375                 380

Trp Asn Tyr Asn Val Asp Lys Tyr Leu Lys Gly Gln Lys Pro Ile Pro
385                 390                 395                 400

Leu Asp Leu Leu Phe Trp Asn Asn Asp Ser Thr Asn Leu Pro Gly Pro
                405                 410                 415

Met Tyr Cys Trp Tyr Leu Arg His Thr Tyr Leu Gln Asn Asp Leu Lys
            420                 425                 430

Ser Gly Glu Leu Asp Cys Cys Gly Val Lys Leu Asn Leu Arg Ala Ile
        435                 440                 445

Asp Ala Pro Ala Tyr Ile Leu Ala Thr His Asp His Ile Val Pro
    450                 455                 460

Trp Arg Ser Ala Tyr Ala Ser Thr Gln Leu Leu Ser Gly Thr Lys Arg
465                 470                 475                 480

Phe Val Leu Gly Ala Ser Gly His Ile Ala Gly Val Ile Asn Pro Pro
                485                 490                 495

Ala Arg Glu Lys Arg His Tyr Trp Thr Asn Asn Arg Val Ser Lys Asp
            500                 505                 510

Pro Asp Thr Trp Phe Met Asn Ala Gln Glu Gln Ala Gly Ser Trp Trp
        515                 520                 525

Asn Asp Trp Phe Val Trp Leu Ala Asp Gln Ala Gly Glu Arg Gln Pro
    530                 535                 540

Ser Val Ser His Ile Gly Asn Ala His Tyr Pro Ala Leu Glu Ser Ala
545                 550                 555                 560

Pro Gly Arg Tyr Val Met Gln
```

-continued

```
                565

<210> SEQ ID NO 5
<211> LENGTH: 261
<212> TYPE: PRT
<213> ORGANISM: Pseudomonas sp.

<400> SEQUENCE: 5

Met Glu Asp Gln Pro Lys Thr Val Leu Val Thr Gly Ser Thr Ser Gly
1               5                   10                  15

Ile Gly Leu Ala Ile Ala Lys Arg Phe Ala Glu Ala Gly Phe Leu Val
                20                  25                  30

Ala Val His Gly Val Glu Thr Ala Ala Glu Gly Ala Gln Ala Leu Glu
            35                  40                  45

Ala Val Ala Thr Val Ala Arg His Arg Pro Val Tyr Phe Ser Ala Asn
        50                  55                  60

Leu Ala His Tyr Asp Glu Ser Ala His Leu Pro Glu Lys Val Ile Ala
65                  70                  75                  80

Glu Phe Gly His Ile Asp Val Leu Val Asn Asn Ala Gly Ile Gln Lys
                85                  90                  95

Val Ala Pro Ile Asp Glu Phe Asp Phe Ala Asp Phe Ser Arg Ile Val
            100                 105                 110

Ala Ile Ser Leu Asp Ser Ala Phe His Thr Ile His Ala Ala Leu Pro
        115                 120                 125

Gly Met Lys Glu Arg Gly Trp Gly Arg Ile Val Asn Ile Ala Ser Ala
130                 135                 140

His Gly Leu Arg Ala Ser Pro Phe Lys Ala Pro Tyr Val Ala Thr Lys
145                 150                 155                 160

His Ala Val Val Gly Leu Thr Lys Ser Val Ala Leu Glu Val Ala Glu
                165                 170                 175

Gln Gly Ile Thr Cys Asn Ala Ile Cys Pro Gly Tyr Val Trp Thr Pro
            180                 185                 190

Leu Val Ala Ala Gln Val Ala Asp Gln Ala Arg Val His Gly Met Ser
        195                 200                 205

Glu Asp Asp Val Val Lys Lys Val Met Leu Ala Pro Gln Pro Thr Arg
    210                 215                 220

Arg Phe Val Gln Pro Glu Glu Val Ala Glu Met Ala Leu Tyr Leu Ala
225                 230                 235                 240

Gly Asp Met Ala Arg Ser Ile Thr Gly Thr Thr Ile Ser Ile Asp Gly
                245                 250                 255

Gly Trp Thr Ala Lys
            260

<210> SEQ ID NO 6
<211> LENGTH: 651
<212> TYPE: PRT
<213> ORGANISM: Pseudomonas sp.

<400> SEQUENCE: 6

Met Ser Glu Val Leu Trp Gln Pro Ser Ala Glu Arg Ile Gly Lys Thr
1               5                   10                  15

Arg Met Asp Ala Phe Arg Arg Phe Ser Asn Gln Arg Tyr Asn Leu Thr
                20                  25                  30

Leu Ala Asp Tyr Pro Ala Leu His Gln Trp Ser Ile Asp Gln Arg Glu
            35                  40                  45

Asp Phe Trp Gln Ala Ile Ile Asp Phe Phe Glu Ile Asn Phe His Gln
```

```
            50                  55                  60
Pro Pro Ser Thr Val Leu Arg Glu Gly Pro Gln Met Pro Ser Ala Glu
65                  70                  75                  80

Trp Phe Pro Gly Ala Thr Leu Asn Phe Ala Glu His Leu Leu Arg Arg
                85                  90                  95

Arg Asp Asp Ala Thr Ala Val Ile Ala Ile Ala Glu Asn Gly Gln Arg
            100                 105                 110

Glu Thr Leu Ser Tyr Cys Glu Leu Ala Glu His Val Ala Gly Leu Gln
            115                 120                 125

Lys Ser Leu Ser Ala Ala Gly Val Gly Leu Gly Asp Arg Val Ala Ala
            130                 135                 140

Cys Met Pro Asn Thr Trp Gln Thr Leu Val Gly Met Leu Ala Thr Thr
145                 150                 155                 160

Ser Leu Gly Ala Ile Trp Ser Cys Ser Ser Pro Asp Phe Gly Thr His
                165                 170                 175

Gly Val Val Asp Arg Phe Gly Gln Ile Glu Pro Lys Val Leu Ile Thr
            180                 185                 190

Cys Ala Gly Tyr Arg Tyr Ala Gly Lys Glu Phe Asp Gln Thr Thr Lys
            195                 200                 205

Val Asn Glu Ile Leu Glu Arg Leu Pro Ser Leu Gln Gln Leu Ile Ile
            210                 215                 220

Val Pro Tyr Ala Arg Pro Gln Ala Arg Val Asp Glu Tyr Lys Thr Gln
225                 230                 235                 240

Ala Asn Val Ala Leu Trp Asp Ser Phe Tyr Arg Pro Gly Gly Glu Pro
                245                 250                 255

Gly Phe Val Ala Val Pro Phe Ala His Pro Leu Tyr Ile Leu Tyr Ser
            260                 265                 270

Ser Gly Thr Thr Gly Val Pro Lys Cys Ile Ile His Ser Val Gly Gly
            275                 280                 285

Val Leu Leu Gln His Val Lys Glu His Gly Leu His Val Asp Leu Gly
            290                 295                 300

Pro Asp Asp Arg Leu Phe Tyr Tyr Thr Thr Cys Gly Trp Met Met Trp
305                 310                 315                 320

Asn Trp Leu Val Ser Ala Leu Ala Val Gly Ser Ser Val Val Leu Tyr
                325                 330                 335

Asp Gly Ser Pro Leu His Pro Gly Pro Gln Arg Leu Ile Asp Leu Ile
            340                 345                 350

Asp Ser Glu Ala Ile Ser Val Phe Gly Thr Ser Pro Lys Tyr Leu Ala
            355                 360                 365

Thr Leu Glu Ser Asn Glu Ile Gln Pro Arg Leu Ser His Asp Leu Ser
            370                 375                 380

Ser Leu Lys Ala Leu Leu Ser Thr Gly Ser Ala Leu Ser Pro Gln Ser
385                 390                 395                 400

Tyr Glu Tyr Val Tyr Arg Glu Ile Lys Ser Asp Leu Cys Leu Ser Ser
                405                 410                 415

Met Ser Gly Gly Thr Asp Ile Ile Ser Cys Phe Leu Ala Gly Asn Pro
            420                 425                 430

Val Leu Pro Val Arg Arg Gly Glu Met Gln Cys Lys Gly Leu Gly Met
            435                 440                 445

Ala Val Glu Val Trp Asn Glu Ala Gly Gln Pro Val Ile Gly Glu Lys
            450                 455                 460

Gly Glu Leu Val Cys Thr Arg His Phe Pro Ala Met Pro Ile Gly Leu
465                 470                 475                 480
```

```
Trp Asn Asp Pro Gln Gln Glu Lys Leu Arg Ala Ser Tyr Phe Ser Gln
                485                 490                 495

Phe Pro Gly Val Trp Ala Gln Gly Asp Tyr Ala Glu Gln Arg Pro Asn
            500                 505                 510

Gly Ser Trp Leu Ile His Gly Arg Ser Asp Ala Val Leu Asn Pro Gly
        515                 520                 525

Gly Val Arg Ile Gly Thr Ala Glu Ile Tyr Arg Gln Val Glu Lys Val
    530                 535                 540

His Gln Val Leu Asp Ser Val Ala Ile Gly Gln Gln Trp Gln Asp Asp
545                 550                 555                 560

Val Arg Val Val Leu Phe Val Arg Leu Arg Asp Gly Val Thr Leu Asp
                565                 570                 575

Asp Asn Leu Glu Gln Gln Ile Arg Gln Val Ile Arg Ala Asn Thr Thr
            580                 585                 590

Pro Arg His Val Pro Ala Lys Ile Val Ala Val Thr Asp Ile Pro Arg
        595                 600                 605

Thr Ile Ser Gly Lys Val Val Glu Leu Ala Val Arg Asn Val Val His
    610                 615                 620

Gly Gln Pro Val Lys Asn Thr Asp Ala Leu Ala Asn Pro Glu Ala Leu
625                 630                 635                 640

Glu Gln Phe Arg Asp Arg Pro Glu Leu Gln Arg
                645                 650

<210> SEQ ID NO 7
<211> LENGTH: 251
<212> TYPE: PRT
<213> ORGANISM: Pseudomonas sp.

<400> SEQUENCE: 7

Met Gly Thr Ala Ser Asn Ala Ala Arg Ile Ala Leu Val Thr Gly Gly
1               5                   10                  15

Met Gly Gly Ile Gly Thr Ala Ile Ser Gln Arg Leu His Arg Asp Gly
            20                  25                  30

Phe Thr Val Val Gly Cys Asn Pro Tyr Ser Ser Arg Lys Ala Ser
        35                  40                  45

Trp Ile Ala Thr Gln Leu Glu Ala Gly Phe His Phe His Cys Ile Asp
    50                  55                  60

Cys Asp Ile Thr Asp Trp Asp Ser Thr Arg Gln Ala Phe Asp Met Val
65                  70                  75                  80

His Glu Thr Val Gly Pro Ile Asp Val Leu Val Asn Asn Ala Gly Ile
                85                  90                  95

Thr Arg Asp Gly Thr Phe Arg Lys Met Ser Pro Glu Asn Trp Lys Ala
            100                 105                 110

Val Ile Asp Thr Asn Leu Thr Gly Leu Phe Asn Thr Thr Lys Gln Val
        115                 120                 125

Ile Glu Gly Met Leu Ala Lys Gly Trp Gly Arg Val Ile Asn Ile Ser
    130                 135                 140

Ser Ile Asn Gly Gln Arg Gly Gln Phe Gly Gln Thr Asn Tyr Ser Ala
145                 150                 155                 160

Ala Lys Ala Gly Ile His Gly Phe Ser Met Ala Leu Ala Arg Glu Val
                165                 170                 175

Ser Gly Lys Gly Val Thr Val Asn Thr Val Ser Pro Gly Tyr Ile Lys
            180                 185                 190

Thr Asp Met Thr Ala Ala Ile Arg Pro Asp Ile Leu Glu Asp Met Ile
```

```
            195                 200                 205
Thr Gly Ile Pro Val Gly Arg Leu Gly Gln Pro Glu Glu Ile Ala Ser
            210                 215                 220

Ile Val Ala Trp Leu Ala Ser Asp Gln Ser Ala Tyr Ala Thr Gly Ala
225                 230                 235                 240

Asp Phe Ser Val Asn Gly Gly Met Asn Met Gln
                245                 250
```

<210> SEQ ID NO 8
<211> LENGTH: 140
<212> TYPE: PRT
<213> ORGANISM: Pseudomonas sp.

<400> SEQUENCE: 8

```
Met Ala Lys Val Ile Leu Lys Lys Ile Asp Thr Gln Thr Asn Ala
1               5                   10                  15

Leu Ser Asp Val Lys Ile Tyr Ala Arg Lys Ile Trp Leu Ala Gly Leu
                20                  25                  30

Gly Ala Tyr Ala Lys Val Gly Ser Glu Gly Ser Glu Tyr Phe Lys Glu
            35                  40                  45

Leu Val Lys Thr Gly Gln His Val Glu Ser Lys Gly Lys Lys Val Val
        50                  55                  60

Asn Glu Gln Leu Asp Ala Ala Asn Ser Gln Ile Asp Tyr Val Lys Ser
65                  70                  75                  80

Asn Val Ser Ser Val Lys Gly Arg Val Glu Val Gln Leu Asp Lys Val
                85                  90                  95

Glu Lys Ala Phe Asp Ala Arg Val Ala Ser Ala Leu Asn Arg Ile Gly
            100                 105                 110

Ile Ala Ser Lys His Asp Val Glu Thr Leu Ser Ala Lys Leu Asp Glu
        115                 120                 125

Leu Thr Ala Leu Leu Glu Arg Val Ala Arg Lys His
    130                 135                 140
```

<210> SEQ ID NO 9
<211> LENGTH: 300
<212> TYPE: PRT
<213> ORGANISM: Unknown
<220> FEATURE:
<223> OTHER INFORMATION: Description of Unknown:
      Lihuaxuella thermophila sequence

<400> SEQUENCE: 9

```
Met Gly Gln Phe Ile Arg Asp Thr Ala Pro Asp Gly Arg Val Tyr Lys
1               5                   10                  15

Leu Tyr Ile Pro Ser Gly Tyr Asn Gly Ser Thr Pro Leu Pro Leu Val
                20                  25                  30

Val Met Leu His Gly Cys Thr Gln Asn Pro Asp Asp Phe Ala Ala Gly
            35                  40                  45

Thr Glu Met Asn Val Tyr Ala Glu Gln Asn Asn Phe Leu Val Ala Tyr
        50                  55                  60

Pro Glu Gln Pro Ser Ser Ala Asn Leu Asn Lys Cys Trp Asn Trp Phe
65                  70                  75                  80

Asp Ser Asn His Gln Ser Arg Gly Arg Gly Pro Ala Ser Ile Ala
                85                  90                  95

Gly Val Val Glu Asp Val Lys Arg Asn Tyr Ser Val Asp Ser Arg Arg
            100                 105                 110

Val Tyr Ala Ala Gly Leu Ser Ala Gly Gly Ala Met Ser Val Ile Met
```

Gly Ala Thr Tyr Pro Asp Val Phe Ala Ile Gly Val Gly Ser Gly
            130                 135                 140

Leu Glu Tyr Lys Ala Ala Thr Ser Met Thr Ser Ala Tyr Met Ala Met
145                 150                 155                 160

Ile Asn Gly Gly Pro Asp Pro Val Gln Gln Gly Asn Leu Ala Tyr Gln
                165                 170                 175

Ala Met Gly Ser His Ala Arg Val Val Pro Val Ile Val Phe His Gly
            180                 185                 190

Thr Ser Asp Tyr Thr Val Tyr Pro Val Asn Gly His Gln Val Ile Ser
            195                 200                 205

Gln Trp Ala Gln Thr Asn Asp Arg Ala Gly Asp Gly Val Asp Asn Asn
            210                 215                 220

His Ile Asp Asp Gln Ala Asp Val Thr Met Asn Gly Ser Val Pro Asn
225                 230                 235                 240

Gly Arg Thr Tyr Thr Arg Tyr Leu Tyr Lys Asp Gln Asn Gly Asn Val
                245                 250                 255

Val Met Glu Lys Ile Met Val Asn Gly Met Gly His Ala Trp Ser Gly
            260                 265                 270

Gly Ser Thr Ala Gly Thr Tyr Thr Asp Pro Ala Gly Pro Glu Ala Ser
            275                 280                 285

Ser Met Met Trp Ser Phe Phe Val Asn His Pro Lys
            290                 295                 300

<210> SEQ ID NO 10
<211> LENGTH: 332
<212> TYPE: PRT
<213> ORGANISM: Halomonas aquamarina

<400> SEQUENCE: 10

Met Glu Glu Glu Ala Pro Gly Leu Pro Ala Leu Gly Ala Ala Asn Asp
1               5                   10                  15

Gln Ala Ser Val Val Gly Val Ser Ser Gly Gly Tyr Met Ala Ser Gln
                20                  25                  30

Leu Ala Val Ala Trp Pro Glu Arg Phe Ser Gly Val Gly Met Leu Ala
            35                  40                  45

Ala Gly Pro Trp Gly Cys Ala Gln Gly Ala Leu Ser Leu Ala Leu Asn
        50                  55                  60

Gln Cys Met Met Thr Arg Arg Gly Leu Pro Ser Leu Asp Glu Leu Glu
65                  70                  75                  80

Gln Arg Arg Glu Arg Tyr Leu Ser Leu Asp Gln Val Gly Ser Gln Asp
                85                  90                  95

Ala Leu Ser Gln Leu Arg Ala Phe Val Trp His Gly Asp Ala Asp Glu
            100                 105                 110

Thr Val Ser Pro Ala Leu Gly Asp Leu Leu Ala Gln Gln Trp Gln Gly
            115                 120                 125

Trp Leu Glu Ser Pro Glu Gln Gln Leu Arg Tyr Val Gln Arg Ala Asn
            130                 135                 140

Thr Gly His Gly Trp Pro Val Ala Met Pro Lys Asp Ala Pro Ile Asp
145                 150                 155                 160

Pro Gln Ser Leu Gly Asp Cys Arg Asn Gly Gly Ser His Val Leu
                165                 170                 175

Ala Cys Gly Glu Asp Val Ala Gly Glu Met Met Ala Trp Leu Tyr Pro
            180                 185                 190

-continued

```
Glu Arg Glu Thr Asn Ala Ser Glu Gly Glu Leu Leu Ala Phe Asp Gln
    195                 200                 205
Ser Asp Phe Ala Ala Lys Gly Phe Ala Asp Thr Gly Tyr Val Phe Val
    210                 215                 220
Pro Glu Ala Cys Glu Ala Gly Gly Cys Pro Val Thr Val Ala Leu His
225                 230                 235                 240
Gly Cys Gln Met Asn Ala Glu Ala Ile Asp Asp Thr Phe Val Arg Tyr
                245                 250                 255
Ser Gly Leu Asn Arg Trp Ala Ala Glu His Gly Gln Val Val Leu Tyr
            260                 265                 270
Pro Gln Ala Glu Ser Ser Met Ala Asn Pro Gln Ala Cys Trp Asp Trp
        275                 280                 285
Trp Gly Phe Ala Glu Ser Thr Trp Gln Ile Asn Pro Leu His Asp Thr
    290                 295                 300
Arg Asp Gly Thr Gln Thr Gln Ala Leu Met Ala Met Leu Asp His Leu
305                 310                 315                 320
Gln Ser Ala Thr Ala Asn Lys Ala Ala Thr Ala Glu
                325                 330
```

BIOREACTOR AND PROCESS FOR FORMING POLYHYDROXYBUTYRATE DIRECTLY FROM DEPOLYMERIZED POLYHYDROXYBUTYRATE

RELATED APPLICATIONS

The present application is the national stage entry of International Patent Application No. PCT/US2022/031284 having a filing date of May 27, 2022, and Provisional Patent Application No. 63/194,445 having a filing date of May 28, 2021, which are incorporated herein in their entirety by reference thereto.

SEQUENCE LISTING

This application contains a Sequence Listing which has been submitted electronically in ASCII format and is hereby incorporated by reference in its entirety. Said ASCII copy, created on Oct. 30, 2023, is named KCX-2009-PCTUS_SL.txt and is 22,953 bytes in size.

BACKGROUND

Global production of petroleum-based plastics continues to increase every year. In recent years, for instance, over 300,000,000 metric tons of petroleum-based polymers have been produced. A significant portion of the above produced polymers are used to produce single-use products, such as plastic drinking bottles, straws, packaging, and absorbent articles, including wearable absorbent articles. Most of these plastic products are discarded and do not enter the recycle stream.

Particularly, absorbent articles, including personal care and child care garments, are currently made from predominantly petroleum-based plastics, such as films and nonwoven materials formed of polyethylene or polypropylene. Due to the nature of these articles, and the function they perform, it is difficult, if not impossible, to partially or completely recycle the polypropylene or polyethene materials used.

It has long been hoped that biodegradable polymers produced from renewable resources (hereinafter termed "biopolymers") would hold great promise in reducing the global accumulation of petroleum-based plastics in the environment. For example, significant research has been done on biologically derived polymers and on polymers that biodegrade in suitable environments. One such class of biopolymers are the polyhydroxyalkanoates (PHA). Much work has been accomplished on the PHA family, most notably the polyhydroxybutyrate (PHB) polymers including poly-3-hydroxybutyrate (P3HB), poly-4-hydroxybutyrate (P4HB), polyhydroxyvalerate (PHV), polyhydroxyhexanoate (PHH), polyhydroxyoctanoate (PHO) and their copolymers. Specifically, PHB shows promise in that the polymer is derived from natural sources, can be bio-degraded by several mechanisms, and is biocompatible with human tissues. Of particular advantage, PHA family biopolymers exhibit thermoplastic properties that are very similar to some petroleum-based polymers and thus represent viable replacements for petroleum-based polymers such as polypropylene and polyethylene.

Polyhydroxyalkanoates are synthesized using a variety of bacterial and archaea genera, including *Halobacillus, Bacillus, Salinobacter, Flavobacterium, Chromohalobacter, Halomonas, Marinobacter, Vibrio, Pseudomonas, Halococcus, Halorhabdus, Haladaptatus, Natrialba, Haloterrigena,* and *Halorussus*. The polyhydroxyalkanoate serves as an energy sink for these organisms. Production of polyhydroxyalkanoate polymers by the above microorganisms involves a three-step enzymatic mechanism that begins with acetyl coenzyme A. In forming PHB, the first step is catalysis of acetyl-CoA by PhaA (a β-ketothiolase) to form β-ketoacyl-CoA. This in turn is converted in a NADP-dependent reaction into R-3-hydroxyacyl-CoA by the PhaB enzyme (a β-ketoacyl-CoA reductase). The final step, catalyzed by PhaC (a PHB synthase), is the polymerization of R-3-hydroxyacyl-CoA into PHB. Said another way, the final step of the pathway involves the polymerization of hydroxyalkanoic acid monomers into a polyhydroxyalkanoate polymer via a polyhydroxyalkanoate polymerase. Bio-synthesized polyhydroxyalkanoates accumulate in the bacterial cell as large molecular weight granules and can account for from about 60% to about 90% of the cellular dry mass.

These same organisms express an extracellular and/or an intracellular PHB depolymerase (the gene phaZ) that degrades the polymer back to hydroxybutyrate (HB) and small PHB oligomers. The resulting HB is further degraded to provide a carbon and energy source for the microorganisms. From an industrial point of view HB is a dead-end in that it cannot be directly repolymerized by any known chemical process. Although it can be fully environmentally degraded, it would be economically and environmentally advantageous to be able to convert HB into a form that can readily be utilized to re-form PHB.

In nature, to retrieve the energy stored in the polymer, biodegradation is accomplished by a PHA depolymerase (PHADase). Unfortunately, natural PHADase are generally not conducive to industrial processes, e.g., post-consumer recycle processes, as an enzyme that is used for any bio-industrial process must have several characteristics that typical PHADase lacks. To be broadly useful, an enzyme for use in an industrial process should be thermodynamically and/or thermally stable in order to be long-lived in the process. An enzyme should also be as kinetically fast as possible so that a maximum amount of substrate is converted to product in a minimal amount of time. It must also be fully active in the environmental conditions of the industrial process. For example, in a process directed to processing of soiled PHB-containing personal care products (e.g. —diaper, feminine pad, incontinence garment, etc.) the enzyme must be able to function in an environment that is contaminated with feces, urine, menstrual fluid, etc. Ideally, the enzyme should be functional in a processing environment that is designed to neutralize contaminants that may be present in used consumer products (e.g., mesophilic bacteria).

If there was a process to re-form HB, it would make significant advances in waste disposal processes. Particularly, even though biopolymers are capable of biodegrading significantly faster than petroleum-based polymers, biopolymers can still remain in landfills or in the soil once discarded for significant periods of time. Thus, a need exists for a system and process for creating the decomposition and recycling of biopolymers, such as polyhydroxyalkanoates, once they enter the solid waste stream or to re-use the biopolymers to remove them from the waste stream completely.

A need exists for processes that can recycle bioplastics to recover PHA which can then be reused in reforming a bioplastic and/or biopolymer. It would be a further benefit if the recycled and reformed biopolymer is suitable for use in consumer products and industrial processes. Industrial processing materials and methods that can be used in processing biopolymers from post-consumer personal care products, for instance in a recycling process, would be of great benefit in the art. Specifically, it would be economically (and environmentally) advantageous to be able to convert HB into a form that can readily be utilized to re-form PHB. It would be a further benefit to provide a process using enzymes that converts a post-consumer product into recycled monomer, and polymerizes the recycled monomer into a biopolymer suitable for use in industrial processes. It would be an additional benefit to provide a reaction pathway for re-forming a biopolymer that bypasses any reactions involving acetyl-CoA allowing a pathway for the breakdown of polyhydroxybutyrate to hydroxybutyrate and then reforming polyhydroxybutyrate.

SUMMARY

In general, the present disclosure is directed to methods and systems for degradation, decontamination, and recycling of PHA polymers. Such PHA polymers can be components of post-consumer products, such as post-consumer personal care products, food industry products, and other recycled PHA containing articles, which may be contaminated. Currently, a significant portion of post-consumer products including, without limitation, packaging, straws, cups, bottles, shopping bags, eating utensils, trays, and personal care products such as personal care garments (e.g., diapers, child training pants, disposable swim pants, feminine hygiene products, adult incontinence products), tampon dispensers, medical supplies, etc., are made from petroleum-based polymers. Significant efforts are currently underway to incorporate biopolymers such as PHA into such products as well as improve and encourage the recycling of the biopolymers. The present disclosure is directed to improved methods and systems that can be used for simultaneous decontamination, biodegradation, and recycling of biopolymers in small or large settings.

In one aspect, disclosed are processes for recycling biopolymers in the polyhydroxyalkanoate family from a polyhydroxyalkanoate-containing post-consumer product. The process includes, within a first vessel, contacting a post-consumer product with an extremophilic microorganism suspension or an extremophilic depolymerase enzyme to supply a hydroxyalkanoate monomer, pumping the monomer containing solution through a filter to a second bioreactor vessel, and, within the second vessel, contacting the monomer with one or more enzymes, producing a recycled polyhydroxyalkanoate. In one aspect, the polyhydroxyalkanoate can be polyhydroxybutyrate. In one aspect, the extremophilic bacteria or the extremophilic depolymerase enzyme can be or be obtained from the following genera: *Halomonas, Lihuaxuella, Lysobacter, Alteromonas, Arthrobacter, Azospirillum, Empedobacter, Desulfovibrio, Halobacillus, Halobacteriovorax, Haloechinothrix, Halomarina, Halorussus, Haloterrigena, Isoptericola, Marinobacter, Methyloligella, Micromonospora, Natronococcus, Nocardiopsis, Paracoccus, Roseivivax, Saccharomonospora, Shewanella, Alicyclobacillus, Natranaerobius, Halobacteriaceae, Hyphomonas, Amycolatopsis, Georgenia, Acidothermus, Thermobifida*, or a combination thereof. For instance, in one aspect, the extremophilic bacteria or extremophilic depolymerase enzyme can be, or be obtained from, either *Lihuaxuella thermophila* or *Halomonas aquamarine*. In one aspect, the extremophilic bacteria can be either salt tolerant from about 0.5 molar to about 5 molar or temperature tolerant from about 40° C. to about 120° C., or a combination thereof. In one aspect, the extremophilic depolymerase enzyme can be produced by a genetically modified microorganism that has been genetically modified to secrete the extremophilic depolymerase enzyme. For instance, the extremophilic depolymerase enzyme can be produced by at least one type of a naturally occurring microorganism that naturally encodes the extremophilic depolymerase enzyme. In one aspect, the extremophilic microorganism or extremophilic enzyme can be or be purified from, organisms comprising: *Lysobacter aestuarii, Lysobacter antibioticus, Lysobacter bugurensis, Lysobacter capsica, Lysobacter enzymogenes, Lysobacter lacus, Lysobacter lycopersici, Lysobacter maris, Lysobacter niastensis, Lysobacter profundi, Lysobacter* sp., *Lysobacter* sp. A03, *Lysobacter* sp. cf310, *Lysobacter* sp. H21R20, *Lysobacter* sp. H21R4, *Lysobacter* sp. H23M41, *Lysobacter* sp. R19, *Lysobacter* sp. Root604, *Lysobacter* sp. Root690, *Lysobacter* sp. Root916, *Lysobacter* sp. Root983, *Lysobacter* sp. TY2-98, *Lysobacter spongiae, Lysobacter spongiicola, Lysobacter, Lysobacter alkalisoli, Lysobacter arseniciresistens, Lysobacter daejeonensis, Lysobacter dokdonensis, Lysobacter enzymogenes, Lysobacter enzymogenes, Lysobacter gilvus, Lysobacter gummosus, Lysobacter maris, Lysobacter oculi, Lysobacter panacisoli, Lysobacter penaei, Lysobacter prati, Lysobacter psychrotolerans, Lysobacter pythonis, Lysobacter ruishenii, Lysobacter segetis, Lysobacter silvestris, Lysobacter silvisoli, Lysobacter soli, Lysobacter* sp., *Lysobacter* sp. 17J7-1, *Lysobacter* sp. Alg18-2.2, *Lysobacter* sp. Cm-3-T8, *Lysobacter* sp. H23M47, *Lysobacter* sp. HDW10, *Lysobacter* sp. Il4, *Lysobacter* sp. N42, *Lysobacter* sp. OAE881, *Lysobacter* sp. Root494, *Lysobacter* sp. URHA0019, *Lysobacter* sp. WF-2, *Lysobacter* sp. yr284, *Lysobacter tabacisoli, Lysobacter telluris, Lysobacter tolerans, Lysobacter tolerans, Lysobacter xinjiangensis*, unclassified *Lysobacter, Aliivibrio finisterrensis, Aliivibrio fischeri, Aliivibrio sifiae, Aliivibrio* sp., *Aliivibrio* sp. 1S128, *Aliivibrio* sp. EL58, *Aliivibrio* sp. SR45-2, *Caballeronia arvi, Caballeronia calidae, Caballeronia hypogeia, Caballeronia insecticola, Caballeronia pedi, Caballeronia terrestris, Dokdonella koreensis, Dyella caseinilytica, Dyella choica, Dyella dinghuensis, Dyella flava, Dyella jiangningensis, Dyella kyungheensis, Dyella mobilis, Dyella monticola, Dyella nitratireducens, Dyella psychrodurans, Dyella soli, Dyella solisilvae, Dyella* sp. 7MK23, *Dyella* sp. ASV21, *Dyella* sp. ASV24, *Dyella* sp. C11, *Dyella* sp. C9, *Dyella* sp. DHC06, *Dyella* sp. EPa41, *Dyella* sp. G9, *Dyella* sp. M7H15-1, *Dyella* sp. M7H15-1, *Dyella* sp. OK004, *Dyella* sp. S184, *Dyella* sp. SG562, *Dyella* sp. SG609, *Dyella* sp. YR388, *Dyella tabacisoli, Fluoribacter bozemanae, Fluoribacter dumoffii* NY 23, *Fluoribacter gormanii, Microscilla marina, Pseudomonas aeruginosa, Pseudomonas thermotolerans, Pseudomonas mediterranea, Psychrobacter* sp., *Psychromonas* sp. MB-3u-54, *Psychromonas* sp. psych-6C06, *Psychromonas* sp. RZ22, *Psychromonas* sp. Urea-02u-13, *Rhodanobacter denitrificans, Rhodanobacter fulvus, Rhodanobacter glycinis, Rhodanobacter lindaniclasticus, Rhodanobacter panaciterrae, Rhodanobacter* sp. 7MK24, *Rhodanobacter* sp. A1T4, *Rhodanobacter* sp. B04, *Rhodanobacter* sp. B05, *Rhodanobacter* sp. C01, *Rhodanobacter* sp. C03, *Rhodanobacter* sp. C05, *Rhodanobacter* sp. C06, *Rhodanobacter* sp. DHB23, *Rhodanobacter* sp. DHG33, *Rhodanobacter* sp. L36, *Rhodanobacter* sp. MP1X3, *Rhodanobactersp.* OK091, *Rhodanobactersp.* OR444, *Rhodanobactersp.* PCA2, *Rhodanobactersp.* Root480, *Rhodanobactersp.* Root627, *Rhodanobactersp.* Root627, *Rhodanobacter* sp. SCN 67-45, *Rhodanobacter* sp. SCN 68-63, *Rhodanobacter* sp. Soil772, *Rhodanobactersp.* T12-5, *Rhodanobactersp.* TND4EH1, *Rhodanobactersp.* TND4FH1, *Rhodanobacter spathiphylli, Rhod-* anobacter thiooxydans, Stenotrophomonas chelatiphaga, Stenotrophomonas maltophilia, Stenotrophomonas panacihumi, Stenotrophomonas pavanii, Stenotrophomonas rhizophila, Stenotrophomonas sp. DDT-1, Stenotrophomonas sp. RIT309, Stenotrophomonas sp. SKA14, Vibrio aestuarianus, Vibrio antiquaries, Vibrio aquaticus, Vibrio tasmaniensis, Xanthomonadales bacterium, Xanthomonas albilineans, Xanthomonas arboricola, Xanthomonas axonopodis, Xanthomonas bromi, Xanthomonas campestris, Xanthomonas cannabis, Xanthomonas citri, Xanthomonas euvesicatoria, Xanthomonas fragariae, Xanthomonas hortorum, Xanthomonas hyacinthi, Xanthomonas oryzae, Xanthomonas phaseoli, Xanthomonas pisi, Xanthomonas sacchari, Xanthomonas sp. Leaf131, Xanthomonas sp. NCPPB 1128, Xanthomonas translucens, Xanthomonas vasicola, Xanthomonas vesicatoria, or a combination thereof. For instance, the extremophilic enzyme or extremophilic microorganism can be selected to be, or be purified from, either *Pseudomonas fluorescens* or *Agrobacterium tumifaciens*. In one aspect, the extremophilic enzyme can include about 12 or less Cystein residues. In one aspect, the extremophilic depolymerase enzyme has a molecular weight of about 3 kDa or less. In one aspect, the filter can be a molecular weight cutoff filter of about 3 kDa to about 30 kDa, optionally followed by an ion exchange bed. In one aspect, the pumping through the filter of the hydroxyalkanoate monomer to the second bioreactor vessel can occur when a measured optical density at 600 nm of the first bioreactor vessel contents is about less than 0.4 or when at least 40% of polyhydroxyalkanoate in the post-consumer product has been depolymerized to the monomer, or a combination thereof. In one aspect, the post-consumer product may contain urine, menses, feces, or a combination thereof comprises incontinence products, baby and childcare products, feminine care products, and family care products, or a combination thereof.

The present disclosure is also generally directed to a polyhydroxybutyrate produced from hydroxybutyrate liberated by the depolymerization of polyhydroxybutyrate in a multi-step enzymatic reaction. For instance, a polyhydroxybutyrate can be produced by, in a first bioreactor vessel, contacting polyhydroxybutyrate with a depolymerase to supply a hydroxybutyrate monomer, and, in a second bioreactor vessel, converting the hydroxybutyrate monomer to acetoacetate with a hydroxybutyrate dehydrogenase enzyme, converting acetoacetate to acetoacetate-CoA with an Acetoacetyl-CoA synthetase enzyme, reducing acetocetyl-CoA to hydroxybutyrl-CoA with an acetoacetyl-CoA reductase, and polymerizing hydroxybutyryl-CoA with a hydroxybutyrate polymerase to form polyhydroxybutyrate. In one aspect, the synthetase, the reductase, and the polymerase can be purified from bacteria in *Pseudomonas* or *Agrobacterium* genera. In one aspect, a *Pseudomonas* phasin can be further included in the second bioreactor vessel.

In one aspect, the present disclosure is also generally directed to a process for recycling polyhydroxybutyrate from a polyhydroxybutyrate-containing post-consumer product. For instance, a process can comprise, within a first bioreactor vessel, contacting a post-consumer product with a thermophilic or halophilic bacteria suspension, or thermophilic or halophilic depolymerase enzyme, to supply a hydroxybutyrate monomer, pumping the hydroxybutyrate monomer through a molecular weight cutoff filter, optionally followed by an ion exchange bed, to a second bioreactor vessel, and, within the second bioreactor vessel, contacting the hydroxybutyrate monomer with an enzyme and a cofactor feed, thereby producing a recycled polyhydroxybutyrate.

In one aspect, the post-consumer product further comprises contamination that can be controlled using a high salt concentration or a high temperature in the first bioreactor vessel. In one aspect, the cofactor feed comprises Coenzyme A, nicotinamide adenine dinucleotide, Nicotinamide adenine dinucleotide phosphate, Adenosine triphosphate, Adenosine monophosphate, pyrophosphate, or a combination thereof.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
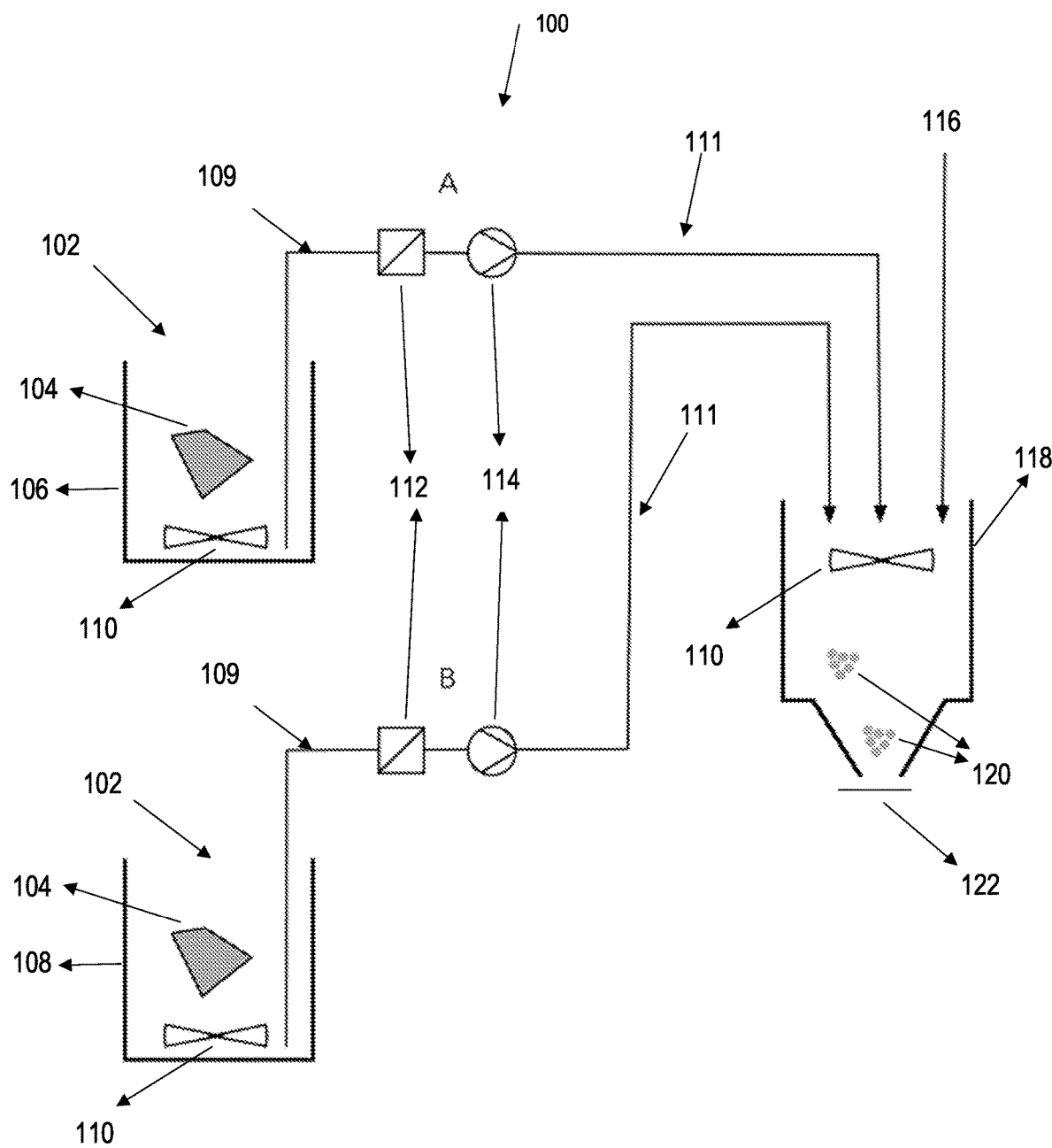
FIG. 1 is a design of one aspect of a bioreactor according to the present disclosure.

Repeat use of reference characters in the present specification and drawings is intended to represent the same or analogous features or elements of the present invention.

DETAILED DESCRIPTION

Definitions

The terms "about," "approximately," or "generally,", when used herein to modify a value, indicates that the value can be raised or lowered by 10%, such as 7.5%, such as 5%, such as 4%, such as 3%, such as 2%, or such as 1%, and remain within the disclosed aspect.

As used herein, the term "biodegradable" or "biodegradable polymer" generally refers to a material that degrades from the action of naturally occurring microorganisms, such as bacteria, fungi, archaea, and algae; environmental heat; moisture; or other environmental factors. The biodegradability of a material may be determined using ASTM Test Method 5338.92.

As used herein, the term "enzyme" generally refers to an enzyme that includes but is not limited to the following: native enzyme, purified enzyme, wildtype enzyme, modified enzyme, or combination thereof.

As used herein, the term "microorganism" includes bacteria, fungi, archaea, and algae, wildtype or modified, that expresses or produces one or more enzymes discussed herein As used herein, the terms "polyhydroxyalkanoate" or "hydroxyalkanoate" generally refer to a chemical family of biopolymers that includes but is not limited to the following members: the polyhydroxybutyrate (PHB) polymers including poly-3-hydroxybutyrate (P3HB), poly-4-hydroxybutyrate (P4HB), polyhydroxyvalerate (PHV), polyhydroxyhexanoate (PHH), polyhydroxyoctanoate (PHO), each of their monomers and copolymers.

DETAILED DESCRIPTION

It is to be understood by one of ordinary skill in the art that the present discussion is a description of exemplary aspects only and is not intended as limiting the broader aspects of the present disclosure.

In general, the present disclosure is directed to an enzyme-based cycle for the polymerization of hydroxybutyrate (HB) that allows recycled HB to be polymerized into industrially viable PHB. In addition, the present disclosure has found that such a cycle can be completed in a two vessel industrial-like bioreactor 100 process (see, e.g. FIG. 1, which will be discussed in greater detail below) that allows recycled PHB to be formed in a high yield and high purity manner. Such an enzyme-based approach allows HB, which is generally incapable of being reformed into PHB in nature, to be polymerized into PHB. Because HB cannot be directly repolymerized by any known chemical process, from an industrial point of view, HB is dead-end. However, surprisingly, the present disclosure provides for a pathway to convert HB into a form that can readily be utilized to re-form PHB by utilizing two additional enzymes: Hydroxybutyrate dehydrogenase (HBD) and Acetoacetyl-CoA synthetase (ACS) in a single, closed, two-vessel bioreactor. Particularly, the pathway disclosed herein bypasses any reactions involving acetyl-CoA and therefore represents a new non-naturally occurring pathway for a polyhydroxybutyrate to hydroxybutyrate and to polyhydroxybutyrate reaction.

Particularly, an enzymatic pathway laid out herein converts HB that is liberated from depolymerized PHB back to PHB. This creates a fully recycled use of the bioplastic in that a consumer product made from PHB can be broken down to HB and that HB can in turn be re-polymerized for the creation of a new (and fully recycled) PHB that can be used in a new consumer product. The approach described below, termed the "PHB Cycle" herein, notably, bypasses the first step in naturally occurring PHB biosynthesis and converts HB to PHB in four steps that can be conducted in a closed two-vessel system that will be discussed in greater detail.

Thus, the present disclosure has found that by utilizing a unique combination of enzymes, alone or in combination with extremophilic bacteria, a post-consumer product can be broken down into HB monomer units, which in-turn are re-polymerized, allowing a new PHB polymer and/or product to be formed from the post-consumer product. Further, the present disclosure has unexpectedly found that, unlike conventional teaching in the art, HB monomer units can be polymerized into PHB utilizing the PHB Cycle discussed herein. In addition, the present disclosure has found that the disclosed PHB cycle can be used in conjunction with one or more extremophilic bacteria, which allows a direct connection between the depolymerizing step or vessel and re-polymerizing step or vessel, avoiding inefficient and high cost cleaning steps.

The proposed PHB Cycle utilizes enzymes from carefully selected microorganisms that overcome previous deficiencies in natural cycles lacking the ability to form PHB from HB. The PHB Cycle is a circular enzymatic loop that begins with PHB and ends with newly polymerized PHB (see, e.g., FIG. 2), and includes carefully selected enzymes from multiple microorganisms (102, 116). Particularly, the microorganisms are selected based on factors that include but are not limited to the following: easy and fast to grow in high density, do not require special media, aerobic, kinetically fast, stable, tolerant to high salt environment, tolerant in a temperature environment, able to produce readily purifiable enzymes, lack an unusual isoelectric point, do not require heightened biosafety measures, do not comprise Cysteine residues in excess, overall non-esoteric, available for purchase commercially, or a combination thereof, which will be discussed in greater detail below.

However, while the enzymes have been discussed so far as being present in a solution, it should be understood that, in one aspect, the process may be performed utilizing one or more microorganisms that naturally express the discussed enzymes, or that have been modified to express the desired enzymes. Such a system may be referred to as a bacteria-based enzyme bioreactor instead of the enzyme based bioreactor discussed above. Of course, additional media, such as growth media, may be necessary if a bacteria-based bioreactor is utilized. Nonetheless, regardless of whether the bioreactor is bacteria based or enzyme based, the bioreactor may be run in batch, continuous flow, or perfusion mode.

Figure 2:
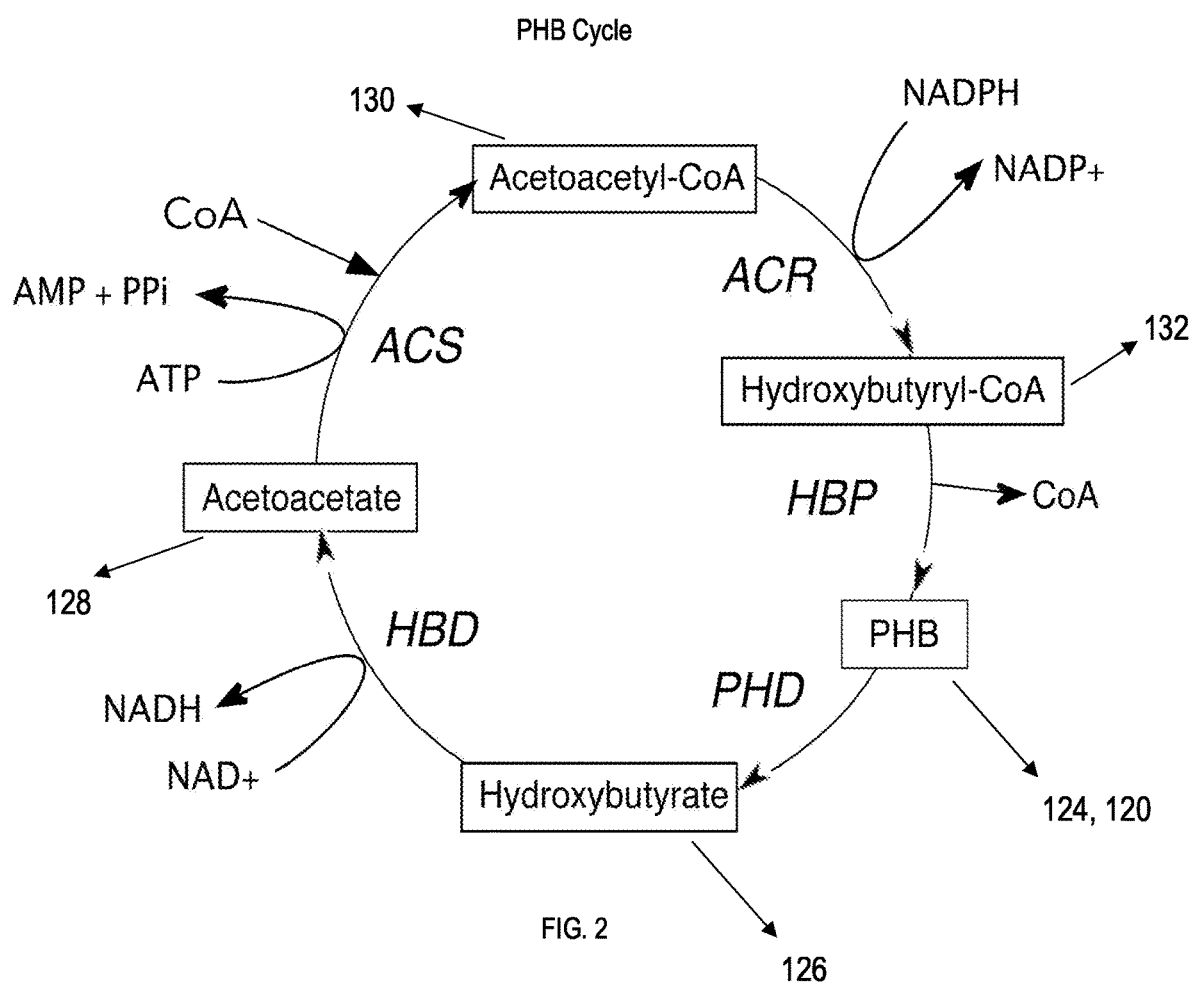
FIG. 2 is an illustration of one aspect of a proposed PBH cycle according to the present disclosure.
Figure 6:
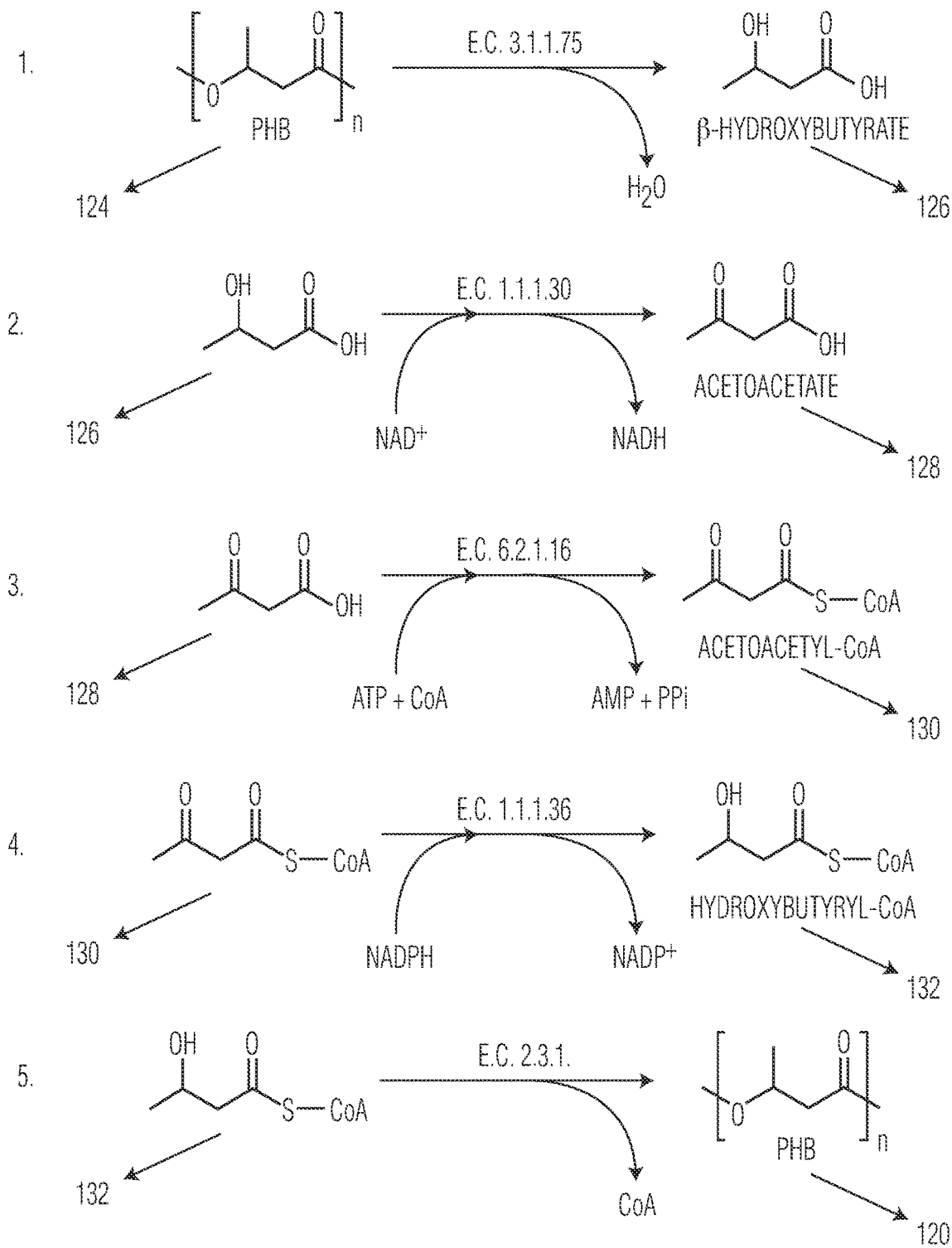
FIG. 6 is an illustration of one aspect of a five enzymatic steps in the full depolymerization—repolymerization of PHB/HB cycle according to the present disclosure.

The five enzymatic reactions that form the PHB cycle of FIG. 2 are provided in greater detail in FIG. 6, and include: ACA: Acetyl-CoA acetyltransferase, ACR: Acetoacetyl-CoA reductase, HBP: Hydroxybutyrate polymerase, PHD: Polyhydroxybutyrate depolymerase, HBD Hydroxybutyrate dehydrogenase, ACS: Acetoacetyl-CoA synthetase, CoA: Coenzyme A, NAD: Nicotinamide adenine dinucleotide, NADP: Nicotinamide adenine dinucleotide Phosphate, ATP: Adenosine triphosphate, AMP: Adenosine monophosphate, and PPi: pyrophosphate.

For instance, PHB depolymerase, which can be obtained from a variety of organisms is used for the first reaction (also referred to as the "first step" herein or reaction 1 in FIG. 6, and which is performed in the first vessel). In the second reaction (also referred to as the "second step" herein or reaction 2 in FIG. 6, which occurs in the second vessel), 3-hydroxybutyrate dehydrogenase is used to form acetoacetate 128 from the hydroxybutyrate 126. Acetoacetyl-CoA synthetase (ACS) performs the third reaction (also referred to as the "third step" herein or reaction 3 in FIG. 6, which occurs in the second vessel) in the PHB Cycle and provides the important step of committing intermediates to the subsequent repolymerization reactions, converting acetoacetate 128 to acetoacetyl-CoA 130. As shown in FIG. 6, the third reaction requires both coenzyme-A and ATP as cofactors, and occurs in the second vessel. Acetocetyl-CoA 130 is reduced in the fourth step (reaction 4 in FIG. 6, which occurs in the second vessel) of the PHB Cycle by acetoacetyl-CoA reductase, which forms the polymerizable molecule hydroxybutyryl-CoA 132. The fifth and last step (also referred to as the "final step" herein or reaction 5 in FIG. 6, which occurs in the second vessel) is the polymerization step of hydroxybutyryl-CoA 132 to PHB 120, which is catalyzed by a HB polymerase.

As discussed above, steps two through five of the PBH Cycle reactions are conducted in a second vessel 118 of a bioreactor system 100 that can be operated automatically or in a manual manner (FIG. 1). The bioreactor 100 is composed of two or more vessels (106/108, 118) that are connected in a closed manner, that separate key parts of the overall reaction and allow for filtration (112, 114) between such parts of the overall reaction.

For instance, as shown in FIG. 1, in one aspect, a post-consumer article or article to be recycled 104 containing one or more PHB polymers may be placed into a first vessel 106/108. It should be understood that the post-consumer article 104 may be in its original consumer form, or may be chopped or crushed prior to addition to the first vessel 106/108. Nonetheless, as discussed above, in one aspect, no pre-cleaning or sanitizing step is performed prior to addition of the post-consumer article 104 to the first vessel 106/108.

Regardless of the form of the post-consumer/recycled article 104, one or more enzyme feeds 102 containing a PHA depolymerase are introduced into the first vessel 106/108. Nonetheless, in one aspect, the microorganism derived enzyme feed includes an extremophilic microorganism or microorganism-derived extremophilic depolymerase enzyme. As used herein, and as will be discussed in greater detail below, extremophilic refers to a microorganism, or an enzyme obtained from an extremophilic microorganism, that tolerates one or more hostile environments, such as high salt, high temperature, elevated pressure, acidic, basic, or the like, specific examples of which will be set forth below.

Extremophilic microorganism-derived enzymes or the microorganisms themselves 102 along with carefully selected environmental conditions in the first bioreactor vessel (106, 108, e.g. conditions capable of sanitizing the post-consumer product, such as salt, heat or pressure, for example) allow for both the elimination or lessening of any fecal or other contamination in the post-consumer products 104 as well as simultaneous depolymerization of PHB 124 in a single vessel. Selection of, for example, depolymerase enzymes from thermophilic, halophilic, piezophilic, acidophilic, alkalophilic, or radiation resistant organisms or the microorganisms themselves (102) provides several ways of reducing the potential issues of fecal bacteria contamination or other contamination, such as, for instance, present in post-consumer diapers, during an industrial process. That is because fecal bacteria and other contaminants cannot live at elevated temperature, in extremely high salt concentrations, or at elevated pressures. Thus, the present disclosure allows for a unique and efficient pathway to simultaneously sterilize the post-consumer products 104 as well as depolymerize PHB 124. Of course, it should be understood that a halophilic vessel (e.g. 106) and a thermophilic vessel (e.g. 108) (or other extreme environment vessel) may be conducted simultaneously in order to increase the supply of HB to second vessel 118. However, as discussed above, and which will be discussed in greater detail below, both first vessels 106/108 may include an enzyme from the same or different extremophilic microorganism, such as halophilic, thermophilic, pressure resistant, or a combination thereof.

Furthermore, as shown in FIG. 1, the first vessel 106/108 and/or the second vessel 118 include an agitator 110. The agitator 110 may be run continuously through the reaction(s), or may be started and stopped intermittently as known in the art.

Nonetheless, the PHB depolymerase reaction is allowed to proceed until the desired portion of the PHB in the PHB containing post-consumer product 104 has been depolymerized. As will be discussed in greater detail in regards to the examples below, the reaction may be allowed to proceed until a decrease in PHB depolymerase is observed, optical density at 600 nm decreases, visual observance of polymer decreases, or a certain time period has elapsed.

Figure 3:
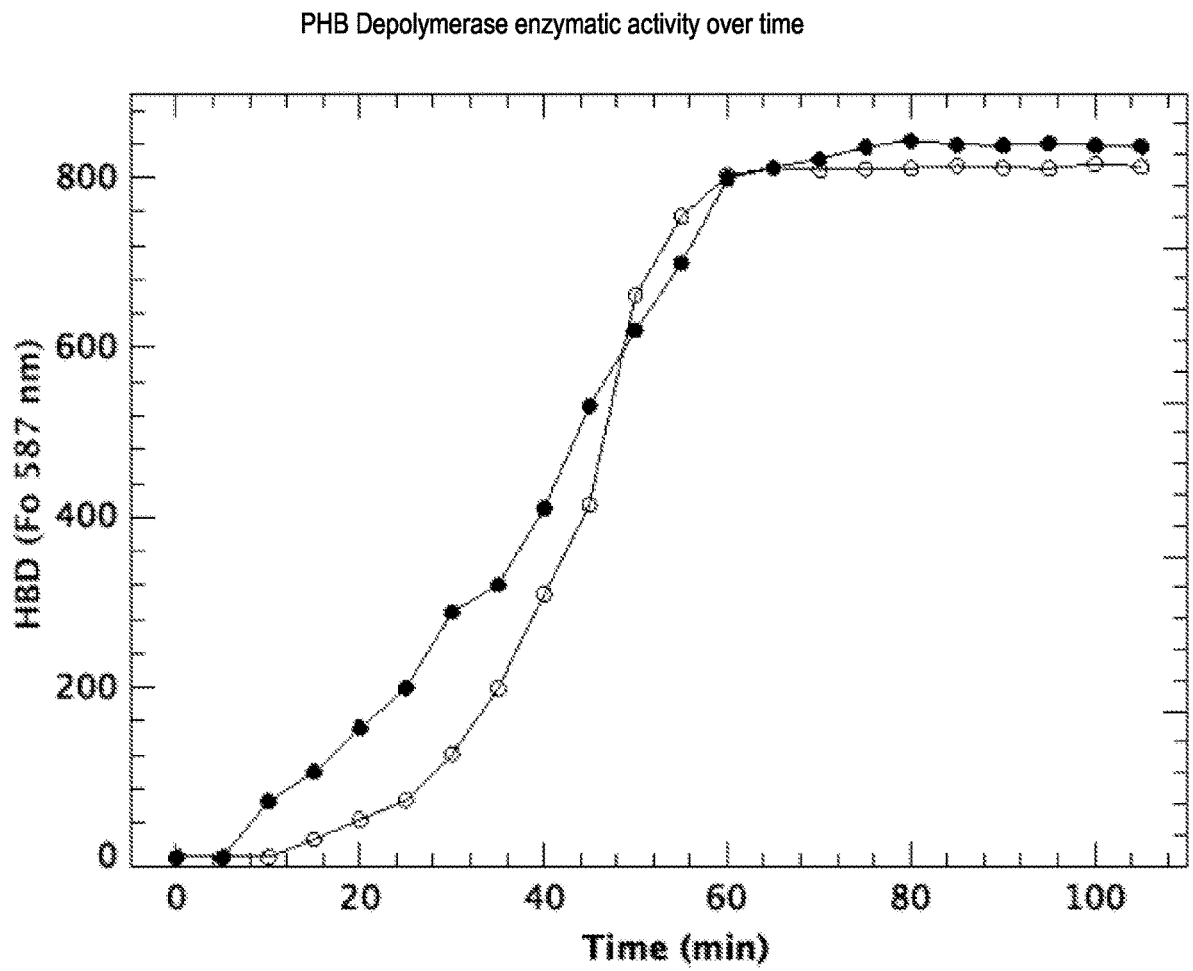
FIG. 3 is a graphical representation of PHB depolymerase enzymatic activity over time according to the Example.

For instance, in one aspect, the activity of PHB depolymerase may decrease as amounts of PHB present decrease. As shown in FIG. 3 and as will be discussed in greater detail below, the rate of HB production is a function of time and enzyme activity. Thus, in one aspect, the reaction in the first vessel 106/108 may be conducted until a plateau in enzyme activity is exhibited (e.g. about 60 minutes in FIG. 3).

Alternatively, one or more optical or visual measurements may be taken. For instance, PHB is insoluble in most solvents creating a high optical density at 600 nm, where HB is generally soluble due to its smaller molecular weight. Therefore, a decreased optical density, such as a density of about 0.9 or less, such as about 0.8 or less, such as about 0.7 or less, such as bout 0.6 or less, such as about 0.5 or less, such as about 0.4 or less, such as about 0.3 or less, such as about 0.2 or less, such as about 0.1 or less, as measured at 600 nm, indicates that the PHB has been depolymerized into HB monomer.

Alternatively, as the PHB is depolymerized, the visible pieces of PHB/post-consumer product can decrease. In such an aspect, the completion time may be based upon a visual analysis of the solution in the first vessel 106/108. Nonetheless, in a further aspect, a time to completion is determined based upon an amount of PHB and PHB depolymerase introduced into the first vessel 106/106 (or the time is calculated based upon a sample of optical density or PHB depolymerase activity), and the first vessel is allowed to react for an amount of time.

Regardless of the time selected, after the reaction in the first vessel 106/108 has been completed, the first reaction solution 109 containing waste plus depolymerized HB is allowed to proceed towards one or more filters 112/114. In one aspect, the filter 112 is a size exclusion filter (such as a molecular weight cutoff filter), having a size of about 5 kD or less, such as about 4.5 kD or less, such as about 4 kD or less, such as about 3.5 kD or less, such as about 3 kD or less, or any ranges or values therebetween. Particularly, any size filter may be used that is sized appropriately to retain any remaining pieces of the post-consumer product 104, any remaining PHB (that was not depolymerized), and any remaining PHB depolymerase. Most importantly, the filter should be selected to retain the PHB depolymerase, as allowing the PHB depolymerase through to the second vessel 118 would result in the depolymerization of re-formed PHB. Nonetheless, it is also advantageous that larger waste particles be retained at this point to allow the re-formed PHB 120 to be easily collected in the second vessel 118.

Furthermore, in one aspect, in addition to the size exclusion filter, it can be a further benefit to utilize an ion exchange filter 114 (such as a Dowex ion exchange bed), particularly when a halophilic enzyme is used (e.g. when the first vessel 106/106 utilizes a high salt concentration to destroy or neutralize or sanitize any impurities in the post-consumer product). The ion exchange filter 114 can remove salt from the first reaction solution 109 such that a neutral waste free HB monomer solution 111 enters the second vessel 118, so that extremophilic enzymes are not needed in the second vessel 118.

Subsequent steps of the PHB Cycle are conducted simultaneously in a second vessel 118 by supplying a co-factor feed 116 and the HB solution 111 that has passed through at least one filter (112, 114) to the second vessel 118. Particularly, as discussed above, reactions two through five of FIGS. 2 and 6 are allowed to proceed in the second vessel 118 until a precipitate of newly formed PHB 120 is collected. As will be discussed in greater detail below, the HBD, ACS, ACR, and HBP enzymes may be selected from one microorganism, or multiple microorganisms. Nonetheless, in order to have the reaction run smoothly in a single vessel, it is beneficial to select enzymes that are optimized at similar temperatures, pH, salt content, or a combination thereof. Thus, in one aspect, one or more of the enzymes of reactions 2 to 5 may be selected or purified from a single organism in order to increase the similarities in desired environment. However, it should be understood that, in one aspect, each enzyme is selected from different microorganisms. Furthermore, as discussed above, in one aspect, the microorganisms themselves can be used in the second vessel instead of enzymes therefrom.

Nonetheless, a co-factor feed 116 also provides the necessary co-factors for steps 2 through 5 of FIGS. 2 and 6 as discussed above, as well as any buffers, solvents, other additives, or combinations thereof. It should be understood that the co-factors and additives may be added simultaneously with the HB monomer solution 111, added continuously throughout the process, or may be added periodically when lagging or plateauing reactions are observed, or a combination thereof.

Nonetheless, the present disclosure has found that at least about 25%, such as about 27.5% or more, such as about 30% or more, such as about 32.5% or more, such as about 35% or more, such as about 37.5% or more, such as about 40% or more of PHB contained in a post-consumer/recycled product 104 is recovered as repolymerized PHB 120, based upon the weight of the PHB in the post-consumer/recycled product 104.

Notably, eliminating or reducing contaminants in the first bioreactor vessel reduces risk to process operators, reduce the risk of process equipment contamination, and subsequent reaction in the second vessel 118 can be carried out without additional sterilization procedures necessary for treatment of the pre-processed waste, the bioreactors, or the final post-processing reaction mixture. In addition, this allows the process steps in the second vessel 118 to be conducted in a neutral environment (e.g. room temperature and neutral salt), as decontamination is controlled in the first vessel 106/106 and one or more filters 112/114. This can simplify an overall treatment process and can reduce costs, for instance as the post-processing mixture (separated from HB monomer solution 111 at the filter step) can be safely discarded without additional processing. In addition, the present disclosure can also be used without the need to include additional antipathogenic agents, e.g., antibacterial processing aids, and as such can help to prevent overuse of such agents and associated development of antibiotic resistance in pathogens.

Post-consumer/recycled product 104 contaminants that include, without limitation, mesophilic pathogens, such as, without limitation, viruses, bacteria, fungi, and protozoans, can be rendered non-pathogenic by disclosed methods. As utilized herein, the terms "mesophile" and "mesophilic" refer to organisms that naturally exist in environmental conditions at which humans generally co-exist with the organism, including near human body temperature (e.g., from about 20° C. to about 45°), a saline content in water of from about 5 to about 18 parts per thousand (also referred to as mesohaline), about one atmosphere pressure (e.g., from about 20 kPa to about 110 kPa), and near neutral pH (e.g. from about pH 5 to about pH 8.5, also referred to as neutrophiles or neutrophilic). Typical bacterial pathogens encompassed herein can include those commonly found in human stool such as, and without limitation to, those of a genus *Streptococcus, Bifidobacterum, Lactobacillus, Staphylococcus, Clostridium, Enterobacteriaceae,* or *Bacteroides.*

Nonetheless, regardless of the decontamination needed, the present disclosure is generally directed to adding to a post-consumer material an extremophilic microorganism population or solution of extremophilic depolymerase enzyme (e.g. first vessel 106/108) that is particularly selected to secrete an enzyme for degrading and recycling the biopolymers. In one aspect, the microorganisms or enzymes therefrom, are encapsulated but remain viable and are released from the encapsulation once deposited in a post-consumer material depository or the first vessel. The process and system of the present disclosure is particularly directed to degrading and recycling used products containing polyhydroxyalkanoate polymers using microorganisms, such as bacteria or archaea, or enzymes therefrom that secrete an appropriate depolymerase enzyme.

Any suitable polyhydroxyalkanoate polymer can be degraded and recycled according to the present disclosure. The polyhydroxyalkanoate polymer can be a homopolymer or a copolymer. Polyhydroxyalkanoates, also known as "PHAs", are linear polyesters produced in nature by bacterial fermentation of sugar or lipids. More than 100 different monomers can be combined within this family to produce materials. One common type of polyhydroxyalkanoate polymer is Poly(3-hydroxybutyrate) (PHB).

Examples of monomer units that can be incorporated in polyhydroxyalkanoate polymers include 2-hydroxybutyrate, glycolic acid, 3-hydroxybutyrate, 3-hydroxypropionate, 3-hydroxyvalerate, 3-hydroxyhexanoate, 3-hydroxyheptanoate, 3-hydroxyoctanoate, 3-hydroxynonanoate, 3-hydroxydecanoate, 3-hydroxydodecanoate, 4-hydroxybutyrate, 4-hydroxyvalerate, 5-hydroxyvalerate, and 6-hydroxyhexanoate.

Examples of polyhydroxyalkanoate homopolymers include poly 3-hydroxyalkanoates (e.g., poly 3-hydroxypropionate (PHP), poly 3-hydroxybutyrate (PHB), poly 3-hydroxyvalerate (PHV), poly 3-hydroxyhexanoate (PHH), poly 3-hydroxyoctanoate (PHO), poly 3-hydroxydecanoate (PHD), and poly 3-hydroxy-5-phenylvalerate (PHPV)), poly 4-hydroxyalkanoates (e.g., poly 4-hydroxybutyrate (hereinafter referred to as PHB) and poly 4-hydroxyvalerate (hereinafter referred to as PHV)), or poly 5-hydroxyalkanoates (e.g., poly 5-hydroxyvalerate (hereinafter referred to as PHV)).

In certain aspects, the PHA can be a copolymer (containing two or more different monomer units) in which the different monomers are randomly distributed in the polymer chain. Examples of PHA copolymers include poly 3-hydroxybutyrate-co-3-hydroxypropionate (hereinafter referred to as PHB3HP), poly 3-hydroxybutyrate-co-4-hydroxybutyrate (hereinafter referred to as P3HB4HB), poly 3-hydroxybutyrate-co-4-hydroxyvalerate (hereinafter referred to as PHB4HV), poly 3-hydroxybutyrate-co-3-hydroxyvalerate (hereinafter referred to as PHB3HV), poly 3-hydroxybutyrate-co-3-hydroxyhexanoate (hereinafter referred to as PHB3HH) and poly 3-hydroxybutyrate-co-5-hydroxyvalerate (hereinafter referred to as PHB5HV).

The microorganism or collection of microorganisms that are selected for use in the present disclosure (either to be used directly, or to produce one or more of the enzymes discussed above) can be selected not only in order to secrete a particular enzyme according to the PHB cycle or a PHA depolymerase, but can also be selected based upon the environmental conditions in which the post-consumer product 104 waste material depository exists or which a bioreactor contains. For example, the post-consumer material depository can be contained in or a bioreactor may contain one of numerous environments that may be defined by a particular temperature range, salinity amounts, and the amount of oxygen contained in the soil, landfill, or bioreactor. In accordance with the present disclosure, the particular environmental variables can be matched to one or more microorganisms, such as bacteria and/or archaea, best suited for the particular environment. For example, microorganism may be selected based upon the salt or temperature tolerance of the microorganism selected, or by modifying a microorganism having the desired salt or temperature tolerance to express an appropriate depolymerase enzyme. For instance, it was surprisingly found that when a microorganism is selected based upon a specific salt tolerance, expression of an appropriate depolymerase enzyme, and thus, degradation of polyhydroxyalkanoate polymers can be further increased and/or slowed based upon the desired degradation rate. The microorganism selected, for instance, can be a microorganism that naturally produces the desired enzyme or can be a microorganism that has been genetically modified or cloned in order to express the desired depolymerase gene.

In one aspect, where the microorganism is selected to function in an environment that kills or inactivates other bacteria present in the post-consumer product 104, such as, for example, wearable articles that has been soiled with feces, menses, urine or otherwise, the microorganism may be selected to be tolerant of a concentration of a salt of about 0.5 M or greater, such as about 1M or greater, such as about 2M or greater, such as about 2.5M or greater, such as about 3 M or greater, such as about 3.5 M or greater, such as about 4 M or greater, such as about 4.5 M or greater, such as about 5 M or greater, such as about 5.5 M or greater, such as about 6 M or greater, such as about 6.5 M or greater, such as about 7 M or greater, or any ranges or values therebetween. For instance, in such an aspect, the post-consumer product 104 may be placed into a high salinity liquid, such as a container containing salt-water having a molar concentration of salt according to the above ranges, a commercial treatment facility, bioreactor, or a natural environment having a high degree of salinity. The high degree of salinity in conjunction with a microorganism having a tolerance for salt in that concentration may result in rapid degradation of the post-consumer product 104, and may also kill other bacteria, such as dangerous bacteria, in the article that are not tolerant of the high salinity. Thus, in one aspect, any one or more of the above salt concentrations may be used in first reaction vessel 106/108.

In another aspect, where the microorganism is selected to function in an environment that kills or inactivates other bacteria present in the post-consumer product 104, such as, for example, wearable articles that has been soiled with feces, menses, urine or otherwise, the microorganism may be selected to be tolerant to a temperature of about 40° C. or greater, such as about 50° C. or greater, such as about 60° C. or greater, such as about 70° C. or greater, such as about 80° C. or greater, such as about 90° C. or greater, such as about 100° C. or greater, such as about 110° C. or greater, such as about 120° C. or greater, such as about 130° C. or greater, such as about 150° C. or greater, or any ranges or values therebetween. For instance, in such an aspect, the post-consumer product 104 may be placed into a high temperature, such as a container containing water having a temperature according to the above ranges, a commercial treatment facility, bioreactor, or a natural environment having a high temperature. The high temperature in conjunction with a microorganism having a tolerance for temperature may result in rapid degradation of the post-consumer product 104, and may also kill other bacteria, such as dangerous bacteria, in the article that are not tolerant of the high temperature. Thus, in one aspect, any one or more of the above temperatures may be used in the first reaction vessel 106/108, alone or in combination with any one or more salt concentrations.

In one aspect, where the microorganism is selected to function in an environment that kills or inactivates other bacteria present in the post-consumer product 104, such as, for example, wearable articles that has been soiled with feces, menses, urine or otherwise, the microorganism may be selected to be tolerant to elevated pressure of about 0.5 MPa or greater, such as about 1 MPa or greater, such as about 5 MPa or greater, such as about 10 MPa or greater, such as about 15 MPa or greater, such as about 20 MPa or greater, such as about 30 MPa or greater, such as about 40 MPa or greater, such as about 50 MPa or greater, such as about 60 MPa or greater, such as about 70 MPa or greater, such as about 80 MPa or greater, such as about 90 MPa or greater, such as about 100 MPa or greater, such as about 150 MPa or greater, such as about 200 MPa or greater, such as about 250 MPa or greater, such as about 300 MPa or greater, such as about 350 MPa or greater, such as about 400 MPa or greater, such as about 450 MPa or greater, such as about 500 MPa or greater, such as about 550 MPa or greater, such as about 600 MPa or less, or any ranges or values therebetween. For instance, in such an aspect, the post-consumer product 104 may be placed into an elevated pressure environment, such as a commercial treatment facility, a bioreactor, or a natural environment having elevated pressure according to the above ranges. The elevated pressure in conjunction with a microorganism having a tolerance for elevated pressure may result in rapid degradation of the post-consumer product 104, and may also kill other bacteria, such as dangerous bacteria, in the article that are not tolerant to elevated pressure. Thus, in one aspect, any one or more of the above pressure ranges may be used in first reaction vessel 106/108.

In one aspect, the enzyme can include a PHB depolymerase (PHBDase) produced from a thermophile. For instance, the process can include contacting the post-consumer product 104 with a natural PHBDase from a thermophile and/or contacting the post-consumer care product with a thermophile that can produce a PHBDase. In one aspect, the process can include contacting a post-consumer care product with a polypeptide that includes a modified PHBDase that incorporates one or more single site mutations as compared to a wild-type PHBDase as produced from a thermophile.

Nonetheless, it should be understood that, in one aspect, a post-consumer product 104 according to the present disclosure may include more than one microorganism, and may therefore be configured to degrade in any concentration of salt or temperatures as discussed above. In one such aspect, the post-consumer product 104 may begin to degrade upon contact with a low-saline solution, such as a bodily fluid in one aspect, which may begin the degradation process, such as e.g. begin the process in the depository prior to addition to the first vessel. The post-consumer product 104 then be placed into a high-salinity environment which activates the high-salt tolerant microorganism and completing the degradation process started by the less-salt tolerant microorganism, such as, e.g. the first vessel. In one such aspect, the post-consumer product 104 may begin to degrade in low temperature, such as a bodily fluid in one aspect, which may begin the degradation process, such as e.g. in a depository prior to addition to the first vessel. The post-consumer product 104 then be placed into a high-temperature environment which activates the high-temperature tolerant microorganism and completing the degradation process started by the low-temperature tolerant microorganism, such as e.g. the first vessel.

In general, any suitable microorganism can be selected for use, or for production of the enzyme, in the present disclosure that secretes a metabolite or enzyme capable of degrading and recycling a biopolymer, particularly a polyhydroxyalkanoate polymer. For instance, the one or more microorganisms can be one or more bacteria or archaea that either expresses a native or an exogenous poly(hydroxybutyrate) depolymerase enzyme. In one particular aspect, the enzyme can be a poly[R-3-hydroxybutyrate] depolymerase enzyme. The following reaction, for instance, illustrates the enzymatic degradation of a polyhydroxybutyrate polymer by a poly[R-3-hydroxybutyrate]depolymerase.

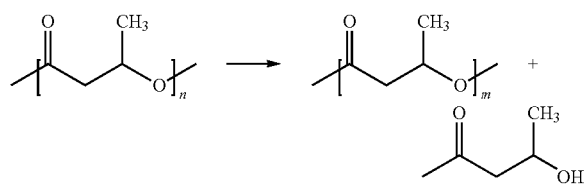

wherein m<<<n and represents small oligomers.

As stated above, in one aspect, the enzyme or metabolite that breaks down the polyhydroxyalkanoate polymer can be a naturally occurring bacteria (or enzyme therefrom) that naturally expresses the desired enzyme. For instance, in one aspect, the microorganism, or enzyme therefrom, incorporated into the product of the present disclosure is selected from a variety of bacterial genera including *Halomonas, Lihuaxuella, Lysobacter, Alteromonas, Arthrobacter, Azospirillum, Empedobacter, Desulfovibrio, Halobacillus, Halobacteriovorax, Haloechinothrix, Halomarina, Halorussus, Haloterrigena, Isoptericola, Marinobacter, Methyloligella, Micromonospora, Natronococcus, Nocardiopsis, Paracoccus, Roseivivax, Saccharomonospora, Shewanella, Alicyclobacillus, Natranaerobius, Halobacteriaceae, Hyphomonas, Amycolatopsis, Georgenia, Acidothermus,* and *Thermobifida.*

In one aspect, an extremophilic enzyme 102 for use in disclosed methods and processes can be a thermophilic enzyme that exhibits a $T_{opt}$ (that at which a maximum reaction rate can be achieved given suitable substrate) of about 40° C. or greater, about 50° C. or greater, about 60° C. or greater, about 70° C. or greater, about 80° C. or greater, or about 90° C. or greater in some aspects. Exemplary thermophiles (and thermophilic enzymes produced thereby) encompassed herein can include, without limitation, *Alicyclobacillus pomorum* (WP-084453829), *Amycolatopsis thermoflava* (WP-123687648), *Amycolatopsis thermalba* (WP-094002797), *Amycolatopsis rumani* (WP-116109633), *Azospirillum thermophilum* (WP-109324320), *Deinococcus actinosclerus* (WP-082689076), *Fervidobacterium gondwanense* (SHN54810), *Gandjariella thermophila* (WP-137812779), *Georgenia satyanarayanai* (WP-146237554), *Hyphomanas* sp. (HA037884), *Lihuaxuella thermophila* (WP-089972404), *Microbulbifer thermotolerans* (P-197462976), *Minwuia thermotolerans* (WP-206420073), *Rhodopseudomonas thermotolerans* (WP-114356866), *Rhodopseudomonas pentothenatexigens*, (WP-114356866), *Streptomyces thermovulgaris* (WP-067396676), *Thermanaeromonas toyohensis* (WP-084666479), *Thermoactinomyces* sp. CICC 10523 (WP-198056464), *Thermoactinomyces daqus* (WP-033100012), *Thermoactinospora* sp. (NUT44302), *Thermoactinospora rubra* (WP-084965756), *Thermobifida halotolerans* (WP-068692693), *Thermobifida fusca* (WP-011290529), *Thermobispora bispora* (WP-206206594), *Thermocatellispora tengchongensis*, (WP-185055796), *Thermochromatium tepidum* (WP-153975900), *Thermocrispum municipal* (WP-028851041), *Thermoflavimicrobium dichotomicum* (WP-093229000), *Thermogemmatispora carboxidivorans* (WP-081839208), *Thermogemmatispora aurantia* (WP-151728970), *Thermogemmatispora tikiterensis* (WP-11243376), *Thermogemmatispora onikobensis* (WP-084659191), *Thermoleophilaceae bacterium* (MBA2429278), *Thermomonospora echinospora* (WP-160147065), *Thermomonospora cellulosilytica* (WP-182704610), *Thermomonospora amylolytica* (WP-198679325), *Thermostaphylospora chromogena* (WP-093263254), *Thermus thermophilus* (WP-197735236), *Thermus aquaticus* (WP-053768217), *Thermus islandicus* (HE042284).

Temperature-based enzymes encompassed herein are not limited to high temperature thermophilic enzymes (and the microorganisms therefrom), and, in one aspect low temperature cryophilic enzymes (also referred to a psychrophilic enzymes, and the microorganisms therefrom) can be utilized. For instance, many bacterial strains will fail to multiply, but will still survive upon exposure to a temperature of about 10° C. for a period of time of about 6 hours. Thus, in some aspects, a cryophilic enzyme (and the microorganisms therefrom) capable of activity at a temperature of about 10° C. or less, for instance 7° C. or less, or from about −15° C. to about 10° C. in some aspects, can be utilized. Exemplary psychrophiles (and psychrophilic enzymes produced thereby) encompassed herein can include, without limitation, *Alteromonas oceani*(WP-123325050), *Alteromonas alba* (WP-105936495), *Alteromonas* sp. 38 (WP-201299304), *Alteromonas macleodii* (WP-156078157), *Alteromonas ponticola* (WP-169211550), *Alteromonas lipolytica* (WP-070178363), *Arthrobacter crystallopoietes* (WP-005270754), *Bosea psychrotolerans* (WP-181011807), *Glaciecola amylolytica* (WP-164472126), *Hyphomonas* sp. (HA037884), *Janthinobacterium psychrotolerans* (WP-065307954), *Massilia psychrophile* (WP-099914383), *Paraglaciecola psychrophile* (WP-007642709), *Polaromonas* sp. SP1 (WP-164483751), *Polaromonas* sp. AER18D-145 (WP-096697750), *Polaromonas* sp. CF318 (WP-007872516), *Polaromonas vacuolate* (WP-168920719), *Polaromonas naphthalenivorans* (WP-157040436), *Polaromonas* sp. JS666 (WP-011482994), *Polaromonas glacialis* (WP-084181426), *Polaromonas* sp. EUR3 1.2.1 (WP-197028649), *Polaromonas* sp. CG_9.2 (WP-196864241), *Polaromonas* sp. CG_9.11 (WP-196869863), *Polaromonas eurypsychrophila* (WP-188708524), *Polaromonas* sp. (MBC7445758), *Polaromonas jejuensis* (WP-068832216), *Polaromonas* sp. AET17H-212 (WP-096671180), *Polaromonas* sp. YR568 (WP-092127764), *Polaromonas* sp. C04 (WP-077562980), *Pseudorhodobacter psychrotolerans* (WP-08235149), *Psychrobacillus laslicapitis* (WP-142537823), *Psychrobacillus* sp. OK032 (WP-093265425), *Psychrobacillus* sp. OK028 (WP-093060398), *Psychrobacillus* sp. FJAT-21963 (WP-056833301), *Psychrobacter jeotgali* (WP-201583776), *Psychrobacter* sp. H8-1 (WP-201574875), *Psychrobacter* sp. Cmf 22.2 (WP-075103245), *Psychrobacter* sp. ENNN9_III (WP-058368887), *Psychrobacter* sp. P2G3 (WP-068327306), *Psychrobacter* sp. P11G5 (WP-068035467), *Psychrosphaera haliotis* (WP-155693683), *Shewanella psychrophile* (WP-077755816), *Simplicispira psychrophile* (WP-051603004), *Sphingobium psychrophilum* (WP-169570392), *Sphingomonas psychrolutea* (WP-188445826), *Clostridium homopropionicum* (WP-074782965), *Clostridium* sp. DL-VIII (WP- 009169886), *Clostridium clostridioforme* CAG:132 (CDB63357), *Zunongwangia atlantica* 22II14-10F7 (ORL47196).

Extremophilic enzymes 102 produced by halophiles can be utilized in some aspects. For instance, halophilic enzymes that exhibit activity at a salinity of about 1 M or greater, about 2 M or greater in some aspects, can be utilized. Exemplary halophiles (and halophilic enzymes produced thereby) encompassed herein can include, without limitation, *Alteromonas halophila* (WP-189403400), *Arthrobacter crystallopoietes* (WP-005270754), *Arthrobacter* sp. NEB 688 (WP-173027059), *Azospirillum halopraeferens* (WP-029007775), *Empedobacter halcabium* (TXE30443), *Desulfovibrio sulfodismutans* (NDY59052), *Halobacillus hunanensis* (WP-139377117), *Halobacillus ihumii* (WP-16352794), *Halobacteriovorax marinus* (WP-157868258), *Haloechinothrix halophila* (WP-051400222), *Halomarina oriensis* (WP-158204529), *Halomonas cerina* (WP-183325502), *Halomonas korlensis* (WP-089794761), *Halomonas* sp. PR-M31 (WP-048308188), *Halomonas aquamarine* (WP-089674669), *Halomonas zhanjiangensis* (WP-040460201), *Halomonas aestuarii* (WP-071946866), *Halomonas endophytica* (WP-102654199), *Halomonas heilongjiangensis* (WP-102629242), *Halomonas campaniensis* (WP-088701082), *Halomonas alkaliphile* (WP-038486873), *Halomonas* sp. ALS9 (WP-064233856), *Halomonas* sp. GFAJ-1 (WP-009098816), *Halomonas* sp. KHS3 (WP-041159480), *Halomonas alkaliphile* (WP-162218603), *Halomonas* sp. ZH2S (WP-160419650), *Halomonas alkaliantarctica* (WP-133732469), *Halomonas zincidurans* (WP-031384106), *Halomonas chromatireducens* (WP-083517585), *Halomonas* sp. KO116 (WP-035563078), *Halmonas* sp. A40-4 (WP-199285424), *Halomonas ventosae* (WP-035579360), *Halomonas* sp. HAL1) WP-008958555), *Halomonas* sp. MES3-P3E (WP-101146070), *Halomonas* sp. 1513 (WP-083700770), *Halomonas* sp. GT (WP-083007892), *Halomonas* sp. PA5 (QJQ97022), *Halomonas songnenensis* (WP-106373458), *Halomonas subglaciescola* (WP-079553041), *Halomonas* sp. HL-92 (WP-074398447), *Halomonas xinjiangensis* (WP-197053288), *Halomonas saliphila* (WP-104202516), *Halomonas* sp. HL-48 (WP-027336292), *Halomonas qijiaojingensis* (WP-189471950), *Halomonas urumqiensis* (WP-102588859), *Halomonas lutea* (WP-019020614), *Halomonas lutescens* (WP-188638020), *Halomonas salicampi* (WP-179930793), *Halomonas* sp. FME66 (WP-193092800), *Halomonas* sp. 156 (CAD5269671), *Halomonas* sp. L5 (WP-149329933), *Halomonas nanhaiensis* (WP-127060197), *Halomonas titanicae* (WP-144810212), *Halomonas* sp. SH5A2 (WP-186255949), *Halomonas* sp. TD01 (WP-009722522), *Halomonas* sp. PC (WP-127040515), *Halomonas* sp. RC (WP-126951333), *Halomonas* sp. DQ26W (WP-114573011), *Halomonas* sp. TQ8S (WP-114486842), *Halomonas* sp. PYC7W (WP-114478819), *Halomonas* sp. LBP4 (WP-181421925), *Halomonas* sp. QX-1 (WP-176303735), *Halomonas* sp. QX-2 (WP-180092182), *Halomonas glaciei* (WP-179915254), *Halomonas zhaodongensis* (WP-179927495), *Halomonas xianhensis* (WP-092845804), *Halomonas gudaonensis* (WP-089686750), *Halomonas humidisoli* (WP-095603093), *Halomonas boliviensis* (WP-083825729), *Halomonas* sp. QHL1 (WP-083571058), *Halomonas ilicicola* (WP-072822829), *Halomonas saccharevitans* (WP-089847692), *Halomonas muralis* (WP-089729617), *Halomonas arcis* (WP-089706930), *Halomonas boliviensis* (WP-040480056), *Halomonas andesensis* (WP-126944084), *Halomonas* sp. G5-11 (WP-168017113), *Halomonas* sp. THAF5a (QFU03326), *Halomonas taeanensis* (SDG32001), *Halorussus* sp. RC-68 (WP-128475846), *Halorussus ruber*(WP-135825713), *Halorussus* sp. ZS-3 (WP-158056449), *Halorussus* sp. HD8-83 (WP-135830119), *Halorussus salinus* (WP-135854680), *Halorussus amylolyticus* (WP-132060623), *Halorussus* sp. MSC15.2 (WP-163523881), *Haloterrigena limicola* (WP-008010666), *Haloterrigena hispanica* (WP-149782231), *Haloterrigena* sp. H1 (WP-138782397), *Isoptericola halotolerans* (WP-171781920), *Marinobacter* sp. X15-166B (WP-198929205), *Marinobacter* sp. LPB0319 (WP-2066439888), *Marinobacter salaries* (WP-126811858), *Marinobacter* sp. PJ-16 (WP-137435339), *Marinobacter nanhaiticus* (WP-004579452), *Marinobacter bohaiensis* (WP-111497193), *Marinobacter* sp. ANT_B65 (WP-202971753), *Marinobacter sediminum* (WP-203299860), *Marinobacter fonticola* (WP-148861082), *Marinobacter* sp. JB02H27 (WP-150989051), *Marinobacter maritimus* (WP-144775354), *Marinobacter nitratireducens* (WP-036130189), *Marinobacter aromaticivorans* (WP-100686899), *Marinobacter* sp. MCTG268 (WP-081899301), *Marinobacter profundi* (WP-099614009), *Marinobacter* sp. R17 (WP-123633665), *Marinobacter* sp. F3R11 (WP-113816648), *Marinobacter lipolyticus* (WP-012136507), *Marinobacter* sp. LV10MA510-1 (WP-098421792), *Marinobacter* sp. LV10R520-4 (WP-143751449), *Marinobacter antarcticus* (WP-072795398), *Marinobacter zhejiangensis* (WP-092022278), *Marinobacter* sp. LZ-8 (WP-138439039), *Marinobacter* sp. LZ-6 (WP-138437074), *Marinobacter* sp. DS40M8 (WP-169052525), *Marinobacter shengliensis* (WP-106694886), *Marinobacter algicola* (WP-007152654), *Marinobacter salicampi* (WP-166253549), *Marinobacter* sp. JSM 1782161 (WP-165857264), *Methyloligella halotolerans* (WP-069095898), *Micromonospora halophytica* (WP-091291516), *Natronococcus* sp. LS1_42 (WP-148858780), *Nocardiopsis halotolerans* (WP-017570132), *Paracoccus halophilus* (WP-036743786), *Roseivivax halodurans* (WP-037257008), *Saccharomonospora halophila* (WP-157601674), *Shewanella vesiculosa* (NCO72699), *Shewanella psychrophila* (WP-077755816), *Shewanella frigidimarina* (WP-123883413), *Shewanella khirikhana* (WP-126168307), *Shewanella halifaxensis* (WP-108946642), *Shewanella waksmanii* (WP-028774143), *Shewanella saliphila* (WP-188922486), *Shewanella ulleungensis* (WP-188954542), *Shewanella litoralis* (WP-160052797).

Extremophilic enzymes 102 produced by acidophiles can be utilized in some aspects. For instance, acidophilic enzymes that exhibit activity at a pH of from about 1 to about 5.5 can be utilized. Exemplary acidophiles (and acidophilic enzymes produced thereby) encompassed herein can include, without limitation, *Acidibrevibacterium fodinaquatile* (WP-162800754), *Acidicaldus* sp (HGC43174), *Acidiphilium cryptum* (WP-050751056), *Acidisphaera rubrifaciens* (WP-084623200), *Acidisphaera* sp. S103 (WP-158926549), *Acidobacteria bacterium* (MB14850940), *Acidobacteriales bacterium* (MBA3914351), *Acidimicrobiaceae bacterium* (TPW09344), *Acidothermus cellulolyticus* (WP-011719018), *Acidovorax* sp. (RZJ59385), *Acidovorax* sp. Leaf160 (WP-156382378), *Acidovorax citrulli* (WP-116212334), *Acidovorax* sp. ST3 (WP-110960035), *Acidovorax* sp. SD340 (WP-055393692), *Acidovorax* sp. JHL-9 (WP-026434583), *Acidovorax* sp. JHL-3 (WP-024815995), *Acidovorax* sp. 59 (WP-099731663), *Acidovorax* sp. T1 (WP-087747071), *Acidovorax radices* (WP-145694120), *Acidovorax citrulli* (MVT28077), *Acidovorax konjaci* (WP-184273732), *Acidovorax* sp. YL-MeA13-2016 (WP-179683865), *Acidovorax* sp. JMULE5 (WP-176888736), Acidovorax carolinensis (WP-086926820), Acidovorax sp. Root219 (WP-057264729), Acidovorax sp. Root217 (WP-057200451), Acidovorax sp. Root70 (WP-056639581), Acidovorax sp. Root267 (WP-057271450), Acidovorax sp. Root275 (WP-057228519), Acidovorax sp. Root568 (WP-056742554), Acidovorax sp. Root402 (WP-056056880), Acidovorax sp. Leaf78 (WP-056167938), Acidovorax sp. CF316 (WP-007848954), Acidovorax sp. NO-1 (WP-008904688), Acidovorax sp. KKS102 (WP-015015374), Acidovorax sp. BoFeN1 (WP-114656624), Acidovorax sp. MR-S7 (WP-020227330), Acidovorax sp. GW101-3H11 (WP-063462297), Acidovorax sp. 100 (WP-121942233), Acidovorax sp. 94 (WP-121421729), Acidovorax sp. 93 (WP-121508058), Acidovorax sp. IB03 (WP-198847087), Acidovorax facilis (WP-182119389), Acidovorax cattleya (WP-196290774), Acidovorax soli (WP-184855240), Acidovorax sp. TP4 (BAA35137), Acidovorax sp. HMWFO18 (WP-199227795), Acidovorax sp. 107 (WP-108624875), Acidovorax sp. 69 (WP-100412617), Acidovorax sp. RAC01 (WP-069104250), Acidovorax avenae (WP-107129247), Acidovorax sp. ACV01 (WP-192426852), Acidovorax sp. ACV02 (WP-192419383), Acidovorax sp. SRB_14 (WP-173025722), Acidovorax sp. 99 (WP-116748450), Acidovorax delafieldii (WP-060985808), Acidovorax sp. 16-35-5 (WP-175506463), Acidovorax valerianellae (WP-092740663), Acidovorax temperans (WP-142084895), Acidovorax oryzae (WP-026433360), Acidovorax sp. SRB_24 (WP-169168665), Acidovorax cavernicola (WP-119555154), Acidovorax temperans (WP-044398345), Acidisoma sp. S159 (WP-159014448), Acidisoma sp. L85 (WP-158802619), Acidisphaera sp. L21 (WP-158747166), Acidiphilium cryptum JF-5 (ABQ28771), Actinospica acidiphila (WP-193455356), Alicyclobacillus pomorum (WP-084453829), Amycolatopsis acidiphila (WP-144638401), Azospirillum baldaniorum (WP-014240680), Bacillus megaterium (WP-013057692), Catenulispora acidiphila (WP-015793547), Delftia sp. UME58 (WP-183018265), Delftia acidovorans (WP-202760212), Delftia lacustris (WP-016453321), Methylocapsa acidiphila (WP-026607232), Paraburkholderia acidophila (WP-084908171), Paraburkholderia acidisoli (WP-158957882), Paraburkholderia acidipaludis (WP-027796272), Priestia megaterium (WP-016764703), Rhizobium acidisoli (WP-054183259), Rhodoblastus acidophilus (WP-088519736), Stenotrophomonas acidaminiphila (WP-054666853), Streptomyces acidiscabies (WP-078480871), Streptomyces acidicola (WP-152864677).

Extremophilic enzymes 102 produced by alkaliphiles can be utilized in some aspects. For instance, alkaliphilic enzymes that exhibit activity at a pH of from about 7.5 to about 11.5) can be utilized. Exemplary alkaliphiles (and alkaliphilic enzymes produced thereby) encompassed herein can include, without limitation, Alkalilacustris brevis (WP-114966465), Alkalihalobacillus macyae (WP-152670966), Alkalihalobacillus pseudofirmus (WP-012960136), Alkalihalobacillus shacheensis (WP-082676287), Alkalihalobacillus xiaoxiensis (WP-204463621), Alkalilimnicola sp. S0819 (WP-152144452), Alkalimonas amylolytica (WP-091344878), Amycolatopsis alkalitolerans (WP-139096058), Cupriavidus alkaliphilus (WP-111516860), Ensifer alkalisoli (WP-151613639), Lacimicrobium alkaliphilum (WP-062478888), Lysobacter alkalisoli (QDH70273), Massilia alkalitolerans (WP-036214799), Methylobacter sp. B2 WP-174627553), Neorhizobium alkalisoli (WP-105385441), Nocardiopsis alkaliphile (WP-051045978), Ramlibacter alkalitolerans (WP-201687394), Spinactinospora alkalitolerans (WP-179641803).

Extremophilic enzymes 102 produced by piezophiles can be utilized in some aspects. For instance, piezophilic enzymes that exhibit activity at a pressure of about 110 kPa or greater, or about 50 MPa or greater in some aspects, can be utilized. Exemplary piezophiles (and piezophilic enzymes produced thereby) encompassed herein can include, without limitation, Oceanobacillus piezotolerans (WP-121525044), Oceanobacillus profunda (WP-169713018), Colwellia marinimaniae (WP-082606415), Salinimonas sediminis (WP-108566897).

Radiation resistant extremophiles 102 are also encompassed herein. For instance radiation resistant organisms such as Deinococcus radiotolerans which produces a radiation resistant enzyme (WP_189068351) can be utilized. A radiation resistant organism and radiation resistant enzyme encompassed herein can generally be active at a level of acute ionizing radiation (gamma rays, high energy UV rays, X-rays, etc.) of about 1000 Gy or greater, or about 2000 Gy or greater in some aspects.

Bacteria well suited for use in the present disclosure along with Accession numbers for suitable polymerases and depolymerases, for instance, are listed in Table 1 below. As discussed above, it should be understood that the microorganisms listed in the tables herein may be used in one or more of the first vessel and second vessel, or alternatively, one or more enzymes therefrom. May be used in one or more of the first vessel and second vessel.

TABLE 1

| Organism | Accession Number | |
|---|---|---|
| | Polymerase | Depolymerase |
| Lysobacter aestuarii | WP_141519092 | QDH70273 |
| Lysobacter antibioticus | WP_057917797 | WP_075575206 |
| Lysobacter antibioticus | WP_064749485 | WP_057971776 |
| Lysobacter antibioticus | WP_031370714 | WP_057970457 |
| Lysobacter bugurensis | WP_189454736 | WP_189453172 |
| Lysobacter capsici | WP_036103061 | WP_036102479 |
| Lysobacter capsici | WP_191821024 | WP_082723829 |
| Lysobacter enzymogenes | WP_057947866 | WP_074867011 |
| Lysobacter enzymogenes | WP_206409599 | WP_206412663 |
| Lysobacter enzymogenes | WP_123648422 | WP_096378935 |
| Lysobacter enzymogenes | WP_078996336 | WP_096378891 |
| Lysobacter lacus | WP_149351326 | WP_149353094 |
| Lysobacter lycopersici | WP_143878270 | WP_111268077 |
| Lysobacter maris | WP_111268029 | WP_141481346 |
| Lysobacter niastensis | WP_194931164 | WP_194930566 |
| Lysobacter profundi | WP_159015985 | WP_199268782 |
| Lysobacter sp. | MBA2238340 | MBA3486130 |
| Lysobacter sp. | NOT90012 | NOT88901 |
| Lysobacter sp. | TXI44079 | TXI49260 |
| Lysobacter sp. | TBR06965 | TBR07230 |
| Lysobacter sp. A03 | WP_043958955 | WP_043958589 |
| Lysobacter sp. cf310 | WP_091637072 | SFK67843 |
| Lysobacter sp. H21R20 | WP_193987019 | WP_193986963 |
| Lysobacter sp. H21R4 | WP_194342245 | WP_194342197 |
| Lysobacter sp. H23M41 | WP_194035564 | WP_194035504 |
| Lysobacter sp. R19 | WP_200614426 | MBK3415203 |
| Lysobacter sp. Root604 | WP_056175356 | WP_056174125 |
| Lysobacter sp. Root690 | WP_056115057 | WP_056115653 |
| Lysobacter sp. Root916 | WP_057163275 | WP_082578417 |
| Lysobacter sp. Root983 | WP_057159495 | WP_057162992 |
| Lysobacter sp. TY2-98 | WP_115646306 | WP_057159102 |
| Lysobacter spongiae | WP_182687030 | WP_182685163 |
| Lysobacter spongiicola | WP_078757079 | WP_200809237 |

In one aspect, PHBDase/bacterium/archaea for use as disclosed herein can include polyextremophiles that exist at a combination of extreme environmental conditions. For example, a halophilic alkalithermophile, which ideally exist at both high saline and alkaline conditions, or a psychrotrophic halophile, which ideally exist at both low temperature and high saline conditions. Most of the piezophilic (pressure-loving) extremophiles are found at the bottom of the ocean and are therefore also halophilic (salt-loving) and psychrophilic (cold-loving), all of which are conditions that can be simultaneously generated and maintained within a reaction chamber to provide mesophilic pathogen decontamination. In such an aspect, mesophilic contamination can be addressed through multiple mechanisms in conjunction with a depolymerization reaction catalyzed by a single polyextremophilic enzyme.

For instance, in one aspect, the extremophilic microorganism 102 incorporated into the present disclosure is selected from a variety of bacterial genera including those listed in Table 2 below.

TABLE 2

| Genus | Nature of the polyextremophile |
|---|---|
| Deienococcus | Psychrophile, Radiation resistant |
| Arthrobacter | Psychrophile, pH extreme |
| Alicyclobacillus | Thermophile, pH extreme |
| Zunongwangia | Psychrophile, Halophile |
| Psychromonas | Psychrophile, Piezophile |
| Halomonas | Psychrophile, Halophile, pH extreme, Piezophile |
| Natronococcus | Halophile, pH extreme |
| Natranaerobius | Halophile, pH extreme, pH extreme |
| Colwellia | Psychrophile, Piezophile |
| Pseudoaltermonas | Psychrophile, Halophile |
| Altermonas | Psychrophile, Halophile |
| Halobacteriaceae | Halophile, Piezophile, Psychrophile |
| Marinobacter | Psychrophile, Halophile |
| Hyphomonas | Thermophile, Piezophile |
| Amycolatopsis | Thermophile, pH extreme |
| Georgenia | Thermophile, pH extreme |
| Acidothermus | Thermophile, pH extreme |
| Halobacillus | Halophile, pH extreme |
| Nesterenkonia | Psychrophile, halophile, pH extreme |
| Salimonas | Psychrophile, Piezophile, Halophile |
| Thermobifida | Thermophile, pH extreme, Halophile |

A number of the extremophiles and extremophilic enzymes 102 mentioned are polyextremophiles. Exemplary polyextremophiles (and polyextremophilic enzymes produced thereby) encompassed herein can include, without limitation (some of which are also included in those referred to previously), Acidothermus cellulolyticus (WP_011719018), Arthrobacter crystallopoietes (WP_005270754), Arthrobacter sp. NEB 688 (WP_173027059), Amycolatopsis decaplanina (WP_007028471), Amycolatopsis azurea (WP_039919726), Amycolatopsis orientalis (WP_044853678), Amycolatopsis regifaucium (WP_061985795), Amycolatopsis alba (WP_020632115), Amycolatopsis sp. CB00013 (WP_073845662), Amycolatopsis sp. WAC 04182 (WP_125683401), Amycolatopsis sp. WAC 04197 (WP_125733174), Amycolatopsis sp. WAC 01416 (WP_125797595), Amycolatopsis lurida (WP_034314791), Amycolatopsis australiensis (WP_072479564), Amycolatopsis sp. WAC 01375 (WP_125786221), Amycolatopsis sp. YIM 10 (WP_194239921), Amycolatopsis australiensis (WP_072480012), Amycolatopsis sp. WAC 01376 (WP_125797552), Amycolatopsis sp. WAC 01376 (WP_125791151), Amycolatopsis sp. BJA-103 (WP_168214428), Amycolatopsis sp. WAC 04169 (WP_125694889), Amycolatopsis sp. YIM 10 (WP_153034611), Amycolatopsis xylanica (WP_091289432), Amycolatopsis thailandensis (WP_093938547), Amycolatopsis tolypomycina (WP_091314877), Amycolatopsis (WP_094002797), Amycolatopsis mediterranei (WP_013227677), Amycolatopsis tolypomycina (WP_091316988), Amycolatopsis mediterranei (WP_013225900), Amycolatopsis sp. MJM2582 (WP_037335097), Amycolatopsis pretoriensis (WP_086680613), Amycolatopsis mediterranei (WP_014467631), Amycolatopsis mediterranei (WP_013227743), Amycolatopsis lexingtonensis (WP_086861387), Amycolatopsis balhimycina (WP_026468360), Amycolatopsis tolypomycina (WP_091309318), Amycolatopsis mediterranei (WP_013225589), Amycolatopsis lexingtonensis (WP_086864508), Amycolatopsis balhimycina (WP_020640708), Amycolatopsis balhimycina (WP_020639925), Amycolatopsis japonica (WP_038521005), Amycolatopsis vancoresmycina (WP_051767789), Amycolatopsis vancoresmycina (WP_162146255), Amycolatopsis vancoresmycina (WP_003055279), Amycolatopsis vancoresmycina (WP_003059137), Amycolatopsis arida (WP_177216885), Amycolatopsis orientalis (WP_037305638), Amycolatopsis mediterranei U32 (ADJ49174), Amycolatopsis balhimycina (WP_020640186), Amycolatopsis balhimycina (WP_020646797), Amycolatopsis regifaucium (WP_158070237), Amycolatopsis umgeniensis (WP_184896802), Amycolatopsis mediterranei (WP_176742238), Amycolatopsis orientalis (WP_037318494), Amycolatopsis taiwanensis (WP_027941815), Amycolatopsis thermoflava (WP_037323546), Amycolatopsis nigrescens (WP_157357235), Amycolatopsis benzoatilytica (WP_020658806), Amycolatopsis thermoflava (WP_123687648), Amycolatopsis sp. MtRt-6 (WP_206788940), Amycolatopsis nigrescens (WP_020673950), Amycolatopsis sp. MtRt-6 (WP_206796628), Amycolatopsis sp. MtRt-6 (WP_206785025), Amycolatopsis sp. 195334CR (WP_206808196), Amycolatopsis sp. SID8362 (WP_166641473), Amycolatopsis vastitatis (WP_167441766), Amycolatopsis sp. MtRt-6 (WP_206794433), Amycolatopsis sp. 195334CR (WP_206804625), Amycolatopsis sp. SID8362 (WP_160695402), Amycolatopsis sp. 195334CR (WP_206805671), Amycolatopsis mediterranei S699 (AEK42609), Amycolatopsis sp. SID8362 (WP_160697844), Amycolatopsis ruanii (WP_116109633), Amycolatopsis vastitatis (WP_093953441), Amycolatopsis antarctica (WP_094864937), Amycolatopsis sp. SID8362 (WP_160697847), Amycolatopsis vastitatis (WP_093953193), Amycolatopsis rifamycinica (WP_043779284), Amycolatopsis rifamycinica (WP_043787922), Amycolatopsis orientalis (WP_044854926), Amycolatopsis albispora (WP_113697064), Amycolatopsis vastitatis (WP_093953762), Amycolatopsis keratiniphila (WP_043848437), Amycolatopsis rifamycinica (WP_043776526), Amycolatopsis sp, ATCC 39116 (WP_039791697), Amycolatopsis sp. CA-126428 (WP_199191631), Amycolatopsis sp. CA-128772 (WP_199199004), Amycolatopsis rifamycinica (WP_043775110), Amycolatopsis sp. CA-128772 (WP_103347542), Amycolatopsis sp. CA-126428 (WP_103341161), Amycolatopsis sp. CA-126428 (WP_103338297), Amycolatopsis sp. CA-128772 (WP_103347494), Amycolatopsis sp. CA-128772 (WP_103351389), Amycolatopsis sp. CA-126428 (WP_10334050), Amycolatopsis sp. CA-126428 (WP_103337215), Amycolatopsis sp. BJA-103 (WP_101611121), Amycolatopsis rifamycinica (WP_043775220), Amycolatopsis bullii (WP_191309718), Amycolatopsis alkalitolerans (WP_139096058), Amycolatopsis sp. CA-126428 (WP_103340450), Amycolatopsis sp. A23 (WP_155542679), Amycolatopsis sp. A23 (WP_155546301), Amycolatopsis bullii (WP_191313482), Amycolatopsis oliviviridis (WP_191256639), Amycolatopsis bullii(WP_191317041), Amycolatopsis sp. A23 WP_155546374), Amycolatopsis bullii(WP_191309628), Amycolatopsis sp. H6(2020) (MBE8525409), Amycolatopsis sp. H6(2020) (MBE8516875), Amycolatopsis acidiphila (WP_144638401), Amycolatopsis deserti (WP_191242759), Amycolatopsis sp. H6(2020) (MBE8523464), Amycolatopsis roodepoortensis (WP_192744003), Amycolatopsis lexingtonensis (WP_086861614), Amycolatopsis sp. H6(2020) (MBE8523449), Amycolatopsis lexingtonensis (WP_086861672), Amycolatopsis sp. H6(2020) (MBE8519699), Amycolatopsis eburnean (WP_125314097), Amycolatopsis sp. PIP199 (WP_181777181), Amycolatopsis eburnean (WP_125313793), Amycolatopsis sp. YIM 10 (WP_153034239), Amycolatopsis rhizosphaerae (WP_144585784), Amycolatopsis eburnea (WP_191984376), Amycolatopsis australiensis (WP_072479963), Amycolatopsis eburnea (WP_125313723), Amycolatopsis sp. Hca4 (WP_176178332), Amycolatopsis pretoriensis (WP_086674376), Amycolatopsis sp. YIM 10 (WP_153033440), Amycolatopsis sp. Hca4 (WP_176171164), Amycolatopsis thermalba (WP_115944128), Amycolatopsis tolypomycina (WP_091313624), Amycolatopsis sacchari (WP_09150482), Amycolatopsis kentuckyensis (WP_086849953), Amycolatopsis pretoriensis (WP_086676731), Amycolatopsis kentuckyensis (WP_086838850), Amycolatopsis vancoresmycina (WP_033262149), Amycolatopsis sacchari (WP_091509483), Amycolatopsis eburnea (RSD12104), Amycolatopsis vancoresmycina (WP_033262457), Amycolatopsis tolypomycina (WP_091314771), Amycolatopsis kentuckyensis (WP_086842561), Amycolatopsis tolypomycina (SED02538), Amycolatopsis kentuckyensis (WP_086850817), Amycolatopsis keratiniphila (SDU59319), Amycolatopsis sp. SID8362 (NBH10816), Amycolatopsis sacchari (SF91313), Amycolatopsis keratiniphila (AGM10176), Amycolatopsis vancoresmycina DSM 44592 (EOD69417), Amycolatopsis vancoresmycina DSM 44592 (EOD63279), Colwellia psychrerythraea (WP_033095470), Colwellia psychrerythraea (WP_033082346), Colwellia chukchiensis (WP_085285385), unclassified Colwellia (WP_182245161), unclassified Colwellia (WP_108456828), Colwellia (WP_082606415), unclassified Colwellia (WP_182136131), unclassified Colwellia (WP_182222214), Colwellia psychrerythraea (WP_138140233), unclassified Colwellia (WP_182213899), unclassified Colwellia (WP_182191078), Colwellia psychrerythraea (WP_033082290), Colwellia sp. Arc7-635 (WP_126668020), Colwellia aestuarii (WP_143323591), Colwellia sp. BRX8-4 (WP_182258889), Colwellia sp. (MBL4900302), Colwellia sp. (MBL0710453), Colwellia sp. PAMC 21821 (WP_081180401), Colwellia sp. (MBL4764635), Colwellia sp. 12G3 (WP_101233926), Colwellia polaris (WP_085306422), Colwellia sp. Bg11-28 (WP_157825823), Colwellia sp. BRX10-3 (WP_182133028), Colwellia sp. MB02u-6 (WP_182233718), Colwellia sp. BRX8-2 (WP_182231462), Colwellia sp. MB3u-4 (WP_182185277), Colwelllia sp. BRX9-1 (WP_182230151), Colwellia sp. BRX8-7 (WP_182242732), Colwellia sp. (NQZ90610), Colwellia sp. MB02u-10 (WP_182238471), Colwellia sp. (NQZ28611), Colwellia sp. (QY47923), Colwellia sp. Bg11-12 (WP_182229555), Colwellia sp. (NQY89088), Colwellia beringensis (WP_081152231), Colwellia sp. (NQZ82584), Colwellia demingiae (WP_146789187), Candidatus Colwellia aromaticivorans (WP_114327742), Colwellia sp. MB02u-9 (WP_182197537), Colwellia mytili (WP_085299583), Colwellia sp. (NQY47915), Colwellia sp. (NQZ28619), Haladaptatus paucihalophilus (WP_007977720), Haladaptatus litoreus (WP_076429835), Haladaptatus paucihalophilus (WP_007977722), Haladaptatus sp. R4 (WP_066143160), Haladaptatus cibarius (WP_049970104), Haladaptatus sp. (W1 WP_069450211), Haladaptatus cibarius (WP_049971911), Haladaptatus paucihalophilus DX253 (SHK49397), Halobacillus ihumii (WP_163527944), Halobacillus hunanensis (WP_139377117), Halomarina oriensis (WP_124957125), Halomarina oriensis (WP_158204529), Halomonas (ventosae) (WP_035579360), Halomonas sp. 156 (CAD5269671), unclassified Halomonas (WP_008956714), Halomonas (WP_035577590), Halomonas chromatireducens (WP_083517585), Halomonas meridiana (WP_083602247), unclassified Halomonas (sp. HL-92) (WP_074398447), Halomonas sp. GFAJ-1 (WP_009101808), Halomonas chromatireducens (WP_066448186), Halomonas sp. K0116 (WP_035563078), Halomonas sp. K0116 (WP_035565981), Halomonas arcis (WP_089708323), Halomonas sp. TD01 (WP_009724586), Halomonas arcis (WP_089706930), Halomonas korlensis (WP_089792833), Halomonas alkaliantarctica (WP_133732469), Halomonas ilicicola (WP_072822829), Halomonas boliviensis (WP_007114283), Halomonas sp. HL-48 (WP_027336292), Halomonas alkaliphila (WP_038486873), unclassified Halomonas (WP_074394764), Halomonas sp. HAL1 (WP_008958555), Halomonas subglaciescola (WP_079553041), Halomonas korlensis (WP_089797758), Halomonas cerina (WP_183325502), unclassified Halomonas (sp. RC) (WP_126951333), Halomonas sp. TD01 (WP_009722522), Halomonas titanicae (WP_089691351), Halomonas aquamarina (WP_089674669), Halomonas gudaonensis (WP_089686750), Halomonas alkaliantarctica (WP_133731111), Halomonas saccharevitans (WP_089847692), Halomonas xianhensis (WP_092845804), Halomonas songnenensis (WP_106373458), Halomonas zincidurans (WP_031384106), Halomonas lutea (WP_019020614), Halomonas boliviensis (WP_083825729), Halomonas sp. GFAJ-1 (WP_009098816), Halomonas muralis (WP_089729617), Halomonas boliviensis (WP_040480056), Halomonas sp. (HAA45741), Halomonas zhanjiangensis (WP_040460201), Halomonas campaniensis (WP_088701082), Halomonas alkaliphile (WP_162218603), Halomonas sp. ZH2S (WP_160419650), Halomonas endophytica (WP_102654199), Halomonas sp. ALS9 (WP_064233856), Halomonas sp. KHS3 (WP_041159480), Halomonas salicampi(WP_179930793), Halomonas salicampi (WP_179928774), Halomonas heilongjiangensis (WP_102629242), Halomonas campaniensis (WP_088701419), Halomonas sp. MES3-P3E (WP_101146070), Halomonas alkaliantarctica (WP_030070137), Halomonas xinjiangensis (WP_197053288), Halomonas alkaliantarctica (WP_030072571), Halomonas sp. GT (WP_083002052), Halomonas sp. A40-4 (WP_199285424), Halomonas sp. GT (WP_083007892), Halomonas sp. 1513 (WP_076746720), Halomonas sp. HL-48 (WP_027335517), Halomonas sp. 1513 (WP_083700770), Halomonas sp. (MBL1266350), Halomonas urumqiensis (WP_102588859), Halomonas lutescens (WP_188638020), Halomonas lutescens (WP_188638515), Halomonas sp. FME66 (WP_193092800), Halomonas saliphila (WP_104202516), Halomonas sp. (MBE0488383), Halomonas qijiaojingensis (WP_189471950), Halomonas sp. 3(2) (WP_151442249), Halomonas sp. FME20 (WP_192536925), Halomonas sp. SH5A2 (WP_186255949), Halomonas sp. TQ8S (WP_114486842), Halomonas titanicae (WP_144812651), Halomonas sp. PYC7W (WP_114478819), Halomonas sp. PYC7W (WP_114478692), Halomonas sp. LBP4 (WP_181421925), Halomonas sp. TQ8S (WP_114487405), Halomonas glaciei(WP_179915254), Halomonas sp. QX-2 9 (WP_180092182), Halomonas sp. SH5A2 (WP_186253301), Halomonas zhaodongensis (WP_179927495), Halomonas titanicae (WP_144810212), Halomonas nanhaiensis (WP_127060197), Halomonas pantelleriensis (WP_089659512), Halomonas zhaodongensis (WP_179926908), Halomonas humidisoli (WP_095603093), Halomonas sp. QHL1 (WP_083571058), Halomonas sp. PC (WP_127040515), Halomonas sp. DQ26W (WP_114573011), Halomonas shengliensis (WP_089679049), Halomonas sp. QX-1 (WP_176303735), Halomonas sp. QHL1 (WP_071693265), Halomonas korlensis (WP_089794761), Halomonas aestuarii (WP_071946866), Halomonas sp. PR-M31 (WP_048308188), Halomonas sp. PA5 (QJQ97022), Halomonas andesensis (WP_126944084), Halomonas sp. PA5 (QJQ94877), Halomonas sp. L5 (WP_149329933), Halomonas korlensis (SFU56513), Halomonas sp. G5-11 (WP_168017113), Halomonas subterranean (WP_092824778), Halomonas sp. (HDZ47214), Halomonas sp. THAF5a (QFU03326), Halomonas sp (HDZ46744), Halomonas chromatireducens (AMD02558), Halomonas andesensis (WP_126948398), Halomonas korlensis (SFU93166), Halomonas taeanensis (SDG32001), Halorussus salinus (WP_135854385), Halorussus sp. MSC15.2 (WP_163523881), Halorussus salinus (WP_135854680), Halorussus amylolyticus (WP_132060623), Halorussus sp. ZS-3 (WP_158056449), Halorussus amylolyticus (WP_132060625), Halorussus sp. ZS-3 (WP_158056448), Halorussus sp. RC-68 (WP_128475846), Halorussus ruber (WP_135825713), Halorussus ruber (WP_135825712), Halorussus sp. HD8-83 (WP_135830119), Marilnobacter sp. LV10R520-4 (WP_143751449), Marinobacter zhejiangensis (WP_092022278), unclassified Marinobacter (WP_150989051), Marinobacter nitratireducens (WP_036130189), Marinobacter salarius (WP_091640839), unclassified Marinobacter (WP_098419392), Marinobacter algicola (WP_007152654), Marinobacter antarcticus (WP_072795398), unclassified Marinobacter (WP_152438805), Marinobacter (WP_075197007), Marinobacter profundi (WP_099614009), Marinobacter sp. LPB0319 (WP_206643988), Marinobacter sp. DS40M8 (WP_169052525), Marinobacter sp. X15-166B (WP_198929205), unclassified Marinobacter (WP_081899301), Marinobacter sp. PJ-16 WP_137435339), Marinobacter bohalensis (WP_111497193), Marinobacter sediminum (WP_203299860), Marinobacter lipolyticus (WP_012136507), Marinobacter sp. ANT_B65 (WP_202971753), Marinobacter nanhaiticus (WP_004579452), Marinobactersalarius (WP_126811858), Marinobactermaritimus (WP_144775354), Marinobacter sp. F3R11 (WP_113816648), Marinobacter sp. LZ-8 (WP_138439039), Marinobacter sp. LZ-6 (WP_138437074), Marinobacter shengliensis (WP_106694886), Marinobacter fonticola (WP_148861082), Marinobacter sp. JSM 1782161 (WP_165857264), Marinobacter sp. R17 (WP_123633665), Marinobacter salicampi (WP_166253549), Marinobacter sp. LV10MA510-1 (WP_098421792), Thermobifida fusca (WP_016187994), Zunongwangia atlantica 22II14-10F7 (ORL471960).

For instance, in one aspect, the extremophilic microorganism or an enzyme therefrom 102 incorporated into the product of the present disclosure are selected from a variety of bacterial genera and organisms including those listed in Table 3 below.

TABLE 3

Thermophile and Thermotolerant Organisms:

| | |
|---|---|
| Alicyclobacillus pomorum | WP-084453829 |
| Amycolatopsis thermoflava | WP-123687648 |
| Amycolatopsis thermalba | WP-094002797 |
| Amycolatopsis rumanii | WP-116109633 |
| Azospirillum thermophilum | WP-109324320 |
| Deinococcus actinosclerus | WP-082689076 |
| Fervidobacterium gondwanense | SHN54810 |
| Gandjariella thermophila | WP-137812779 |
| Georgenia satyanarayanai | WP-146237554 |
| Hyphomanas sp. | HAO37884 |
| Lihuaxuella thermophila | WP-089972404 |
| Microbulbifer thermotolerans | WP-197462976 |
| Minwuia thermotolerans | WP-206420073 |
| Rhodopseudomonas thermotolerans | WP-114356866 |
| Rhodopseudomonas pentothenatexigens | WP-114356866 |
| Streptomyces thermovulgaris | WP-067396676 |
| Thermanaeromonas toyohensis | WP-084666479 |
| Thermoactinomyces sp. CICC 10523 | WP-198056464 |
| Thermoactinomyces daqus | WP-033100012 |
| Thermoactinospora sp. | NUT44302 |
| Thermoactinospora rubra | WP-084965756 |
| Thermobifida halotolerans | WP-068692693 |
| Thermobifida fusca | WP-011290529 |
| Thermobispora bispora | WP-206206594 |
| Thermocatellispora tengchongensis | WP-185055796 |
| Thermochromatium tepidum | WP-153975900 |
| Thermocrispum municipal | WP-028851041 |
| Thermoflavimicrobium dichotomicum | WP-093229000 |
| Thermogemmatispora carboxidivorans | WP-081839208 |
| Thermogemmatispora aurantia | WP-151728970 |
| Thermogemmatispora tikiterensis | WP-11243376 |
| Thermogemmatispora onikobensis | WP-084659191 |
| Thermoleophilaceae bacterium | MBA2429278 |
| Thermomonospora echinospora | WP-160147065 |
| Thermomonospora cellulosilytica | WP-182704610 |
| Thermomonospora amylolytica | WP-198679325 |
| Thermostaphylospora chromogena | WP-093263254 |
| Thermus thermophilus | WP-197735236 |
| Thermus aquaticus | WP-053768217 |
| Thermus islandicus | HEO42284 |

Halophile and Halotolerant Organisms:

| | |
|---|---|
| Alteromonas halophila | WP-189403400 |
| Arthrobacter crystallopoietes | WP-005270754 |
| Arthrobacter sp. NEB 688 | WP-173027059 |
| Azospirillum halopraeferens | WP-029007775 |
| Empedobacter haloabium | TXE30443 |
| Desulfovibrio sulfodismutans | NDY59052 |
| Halobacillus hunanensis | WP-139377117 |

| | |
|---|---|
| *Halobacillus ihumii* | WP-16352794 |
| *Halobacteriovorax marinus* | WP-157868258 |
| *Haloechinothrix halophila* | WP-051400222 |
| *Halomarina oriensis* | WP-158204529 |
| *Halomonas cerina* | WP-183325502 |
| *Halomonas korlensis* | WP-089794761 |
| *Halomonas* sp. PR-M31 | WP-048308188 |
| *Halomonas aquamarina* | WP-089674669 |
| *Halomonas zhanjiangensis* | WP-040460201 |
| *Halomonas aestuarii* | WP-071946866 |
| *Halomonas endophytica* | WP-102654199 |
| *Halomonas heilongjiangensis* | WP-102629242 |
| *Halomonas campaniensis* | WP-088701082 |
| *Halomonas alkaliphila* | WP-038486873 |
| *Halomonas* sp. ALS9 | WP-064233856 |
| *Halomonas* sp. GFAJ-1 | WP-009098816 |
| *Halomonas* sp. KHS3 | WP-041159480 |
| *Halomonas alkaliphile* | WP-162218603 |
| *Halomonas* sp. ZH2S | WP-160419650 |
| *Halomonas alkaliantarctica* | WP-133732469 |
| *Halomonas zincidurans* | WP-031384106 |
| *Halomonas chromatireducens* | WP-083517585 |
| *Halomonas* sp. KO116 | WP-035563078 |
| *Halomonas* sp. A40-4 | WP-199285424 |
| *Halomonas ventosae* | WP-035579360 |
| *Halomonas* sp. HAL1 | WP-008958555 |
| *Halomonas* sp. MES3-P3E | WP-101146070 |
| *Halomonas* sp. 1513 | WP-083700770 |
| *Halomonas* sp. GT | WP-083007892 |
| *Halomonas* sp. PA5 | QJQ97022 |
| *Halomonas songnenensis* | WP-106373458 |
| *Halomonas subglaciescola* | WP-079553041 |
| *Halomonas* sp. HL-92 | WP-074398447 |
| *Halomonas xinjiangensis* | WP-197053288 |
| *Halomonas saliphila* | WP-104202516 |
| *Halomonas* sp. HL-48 | WP-027336292 |
| *Halomonas qijiaojingensis* | WP-189471950 |
| *Halomonas urumqiensis* | WP-102588859 |
| *Halomonas lutea* | WP-019020614 |
| *Halomonas lutescens* | WP-188638020 |
| *Halomonas salicampi* | WP-179930793 |
| *Halomonas* sp. FME66 | WP-193092800 |
| *Halomonas* sp. 156 | CAD5269671 |
| *Halomonas* sp. L5 | WP-149329933 |
| *Halomonas nanhaiensis* | WP-127060197 |
| *Halomonas titanicae* | WP-144810212 |
| *Halomonas* sp. SH5A2 | WP-186255949 |
| *Halomonas* sp. TD01 | WP-009722522 |
| *Halomonas* sp. PC | WP-127040515 |
| *Halomonas* sp. RC | WP-126951333 |
| *Halomonas* sp. DQ26W | WP-114573011 |
| *Halomonas* sp. TQ8S | WP-114486842 |
| *Halomonas* sp. PYC7W | WP-114478819 |
| *Halomonas* sp. LBP4 | WP-181421925 |
| *Halomonas* sp. QX-1 | WP-176303735 |
| *Halomonas* sp. QX-2 | WP-180092182 |
| *Halomonas glaciei* | WP-179915254 |
| *Halomonas zhaodongensis* | WP-179927495 |
| *Halomonas xianhensis* | WP-092845804 |
| *Halomonas gudaonensis* | WP-089686750 |
| *Halomonas humidisoli* | WP-095603093 |
| *Halomonas boliviensis* | WP-083825729 |
| *Halomonas* sp. QHL1 | WP-083571058 |
| *Halomonas ilicicola* | WP-072822829 |
| *Halomonas saccharevitans* | WP-089847692 |
| *Halomonas muralis* | WP-089729617 |
| *Halomonas arcis* | WP-089706930 |
| *Halomonas boliviensis* | WP-040480056 |
| *Halomonas andesensis* | WP-126944084 |
| *Halomonas* sp. G5-11 | WP-168017113 |
| *Halomonas* sp. THAF5a | QFU03326 |
| *Halomonas taeanensis* | SDG32001 |
| *Halorussus* sp. RC-68 | WP-128475846 |
| *Halorussus ruber* | WP-135825713 |
| *Halorussus* sp. ZS-3 | WP-158056449 |
| *Halorussus* sp. HD8-83 | WP-135830119 |
| *Halorussus salinus* | WP-135854680 |
| *Halorussus amylolyticus* | WP-132060623 |
| *Halorussus* sp. MSC15.2 | WP-163523881 |
| *Haloterrigena limicola* | WP-008010666 |
| *Haloterrigena hispanica* | WP-149782231 |
| *Haloterrigena* sp. H1 | WP-138782397 |
| *Isoptericola halotolerans* | WP-171781920 |
| *Marinobacter* sp. X15-166B | WP-198929205 |
| *Marinobacter* sp. .LPB0319 | WP-2066439888 |
| *Marinobacter salarius* | WP-126811858 |
| *Marinobacter* sp. PJ-16 | WP-137435339 |
| *Marinobacter nanhaiticus* | WP-004579452 |
| *Marinobacter bohaiensis* | WP-111497193 |
| *Marinobacter* sp. ANT_B65 | WP-202971753 |
| *Marinobacter sediminum* | WP-203299860 |
| *Marinobacter fonticola* | WP-148861082 |
| *Marinobacter* sp. JB02H27 | WP-150989051 |
| *Marinobacter maritimus* | WP-144775354 |
| *Marinobacter nitratireducens* | WP-036130189 |
| *Marinobacter aromaticivorans* | WP-100686899 |
| *Marinobacter* sp. MCTG268 | WP-081899301 |
| *Marinobacter profundi* | WP-099614009 |
| *Marinobacter* sp. R17 | WP-123633665 |
| *Marinobacter* sp. F3R11 | WP-113816648 |
| *Marinobacter lipolyticus* | WP-012136507 |
| *Marinobacter* sp. LV10MA510-1 | WP-098421792 |
| *Marinobacter* sp. LV10R520-4 | WP-143751449 |
| *Marinobacter antarcticus* | WP-072795398 |
| *Marinobacter zhejiangensis* | WP-092022278 |
| *Marinobacter* sp. LZ-8 | WP-138439039 |
| *Marinobacter* sp. LZ-6 | WP-138437074 |
| *Marinobacter* sp. DS40M8 | WP-169052525 |
| *Marinobacter shengliensis* | WP-106694886 |
| *Marinobacter algicola* | WP-007152654 |
| *Marinobacter salicampi* | WP-166253549 |
| *Marinobacter* sp. JSM 1782161 | WP-165857264 |
| *Methyloligella halotolerans* | WP-069095898 |
| *Micromonospora halophytica* | WP-091291516 |
| *Natronococcus* sp. LS1_42 | WP-148858780 |
| *Nocardiopsis halotolerans* | WP-017570132 |
| *Paracoccus halophilus* | WP-036743786 |
| *Roseivivax halodurans* | WP-037257008 |
| *Saccharomonospora halophila* | WP-157601674 |
| *Shewanella vesiculosa* | NCO72699 |
| *Shewanella psychrophila* | WP-077755816 |
| *Shewanella frigidimarina* | WP-123883413 |
| *Shewanella khirikhana* | WP-126168307 |
| *Shewanella halifaxensis* | WP-108946642 |
| *Shewanella waksmanii* | WP-028774143 |
| *Shewanella saliphila* | WP-188922486 |
| *Shewanella ulleungensis* | WP-188954542 |
| *Shewanella litoralis* | WP-160052797 |

Acidophile or Acidotolerant Organisms:

| | |
|---|---|
| *Acidibrevibacterium fodinaquatile* | WP-162800754 |
| *Acidicaldus* sp | HGC43174 |
| *Acidiphilium cryptum* | WP-050751056 |
| *Acidisphaera rubrifaciens* | WP-084623200 |
| *Acidisphaera* sp. S103 | WP-158926549 |
| *Acidobacteria bacterium* | MBI4850940 |
| *Acidobacteriales bacterium* | MBA3914351 |
| *Acidimicrobiaceae bacterium* | TPW09344 |
| *Acidothermus cellulolyticus* | WP-011719018 |
| *Acidovorax* sp. | RZJ59385 |
| *Acidovorax* sp. Leaf160 | WP-156382378 |
| *Acidovorax citrulli* | WP-116212334 |
| *Acidovorax* sp. ST3 | WP-110960035 |
| *Acidovorax* sp. SD340 | WP-055393692 |
| *Acidovorax* sp. JHL-9 | WP-026434583 |
| *Acidovorax* sp. JHL-3 | WP-024815995 |
| *Acidovorax* sp. 59 | WP-099731663 |
| *Acidovorax* sp. T1 | WP-087747071 |
| *Acidovorax radices* | WP-145694120 |
| *Acidovorax citrulli* | MVT28077 |
| *Acidovorax konjaci* | WP-184273732 |
| *Acidovorax* sp. YL-MeA13-2016 | WP-179683865 |
| *Acidovorax* sp. JMULE5 | WP-176888736 |
| *Acidovorax carolinensis* | WP-086926820 |
| *Acidovorax* sp. Root219 | WP-057264729 |

| | |
|---|---|
| Acidovorax sp. Root217 | WP-057200451 |
| Acidovorax sp. Root70 | WP-056639581 |
| Acidovorax sp. Root267 | WP-057271450 |
| Acidovorax sp. Root275 | WP-057228519 |
| Acidovorax sp. Root568 | WP-056742554 |
| Acidovorax sp. Root402 | WP-056056880 |
| Acidovorax sp. Leaf78 | WP-056167938 |
| Acidovorax sp. CF316 | WP-007848954 |
| Acidovorax sp. NO-1 | WP-008904688 |
| Acidovorax sp. KKS102 | WP-015015374 |
| Acidovorax sp. BoFeN1 | WP-114656624 |
| Acidovorax sp. MR-S7 | WP-020227330 |
| Acidovorax sp. GW101-3H11 | WP-063462297 |
| Acidovorax sp. 100 | WP-121942233 |
| Acidovorax sp. 94 | WP-121421729 |
| Acidovorax sp. 93 | WP-121508058 |
| Acidovorax sp. IB03 | WP-198847087 |
| Acidovorax facilis | WP-182119389 |
| Acidovorax cattleya | WP-196290774 |
| Acidovorax soli | WP-184855240 |
| Acidovorax sp. TP4 | BAA35137 |
| Acidovorax sp. HMWF018 | WP-199227795 |
| Acidovorax sp. 107 | WP-108624875 |
| Acidovorax sp. 69 WP- | WP-100412617 |
| Acidovorax sp. RAC01 | WP-069104250 |
| Acidovorax avenae | WP-107129247 |
| Acidovorax sp. ACV01 | WP-192426852 |
| Acidovorax sp. ACV02 | WP-192419383 |
| Acidovorax sp. SRB_14 | WP-173025722 |
| Acidovorax sp. 99 WP- | WP-116748450 |
| Acidovorax delafieldii | WP-060985808 |
| Acidovorax sp. 16-35-5 | WP-175506463 |
| Acidovorax valerianellae | WP-092740663 |
| Acidovorax temperans | WP-142084895 |
| Acidovorax oryzae | WP-026433360 |
| Acidovorax sp. SRB_24 | WP-169168665 |
| Acidovorax cavernicola | WP-119555154 |
| Acidovorax temperans | WP-044398345 |
| Acidisoma sp. S159 | WP-159014448 |
| Acidisoma sp. L85 WP | WP-158802619 |
| Acidisphaera sp. L21 | WP-158747166 |
| Acidiphilium cryptum JF-5 | ABQ28771 |
| Actinospica acidiphila | WP-193455356 |
| Alicyclobacillus pomorum | WP-084453829 |
| Amycolatopsis acidiphila | WP-144638401 |
| Azospirillum baldaniorum | WP-014240680 |
| Bacillus megaterium | WP-013057692 |
| Catenulispora acidiphila | WP-015793547 |
| Delftia sp. UME58 | WP-183018265 |
| Delftia acidovorans | WP-202760212 |
| Delftia lacustris | WP-016453321 |
| Deinococcus radiotolerans | WP-189068351 |
| Methylocapsa acidiphila | WP-026607232 |
| Paraburkholderia acidophila | WP-084908171 |
| Paraburkholderia acidisoli | WP-158957882 |
| Paraburkholderia acidipaludis | WP-027796272 |
| Priestia megaterium | WP-016764703 |
| Rhizobium acidisoli | WP-054183259 |
| Rhodoblastus acidophilus | WP-088519736 |
| Stenotrophomonas acidaminiphila | WP-054666853 |
| Streptomyces acidiscabies | WP-078480871 |
| Streptomyces acidicola | WP-152864677 |

Alkaliphile or Alkali Tolerant Organisms:

| | |
|---|---|
| Alkalilacustris brevis | WP-114966465 |
| Alkalihalobacillus macyae | WP-152670966 |
| Alkalihalobacillus pseudofirmus | WP-012960136 |
| Alkalihalobacillus shacheensis | WP-082676287 |
| Alkalihalobacillus xiaoxiensis | WP-204463621 |
| Alkalilimnicola sp. S0819 | WP-152144452 |
| Alkalimonas amylolytica | WP-091344878 |
| Amycolatopsis alkalitolerans | WP-139096058 |
| Cupriavidus alkaliphilus | WP-111516860 |
| Ensifer alkalisoli | WP-151613639 |
| Lacimicrobium alkaliphilum | WP-062478888 |
| Lysobacter alkalisoli | QDH70273 |
| Massilia alkalitolerans | WP-036214799 |
| Methylobacter sp. B2 | WP-174627553 |
| Neorhizobium alkalisoli | WP-105385441 |
| Nocardiopsis alkaliphile | WP-051045978 |
| Ramlibacter alkalitolerans | WP-201687394 |
| Spinactinospora alkalitolerans | WP-179641803 |

Psychrophilic or Psychrotolerant Organisms:

| | |
|---|---|
| Alteromonas oceani | WP-123325050 |
| Alteromonas alba | WP-105936495 |
| Alteromonas sp. 38 | WP-201299304 |
| Alteromonas macleodii | WP-156078157 |
| Alteromonas ponticola | WP-169211550 |
| Alteromonas lipolytica | WP-070178363 |
| Arthrobacter crystallopoietes | WP-005270754 |
| Bosea psychrotolerans | WP-181011807 |
| Glaciecola amylolytica | WP-164472126 |
| Hyphomonas sp. | HAO37884 |
| Janthinobacterium psychrotolerans | WP-065307954 |
| Massilia psychrophila | WP-099914383 |
| Paraglaciecola psychrophile | WP-007642709 |
| Polaromonas sp. SP1 | WP-164483751 |
| Polaromonas sp. AER18D-145 | WP-096697750 |
| Polaromonas sp. CF318 | WP-007872516 |
| Polaromonas vacuolate | WP-168920719 |
| Polaromonas naphthalenivorans | WP-157040436 |
| Polaromonas sp. JS666 | WP-011482994 |
| Polaromonas glacialis | WP-084181426 |
| Polaromonas sp. EUR3 1.2.1 | WP-197028649 |
| Polaromonas sp. CG_9.2 | WP-196864241 |
| Polaromonas sp. CG_9.11 | WP-196869863 |
| Polaromonas eurypsychrophila | WP-188708524 |
| Polaromonas sp. | MBC7445758 |
| Polaromonas jejuensis | WP-068832216 |
| Polaromonas sp. AET17H-212 | WP-096671180 |
| Polaromonas sp. YR568 | WP-092127764 |
| Polaromonas sp. C04 | WP-077562980 |
| Pseudorhodobacter psychrotolerans | WP-08235149 |
| Psychrobacillus lasiicapitis | WP-142537823 |
| Psychrobacillus sp. OK032 | WP-093265425 |
| Psychrobacillus sp. OK028 | WP-093060398 |
| Psychrobacillus sp. FJAT-21963 | WP-056833301 |
| Psychrobacter jeotgali | WP-201583776 |
| Psychrobacter sp. H8-1 | WP-201574875 |
| Psychrobacter sp. Cmf 22.2 | WP-075103245 |
| Psychrobacter sp. ENNN9_III | WP-058368887 |
| Psychrobacter sp. P2G3 | WP-068327306 |
| Psychrobacter sp. P11G5 | WP-068035467 |
| Psychrosphaera haliotis | WP-155693683 |
| Shewanella psychrophila | WP-077755816 |
| Simplicispira psychrophila | WP-051603004 |
| Sphingobium psychrophilum | WP-169570392 |
| Sphingomonas psychrolutea | WP-188445826 |
| Clostridium homopropionicum | WP-074782965 |
| Clostridium sp. DL-VIII | WP-009169886 |
| Clostridium clostridioforme CAG: 132 | CDB63357 |
| Zunongwangia atlantica 221114-10F7 | ORL47196 |

Piezophilic or Piezotolerant Organisms:

| | |
|---|---|
| Oceanobacillus piezotolerans | WP-121525044 |
| Oceanobacillus profunda | WP-169713018 |
| Colwellia marinimaniae | WP-082606415 |
| Salinimonas sediminis | WP-108566897 |

*Lihuaxuella thermophila*, for instance, can survive in a relatively high temperature ranges; *Halomonas aquamarine*, for instance, can survive in a relatively high salinity ranges, and each can produce significant amounts of an enzyme for breaking down polyhydroxyalkanoate polymers. For instance, some of the characteristics of PHB depolymerase enzymes are listed in Table 4 below.

TABLE 4

| Name | #aa | #Cys | MW | pI | Accession # |
|---|---|---|---|---|---|
| PHB depolymerase (3.1.1.75) | | | | | |
| *Lihuaxuella thermophila* | 301* | 2 | 32.4 | 5.4 | WP_089972404 |
| *Halomonas aquamarina* | 332† | 8 | 35.7 | 4.4 | WP_089674669 |

*After removing 22 aa signal sequence
†After removing 24 aa signal sequence

In other aspects, for instance, the second vessel 118 enzymes were selected from *Pseudomonas fluorescens* or *Agrobacterium tumifaciens* genera. In addition, for instance, a *Pseudomonas* phasin, an accessory protein required for proper granule formation, was identified. In one aspect, for instance, the enzyme, species, and accession number are listed in Table 5 below.

TABLE 5

| Name | Species | Accession # |
|---|---|---|
| Hydroxybutyrate dehydrogenase | *A. tumifaciens* | WP_010973585 |
| Acetoacetyl-CoA synthetase | *P. fluorescens* | WP_019690949 |
| Acetoacetyl-CoA reductase | *P. aeruginosa* | WP_031690879 |
| HB polymerase | *P. fluorescens* | WP_083376742 |
| Phasin | *P. fluorescens* | WP_038445379 |

For instance, some of the characteristics of the *Pseudomonas* PHB Cycle enzymes and phasins are listed in Table 6 below.

TABLE 6

| Name | E.C. | #aa | #Cys | MW | pI |
|---|---|---|---|---|---|
| Hydroxybutyrate dehydrogenase | 1.1.1.30 | 262 | 2 | 27.8 | 5.9 |
| Acetoacetyl-CoA synthetase | 6.2.1.16 | 652 | 10 | 74.5 | 5.8 |
| Acetoacetyl-CoA reductase | 1.1.1.36 | 252 | 3 | 26.8 | 6.2 |
| HB polymerase | 2.3.1.— | 568 | 6 | 64.2 | 5.7 |
| Phasin | | 141 | 0 | 15.4 | 9.6 |

Of course, any combination of extremophiles or enzymes therefrom 102 can be utilized in disclosed methods and systems, and any combination of environmental conditions corresponding to active conditions for the enzymes can likewise be utilized to provide a multi-dimensional approach to simultaneous decontamination of a post-consumer product 104 and degradation and recycling of one or more biopolymers contained in the post-consumer product 104.

The selection of the extreme enzyme(s) and/or microorganisms from a particular environment can be selected to match the needs of a depolymerization process. For instance, if there s a need/desire to run a process at an elevated temperature then the enzyme(s) and/or microorganisms can be selected from among the thermophiles. Similarly, if there is a need or desire to run the reaction in the presence of high salt, then the enzyme(s) and/or microorganisms for use can be selected from among the halophiles. Similarly, if less extreme conditions are required for the decontamination and depolymerization process, for instance due to the known contaminants, then extremophilic enzyme(s) and/or microorganisms 102 can be selected that exhibit high activity in those less extreme conditions. In such an aspect, the decontamination process may not be required to be lethal to the pathogens, but may provide a less extreme approach to removing pathogenic characteristics from the contaminants.

In addition to microorganisms that naturally express the depolymerase gene, one or more genetically modified bacteria may also be selected that express an exogenous enzymes capable of performing specific reactions of the present invention. For example, in accordance with the present disclosure, any genus of bacterium or Archaean can be matched with any polyhydroxyalkanoate depolymerase enzyme that is expressed from a constitutive vector coupled with the correct signal sequence. In this aspect, any suitable gram positive or gram negative bacterium can be used to produce and secrete the depolymerase enzyme, which can be a gram positive polyhydroxyalkanoate depolymerase enzyme. In this manner, the microorganism product of the present disclosure can be customized based on environmental variables, the type and amount of post-consumer materials in the depository, or combinations thereof. In addition, the sequence of the enzyme can be matched to the environment by selecting one of approximately 6,400 depolymerase sequences that are known (e.g. NCBI database) or with a fully or partially engineered variant. In one aspect, the selected bacteria or archaea can be transformed with a plasmid vector which harbors a constitutively expressed gene in coding a poly[R-3-hydroxybutyrate] depolymerase that contains an appropriate N-ter signal sequence. Alternatively, the bacterium or Archaean of choice can have the depolymerase gene inserted into the bacterial chromosome by transduction, linear recombination, or any other suitable method instead of using an extra chromosomal vector thereby eliminating the need for an exogenous vector.

An enzyme can be expressed by transformation of a suitable host organism, for example, by use of either prokaryotic or eukaryotic host cells. Examples of host cell types include, without limitation, bacterial cells (e.g., *E. coli*), yeast cells (e.g., *pichia, S. cerevisiae*), cultured insect cell lines (e.g., *Drosophila*), plant cell lines (e.g., maize, tobacco, rice, sugarcane, potato tuber), mammalian cells lines (e.g., Chinese Hamster Ovary (CHO)). In one aspect, a recombinant host cell system can be selected that processes and post-translationally modifies nascent polypeptides in a manner desired to produce the final catalytic enzyme.

A nucleic acid sequence that encodes an enzyme may be placed in an expression vector for expression in the selected host. Such expression vectors can generally comprise a transcriptional initiation region linked to the nucleic acid sequence that encodes the enzyme. An expression vector can also include a plurality of restriction sites for insertion of the nucleic acid to be under the transcriptional regulation of various control elements. The expression vector additionally may contain selectable marker genes. Suitable control elements such as enhancers/promoters, splice junctions, polyadenylation signals, etc. may be placed in close proximity to the coding region to permit proper initiation of transcription and/or correct processing of the primary transcript, i.e., the coding region for the enzyme. Alternatively, the coding region utilized in an expression vector may contain endogenous enhancers/promoters, splice junctions, intervening sequences, polyadenylation signals, etc., or a combination of both endogenous and exogenous control elements.

An expression vector generally includes in the 5'-3' direction of transcription, a promoter, a transcriptional and translational initiation region, a DNA sequence that encodes the enzyme, and a transcriptional and translational termination region functional in the host cell. In one aspect, a T7-based vector can be used, which can include at least the following components: an origin of replication, a selectable antibiotic resistance gene (e.g. —amp$^r$, tetr, chlrr), a multiple cloning site, T7 initiator and terminator sequences, a ribosomal binding site, and a T7 promoter.

In general, any suitable promoter may be used that is capable of operative linkage to the heterologous DNA such that transcription of the DNA may be initiated from the promoter by an RNA polymerase that may specifically recognize, bind to, and transcribe the DNA in an open reading frame. Some useful promoters include, constitutive promoters, inducible promoters, regulated promoters, cell specific promoters, viral promoters, and synthetic promoters. Moreover, while promoters may include sequences to which an RNA polymerase binds, this is not a requirement. A promoter may be obtained from a variety of different sources. For example, a promoter may be derived entirely from a native gene of the host cell, be composed of different elements derived from different promoters found in nature, or be composed of nucleic acid sequences that are entirely synthetic. A promoter may be derived from many different types of organisms and tailored for use within a given cell. For example, a promoter may include regions to which other regulatory proteins may bind in addition to regions involved in the control of the protein translation, including coding sequences.

A translation initiation sequence can be derived from any source, e.g., any expressed *E. coli* gene. Generally, the gene is a highly expressed gene. A translation initiation sequence can be obtained via standard recombinant methods, synthetic techniques, purification techniques, or combinations thereof, which are all well known. Alternatively, translational start sequences can be obtained from numerous commercial vendors. (Operon Technologies; Life Technologies Inc.).

The termination region may be native with the transcriptional initiation region, may be native with the coding region, or may be derived from another source. Transcription termination sequences recognized by the transformed cell are regulatory regions located 3' to the translation stop codon, and thus together with the promoter flank the coding sequence. Examples include transcription termination sequences derived from genes with strong promoters, such as the trp gene in *E. coli* as well as other biosynthetic genes.

Vectors that may be used include, but are not limited to, those able to be replicated in prokaryotes and eukaryotes. For example, vectors may be used that are replicated in bacteria, yeast, insect cells, and mammalian cells. Examples of vectors include plasmids, phagemids, bacteriophages, viruses (e.g., baculovirus), cosmids, and F-factors. Specific vectors may be used for specific cells types. Additionally, shuttle vectors may be used for cloning and replication in more than one cell type. Such shuttle vectors are known in the art. The vector may, if desired, be a bi-functional expression vector that may function in multiple hosts.

An expression vector that encodes an extremophilic enzyme 102 may be introduced into a host cell by any method known to one of skill in the art and the nucleic acid constructs may be carried extrachromosomally within a host cell or may be integrated into a host cell chromosome, as desired. A vector for use in a prokaryote host, such as a bacterial cell, includes a replication system allowing it to be maintained in the host for expression or for cloning and amplification. A vector may be present in the cell in either high or low copy number. Generally, about 5 to about 200, and usually about 10 to about 150 copies of a high copy number vector are present within a host cell. A host cell containing a high copy number vector will preferably contain at least about 10, and more preferably at least about 20 plasmid vectors. Generally, about 1 to 10, and usually about 1 to 4 copies of a low copy number vector will be present in a host cell.

In many aspects, bacteria are used as host cells. Examples of bacteria include, but are not limited to, Gram-negative and Gram-positive organisms. In one aspect an *E. coli* expression system suitable for T7 protein expression may be used. Examples of T7 expression strains can include, without limitation, BL21(DE3), BL21(DE3)pLysS, BLR(DE3) pLysS, Tuner(DE3)pLysS, Tuner(DE3), Lemo21(DE3), NiCO2(DE3), Oragami2(DE3), Origami B(DE3), Shuffle T7 Expres, HMS174(DE3), HMS174(DE3)pLysS, DH5aplhaE, Rosetta2(DE3), Rosetta2(DE3)pLysS, NovaBlue(DE3), Rosetta-gami B, Rosetta-gami B(DE3), Rosetta-gami B(DE3)pLysS, Rosetta Blue (DE3), Novagen(DE3), Novagen(DE3)pLysS.

An expression vector may be introduced into bacterial cells by commonly used transformation/infection procedures. A nucleic acid construct containing an expression cassette can be integrated into the genome of a bacterial host cell through use of an integrating vector. Integrating vectors usually contain at least one sequence that is homologous to the bacterial chromosome that allows the vector to integrate. Integrating vectors may also contain bacteriophage or transposon sequences. Extrachromosomal and integrating vectors may contain selectable markers to allow for the selection of bacterial strains that have been transformed.

Useful vectors for an *E. coli* expression system may contain constitutive or inducible promoters to direct expression of either fusion or non-fusion proteins. With fusion vectors, a number of amino acids are usually added to the expressed target gene sequence. Additionally, a proteolytic cleavage site may be introduced at a site between the target recombinant protein and the fusion sequence. Once the fusion protein has been purified, the cleavage site allows the target recombinant protein to be separated from the fusion sequence. Enzymes suitable for use in cleaving the proteolytic cleavage site include TEV, Factor Xa and thrombin. Fusion expression vectors which may be useful in the present can include those which express, for example and without limitation, Maltose Binding Protein (MBP), Thioredoxin (THX), Chitin Binding Domain (CBD), Hexahistadine tag (His-tag) (SEQ ID NO: 3), glutathione-S-transferase protein (GST), FLAG peptide, N-utilization substance (NusA), or Small ubiquitin modified (SUMO) fused to the target recombinant enzyme.

Methods for introducing exogenous DNA into a host cell are available in the art, and can include the transformation of bacteria treated with $CaCl_2$ or other agents, such as divalent cations and DMSO. DNA can also be introduced into host cells by electroporation, use of a bacteriophage, ballistic transformation, calcium phosphate co-precipitation, spheroplast fusion, electroporation, treatment of the host cells with lithium acetate or by electroporation. Transformation procedures usually vary with the bacterial species to be transformed.

Following transformation or transfection of a nucleic acid into a cell, the cell may be selected for the presence of the nucleic acid through use of a selectable marker. A selectable marker is generally encoded on the nucleic acid being introduced into the recipient cell. However, co-transfection of selectable marker can also be used during introduction of nucleic acid into a host cell. Selectable markers that can be expressed in the recipient host cell may include, but are not limited to, genes that render the recipient host cell resistant to drugs such as actinomycin Cl, actinomycin D, amphotericin, ampicillin, bleomycin, carbenicillin, chloramphenicol, geneticin, gentamycin, hygromycin B, kanamycin monosulfate, methotrexate, mitomycin C, neomycin B sulfate, novobiocin sodium salt, penicillin G sodium salt, puromycin dihydrochloride, rifampicin, streptomycin sulfate, tetracycline hydrochloride, and erythromycin. Selectable markers may also include biosynthetic genes, such as those in the histidine, tryptophan, and leucine biosynthetic pathways. Upon transfection or transformation of a host cell, the cell is placed into contact with an appropriate selection agent.

When modifying a microorganism, any suitable gram positive or gram negative bacteria may be used. For example, in one aspect, the modified bacteria can be obtained from the genus *Streptomyces*. Particular examples of microorganisms from the above genus include *Streptomyces thermovulgaris, Streptomyces thermoolivaceus, Streptomyces thermohygroscopicus, Streptomyces thermocarboxydovorans*, or mixtures thereof.

The following genera may further be selected in accordance with the present disclosure to express enzymes of the present invention:

Firmicutes: *Bacillus, Lihuaxuella*, and *Clostridium*;
Proteobacteria: *Bradyrhizobium, Sphingomonas, Azotobacter, Azospirillum, Nitrobacter, Lysobacter, Stenotrophomonas, Rhizobium, Acinetobacter, Thiobacillus, Schlegelella, Janthinobacterium, Sinorhizobium, Pseudomonas, Agrobacterium*, and *Escherichia* (e.g. *Escherichia coli*);
Actinobacteria: *Rhodococcus, Arthobacter, Streptomyces, Conexibacter, Rhodococcus, Solirubrobacter, Micrococcus, Rubrobacter*, and *Actinomyces*;
Bacteroidetes: *Flavobacterium* and *Pedobacter*;
Deinococcus-thermus: *Deinococcus* and *Thermus*;
Gemmatimonadetes: *Gemmatimonas* and *Gemmatirosa*;
Spirochaetes: *Tumeriella* and *Leptospira*;
Verrucomicrobia: *Pedosphaera, Chthoniobacter*, and *Verrucomicrobia*;
Chloroflexi: *Thermogemmatispora* and *Dictyobacter*; and
Armatimonadetes: *Fimbriimonas*

It should be understood that the following list is exemplary only. The particular genera can be selected based on temperature, oxygen availability, salinity, other environmental characteristics, and the like.

The following organisms may further be selected in accordance with the present disclosure to express enzymes of the present disclosure (whether the microorganism itself or the purified enzyme): *Lysobacter aestuarii, Lysobacter antibioticus, Lysobacter bugurensis, Lysobacter capsica, Lysobacter enzymogenes, Lysobacter lacus, Lysobacter lycopersici, Lysobacter maris, Lysobacter niastensis, Lysobacter profundi, Lysobacter* sp., *Lysobacter* sp. A03, *Lysobacter* sp. cf310, *Lysobacter* sp. H21R20, *Lysobacter* sp. H21R4, *Lysobacter* sp. H23M41, *Lysobacter* sp. R19, *Lysobacter* sp. Root604, *Lysobacter* sp. Root690, *Lysobacter* sp. Root916, *Lysobacter* sp. Root983, *Lysobacter* sp. TY2-98, *Lysobacter spongiae, Lysobacter spongiicola, Lysobacter, Lysobacter alkalisoli, Lysobacter arseniciresistens, Lysobacter daejeonensis, Lysobacter dokdonensis, Lysobacter enzymogenes, Lysobacter enzymogenes, Lysobacter gilvus, Lysobacter gummosus, Lysobacter maris, Lysobacter oculi, Lysobacter panacisoli, Lysobacter penaei, Lysobacter prati, Lysobacter psychrotolerans, Lysobacter pythonis, Lysobacter ruishenii, Lysobacter segetis, Lysobacter silvestris, Lysobacter silvisoli, Lysobactersoli, Lysobacter* sp., *Lysobacter* sp. 17J7-1, *Lysobacter* sp. Alg18-2.2, *Lysobacter* sp. Cm-3-T8, *Lysobacter* sp. H23M47, *Lysobacter* sp. HDW10, *Lysobacter* sp. 114, *Lysobacter* sp. N42, *Lysobacter* sp. OAE881, *Lysobacter* sp. Root494, *Lysobacter* sp. URHA0019, *Lysobacter* sp. WF-2, *Lysobacter* sp. yr284, *Lysobacter tabacisoli, Lysobacter telluris, Lysobacter tolerans, Lysobacter tolerans, Lysobacter xinjiangensis*, unclassified *Lysobacter, Aliivibrio finisterrensis, Aliivibrio fischeri, Aliivibrio sifiae, Aliivibrio* sp., *Aliivibrio* sp. 1S128, *Aliivibrio* sp. EL58, *Aliivibrio* sp. SR45-2, *Caballeronia arvi, Caballeronia calidae, Caballeronia hypogeia, Caballeronia insecticola, Caballeronia pedi, Caballeronia terrestris, Dokdonella koreensis, Dyella caseinilytica, Dyella choica, Dyella dinghuensis, Dyella flava, Dyella jiangningensis, Dyella kyungheensis, Dyella mobilis, Dyella monticola, Dyella nitratireducens, Dyella psychrodurans, Dyella soli, Dyella solisilvae, Dyella* sp. 7MK23, *Dyella* sp. ASV21, *Dyella* sp. ASV24, *Dyella* sp. C11, *Dyella* sp. C9, *Dyella* sp. DHC06, *Dyella* sp. EPa41, *Dyella* sp. G9, *Dyella* sp. M7H15-1, *Dyella* sp. M7H15-1, *Dyella* sp. OK004, *Dyella* sp. S184, *Dyella* sp. SG562, *Dyella* sp. SG609, *Dyella* sp. YR388, *Dyella tabacisoli, Fluoribacter bozemanae, Fluoribacter dumoffii* NY 23, *Fluoribacter gormanii, Microscilla marina, Pseudomonas aeruginosa, Pseudomonas thermotolerans, Pseudomonas mediterranea, Psychrobacter* sp., *Psychromonas* sp. MB-3u-54, *Psychromonas* sp. psych-6C06, *Psychromonas* sp. RZ22, *Psychromonas* sp. Urea-02u-13, *Rhodanobacter denitrificans, Rhodanobacter fulvus, Rhodanobacter glycinis, Rhodanobacter lindaniclasticus, Rhodanobacter panaciterrae, Rhodanobacter* sp. 7MK24, *Rhodanobacter* sp. A1T4, *Rhodanobacter* sp. B04, *Rhodanobacter* sp. B05, *Rhodanobacter* sp. C01, *Rhodanobacter* sp. C03, *Rhodanobacter* sp. C05, *Rhodanobacter* sp. C06, *Rhodanobacter* sp. DHB23, *Rhodanobacter* sp. DHG33, *Rhodanobacter* sp. L36, *Rhodanobacter* sp. MP1X3, *Rhodanobacter* sp. OK091, *Rhodanobacter* sp. OR444, *Rhodanobacter* sp. PCA2, *Rhodanobacter* sp. Root480, *Rhodanobacter* sp. Root627, *Rhodanobacter* sp. Root627, *Rhodanobacter* sp. SCN 67-45, *Rhodanobacter* sp. SCN 68-63, *Rhodanobacter* sp. Soil772, *Rhodanobacter* sp. T12-5, *Rhodanobacter* sp. TND4EH1, *Rhodanobacter* sp. TND4FH1, *Rhodanobacter spathiphylli, Rhodanobacter thiooxydans, Stenotrophomonas chelatiphaga, Stenotrophomonas maltophilia, Stenotrophomonas panacihumi, Stenotrophomonas pavanii, Stenotrophomonas rhizophila, Stenotrophomonas* sp. DDT-1, *Stenotrophomonas* sp. RIT309, *Stenotrophomonas* sp. SKA14, *Vibrio aestuarianus, Vibrio antiquaries, Vibrio aquaticus, Vibrio tasmaniensis, Xanthomonadales bacterium, Xanthomonas albilineans, Xanthomonas arboricola, Xanthomonas axonopodis, Xanthomonas bromi, Xanthomonas campestris, Xanthomonas cannabis, Xanthomonas citri, Xanthomonas euvesicatoria, Xanthomonas fragariae, Xanthomonas hortorum, Xanthomonas hyacinthi, Xanthomonas oryzae, Xanthomonas phaseoli, Xanthomonas pisi, Xanthomonas sacchari, Xanthomonas* sp. Leaf131, *Xanthomonas* sp. NCPPB 1128, *Xanthomonas translucens, Xanthomonas vasicola, Xanthomonas vesicatoria*, or a combination thereof. It should be understood that the following list is exemplary only. The particular microorganism can be selected based on temperature, oxygen availability, salinity, other environmental characteristics, and the like.

For instance, in one aspect, the extremophilic microorganism 102 incorporated into the product of the present disclosure and their enzyme for producing PHB are selected from a variety of *Lysobacter* species including those listed in Table 7 below.

TABLE 7

| Organism | Accession Number |
| --- | --- |
| *Lysobacter* | WP_036193982 |
| *Lysobacter alkalisoli* | WP_141625093 |
| *Lysobacter arseniciresistens* | WP_036208009 |
| *Lysobacter daejeonensis* | WP_036135021 |
| *Lysobacter dokdonensis* | WP_036168095 |

TABLE 7-continued

| Organism | Accession Number |
|---|---|
| *Lysobacter enzymogenes* | WP_207524961 |
| *Lysobacter enzymogenes* | WP_096377760 |
| *Lysobacter enzymogenes* | WP_074869551 |
| *Lysobacter gilvus* | WP_156641946 |
| *Lysobacter gummosus* | WP_057943197 |
| *Lysobacter maris* | WP_141483002 |
| *Lysobacter oculi* | WP_112926105 |
| *Lysobacter panacisoli* | WP_200604936 |
| *Lysobacter penaei* | WP_182668477 |
| *Lysobacter prati* | WP_158731614 |
| *Lysobacter psychrotolerans* | WP_123087040 |
| *Lysobacter pythonis* | WP_122100479 |
| *Lysobacter ruishenii* | WP_144812683 |
| *Lysobacter segetis* | WP_133478701 |
| *Lysobacter silvestris* | WP_103075695 |
| *Lysobacter silvisoli* | WP_115858207 |
| *Lysobacter soli* | WP_157029884 |
| *Lysobacter* sp. | NUO78313 |
| *Lysobacter* sp. 17J7-1 | WP_133500014 |
| *Lysobacter* sp. Alg18-2.2 | WP_147890376 |
| *Lysobacter* sp. Cm-3-T8 | WP_206859118 |
| *Lysobacter* sp. H23M47 | WP_194037433 |
| *Lysobacter* sp. HDW10 | WP_166296513 |
| *Lysobacter* sp. II4 | WP_187713470 |
| *Lysobacter* sp. N42 | WP_132328958 |
| *Lysobacter* sp. OAE881 | WP_192630396 |
| *Lysobacter* sp. Root494 | WP_056131727 |
| *Lysobacter* sp. URHA0019 | WP_027083001 |
| *Lysobacter* sp. WF-2 | WP_117202823 |
| *Lysobacter* sp. yr284 | WP_091793341 |
| *Lysobacter tabacisoli* | WP_119719022 |
| *Lysobacter telluris* | WP_166211016 |
| *Lysobacter tolerans* | WP_076587639 |
| *Lysobacter tolerans* | SIP87483 |
| *Lysobacter xinjiangensis* | WP_189447436 |
| unclassified *Lysobacter* | WP_055899693 |

For instance, in one aspect, the extremophilic microorganism or enzyme therefrom 102 incorporated into the product of the present disclosure and their enzyme for metabolizing HB and producing PHB are selected from a variety of bacteria species including those listed in Table 8 below.

TABLE 8

| Organism | PHB Polymerase Ascension Number |
|---|---|
| *Aliivibrio finisterrensis* | WP_151654375 |
| *Aliivibrio fischeri* | WP_065624776 |
| *Aliivibrio sifiae* | WP_105055326 |
| *Aliivibrio* sp. | MBL4831209 |
| *Aliivibrio* sp. 1S128 | WP_065600195 |
| *Aliivibrio* sp. EL58 | WP_122034402 |
| *Aliivibrio* sp. SR45-2 | WP_182699437 |
| *Caballeronia arvi* | WP_061150199 |
| *Caballeronia calidae* | WP_062608567 |
| *Caballeronia hypogeia* | WP_061169280 |
| *Caballeronia insecticola* | BAN58336 |
| *Caballeronia pedi* | WP_061178553 |
| *Caballeronia terrestris* | WP_087660849 |
| *Dokdonella koreensis* | WP_067647850 |
| *Dyella caseinilytica* | WP_188798656 |
| *Dyella choica* | WP_126682794 |
| *Dyella dinghuensis* | WP_126672795 |
| *Dyella flava* | WP_204681682 |
| *Dyella jiangningensis* | AHX12796 |
| *Dyella kyungheensis* | WP_204634561 |
| *Dyella mobilis* | WP_204632428 |
| *Dyella monticola* | WP_115496150 |
| *Dyella nitratireducens* | WP_188792429 |
| *Dyella psychrodurans* | RDS86489 |
| *Dyella soli* | WP_131407398 |
| *Dyella solisilvae* | WP_114823339 |
| *Dyella* sp. 7MK23 | WP_192556083 |
| *Dyella* sp. ASV21 | WP_199100073 |
| *Dyella* sp. ASV24 | WP_199038667 |
| *Dyella* sp. C11 | WP_157956602 |
| *Dyella* sp. C9 | WP_114241222 |
| *Dyella* sp. DHC06 | WP_130620551 |
| *Dyella* sp. EPa41 | WP_201314821 |
| *Dyella* sp. G9 | WP_187056353 |
| *Dyella* sp. M7H15-1 | WP_164931796 |
| *Dyella* sp. M7H15-1 | QAU23859 |
| *Dyella* sp. OK004 | WP_090451505 |
| *Dyella* sp. S184 | WP_158755276 |
| *Dyella* sp. SG562 | WP_167257616 |
| *Dyella* sp. SG609 | WP_168647555 |
| *Dyella* sp. YR388 | WP_147455377 |
| *Dyella tabacisoli* | WP_114845894 |
| *Fluoribacter bozemanae* | WP_058459414 |
| *Fluoribacter dumoffii* NY 23 | KTC90057 |
| *Fluoribacter gormanii* | KTD05403 |
| *Microscilla marina* | WP_002702565 |
| *Pseudomonas aeruginosa* | AHJ25666 |
| *Pseudomonas thermotolerans* | WP_027896668 |
| *Pseudomonas mediterranea* | WP_047699726 |
| *Psychrobacter* sp. | QCF41916 |
| *Psychromonas* sp. MB-3u-54 | WP_101038601 |
| *Psychromonas* sp. psych-6C06 | WP_101107093 |
| *Psychromonas* sp. RZ22 | WP_134276148 |
| *Psychromonas* sp. Urea-02u-13 | WP_101081048 |
| *Rhodanobacter denitrificans* | NMW25143 |
| *Rhodanobacter fulvus* | WP_040670830 |
| *Rhodanobacter glycinis* | WP_140650985 |
| *Rhodanobacter lindaniclasticus* | WP_136257156 |
| *Rhodanobacter panaciterrae* | WP_189440331 |
| *Rhodanobacter* sp. 7MK24 | WP_192155134 |
| *Rhodanobacter* sp. A1T4 | WP_184673302 |
| *Rhodanobacter* sp. B04 | WP_077555812 |
| *Rhodanobacter* sp. B05 | WP_077513483 |
| *Rhodanobacter* sp. C01 | WP_077442012 |
| *Rhodanobacter* sp. C03 | WP_077518181 |
| *Rhodanobacter* sp. C05 | WP_077443954 |
| *Rhodanobacter* sp. C06 | WP_077485236 |
| *Rhodanobacter* sp. DHB23 | WP_192106892 |
| *Rhodanobacter* sp. DHG33 | WP_192163461 |
| *Rhodanobacter* sp. L36 | WP_158885070 |
| *Rhodanobacter* sp. MP 1X3 | WP_184604847 |
| *Rhodanobacter* sp. OK091 | WP_072760944 |
| *Rhodanobacter* sp. OR444 | WP_027492196 |
| *Rhodanobacter* sp. PCA2 | WP_181302403 |
| *Rhodanobacter* sp. Root480 | WP_056080179 |
| *Rhodanobacter* sp. Root627 | WP_082545971 |
| *Rhodanobacter* sp. Root627 | KRA35976 |
| *Rhodanobacter* sp. SCN 67-45 | ODT97084 |
| *Rhodanobacter* sp. SCN 68-63 | ODV10878 |
| *Rhodanobacter* sp. Soil772 | WP_056386006 |
| *Rhodanobacter* sp. T12-5 | WP_149365305 |
| *Rhodanobacter* sp. TND4EH1 | WP_099652471 |
| *Rhodanobacter* sp. TND4FH1 | WP_133950922 |
| *Rhodanobacter spathiphylli* | WP_007805234 |
| *Rhodanobacter thiooxydans* | WP_008435591 |
| *Stenotrophomonas chelatiphaga* | WP_057508611 |
| *Stenotrophomonas maltophilia* | WP_019338202 |
| *Stenotrophomonas panacihumi* | WP_057643119 |
| *Stenotrophomonas pavanii* | WP_057494653 |
| *Stenotrophomonas rhizophila* | WP_038687867 |
| *Stenotrophomonas* sp. DDT-1 | WP_061479060 |
| *Stenotrophomonas* sp. RIT309 | WP_032976188 |
| *Stenotrophomonas* sp. SKA14 | WP_008265690 |
| *Vibrio aestuarianus* | WP_168520800 |
| *Vibrio antiquarius* | WP_074190087 |
| *Vibrio aquaticus* | WP_126574305 |
| *Vibrio tasmaniensis* | WP_102248967 |
| *Xanthomonadales bacterium* | OZB58863 |
| *Xanthomonas albilineans* | WP_012916138 |
| *Xanthomonas arboricola* | WP_039511932 |
| *Xanthomonas axonopodis* | WP_042822558 |
| *Xanthomonas bromi* | PPV05022 |
| *Xanthomonas campestris* | WP_011037305 |

TABLE 8-continued

| Organism | PHB Polymerase Ascension Number |
|---|---|
| Xanthomonas cannabis | WP_047694901 |
| Xanthomonas citri | WP_046832369 |
| Xanthomonas euvesicatoria | WP_136732577 |
| Xanthomonas fragariae | WP_002802267 |
| Xanthomonas hortorum | WP_006450930 |
| Xanthomonas hyacinthi | WP_046978386 |
| Xanthomonas oryzae | WP_014503544 |
| Xanthomonas phaseoli | WP_017157553 |
| Xanthomonas pisi | WP_046964104 |
| Xanthomonas sacchari | WP_043092075 |
| Xanthomonas sp. Leaf131 | WP_055826366 |
| Xanthomonas sp. NCPPB 1128 | WP_048489717 |
| Xanthomonas translucens | WP_003466505 |
| Xanthomonas vasicola | WP_039434864 |
| Xanthomonas vesicatoria | WP_039424128 |

In one aspect, the microorganism or enzyme therefrom of the present disclosure can include a combination of different microorganisms, such as bacterium. For example, in one aspect, the product can contain one or more microorganisms that naturally secrete the depolymerase enzyme combined with one or more microorganisms that have been genetically modified in order to secrete the depolymerase enzyme. The genetically modified microorganism, for instance, can be used to fine tune the system based on environmental conditions and feed supply. Of course, in one aspect, the microorganism is a bacterium.

Particularly, in one aspect, one or more of the above microorganisms and/or their respective enzymes may be selected based upon one or more of the following factors: easy and fast to grow in high density, do not require special media, aerobic, kinetically fast, stable, tolerant to high salt temperature environment, able to produce readily purifiable enzymes, lack an unusual isoelectric point, do not require heightened biosafety measures, do not comprise Cysteine residues in excess, overall non-esoteric, and available for purchase commercially. For instance, the present disclosure has found that by limiting the amount of Cysteine residues in one aspect, improved folding may be achieved, allowing better and faster incorporation into a host, such as *E. coli* for improved production of the modified enzyme. Such a feature may be reflected in one or more of the above tables under the #Cys column, referring to the number of cysteines in the respective enzyme or coding thereof. Particularly, selection based upon one or more of the above factors can further improve the speed and efficiency of the reaction, allowing improved throughput of the industrial process.

Nonetheless, in one aspect, the microorganisms can be directly added to a post-consumer/recycled material depository prior to addition to the first vessel, added in combination with a carrier or in a suspension to the first vessel, or placed in a bioreactor as discussed above. The carrier can be a food source, or can be any suitable carrier, buffer, or the like.

In one aspect, such as when a microorganism is used, the microorganisms can be encapsulated in a carrier, such as a polymer carrier. The polymer carrier can be a material that is highly water absorbent without being water soluble. In one aspect, for instance, the polymer carrier is in the form of a gel when combined with water, can be dehydrated and converted into the form of a solid, and then capable of being rehydratable when contacted with moisture. In this manner, the one or more microorganisms can be combined with the polymer carrier in the form of a gel. Once blended together, water can then be removed in order to form a solid. The solid can be formed into any suitable shape and contacted with post-consumer product 104 waste materials. In order to degrade polymers contained in the waste material, the solid material is contacted with moisture that causes the carrier polymer to rehydrate. Once rehydrated, the microorganisms can be released from the polymer gel or can secrete enzymes that are released from the polymer gel.

Of course, as discussed above, in one aspect, the enzyme may instead be incorporated directly into the first and/or second vessel either alone, in combination with a carrier, in combination with a cofactor feed, or a combination thereof.

Nonetheless, in one aspect, for instance, the enzyme or microorganism population can be combined with a post-consumer product 104 that contains discarded incontinence products or other polymer based consumer product made from a polyhydroxyalkanoate polymer. Incontinence products include, for example, diapers, training pants, swim pants, adult incontinence products, feminine hygiene products, and the like. These products typically include a water permeable liner, an outer cover, and an absorbent structure positioned between the liquid permeable liner and the outer cover. The incontinence products may contain biopolymers in amounts greater than about 5% by weight, such as in amounts greater than about 10% by weight, such as in amounts greater than about 20% by weight, such as in amounts greater than about 30% by weight, such as in amounts greater than about 40% by weight, such as in amounts greater than about 50% by weight, such as in amounts greater than about 60% by weight, such as in amounts greater than about 70% by weight.

The amount of the microorganism product added to a post-consumer product 104 waste material depository or a bioreactor can be based on the amount of post-consumer product 104 waste materials in the depository or a bioreactor, on the amount of polyhydroxyalkanoates present in the waste material depository or a bioreactor, or based on a ratio between the encapsulated microorganism product and the amount of soil or a bioreactor present. When based on the amount of encapsulated microorganism product per incontinence product, the range can be from about 0.000001 g to about 10.0 g, such as from about 0.001 g to about 5.0 g, such as from about 0.1 g to about 1 g.

The present disclosure may be better understood with reference to the following example.

Example

The following example demonstrates some of the benefits and advantages of the present disclosure.

In one particular example, two PHB depolymerases were selected. The first was the thermophilic bacterium *Lihuaxuella thermophila*. The organism appeared to be devoid of an identifiable acetoacetyl-CoA reductase and synthetase and a HB polymerase enzyme homolog. The second HB polymerase was the halophilic bacterium *Halomonas aquamarine*. Selection of either of the organisms provided two ways of reducing the potential issues of fecal bacteria contamination, such as, for instance, in used diapers, during an industrial process. That is because fecal bacteria cannot live at elevated temperatures, for instance, 50° C. or in extremely high salt concentrations, for instance, 1.0 M. Sequence characteristics for the two polymerases are shown in Table 4.

The remaining four enzymes were selected from *Pseudomonas fluorescens* or *Agrobacterium tumifaciens*. In addition, a *Pseudomonas* phasin, an accessory protein required for proper granule formation, was identified. Accession numbers for the species and enzymes selected for inclusion are shown in Table 5. Sequence characteristics for the remaining enzymes are shown in Table 6.

Notably, only the synthetase and polymerase enzymes contain multiple cysteine residues with disulfide bonds, which can be problematic for proper folding in the *E. coli* cytoplasm during expression. Although the distribution and number of cysteine residues are typical for these enzymes across a broader phylogenetic space. Previous work has indicated that expression in the commercial *E. coli* strain Oragami2 allows for successful folding during expression.

The genus *pseudomonas* was selected as a single species expresses all the enzymes needed for the PHB Cycle, except for the dehydrogenase. Because single bacteria do not metabolize HB, PHB, or intermediates according to the PHB Cycle (FIG. 2), it was necessary to go outside a single genus (or broader taxonomy) in order to identify all the required enzymes. Including the fewest number of genera (or species) possible allowed the process conditions, such as speed, to be optimized by utilizing medium and conditions favorable to all enzymes (temperature, salts, pH, etc.). Full taxonomies for all organisms used in this example are provided in Table 7 below.

Table 7.

*Lihuaxuella thermophila*:
  Bacteria; Terrabacteria Group; Firmicutes: Bacilli; Bacillales, Thermoactinomycetaceae

*Pseudomonas depolymerans*:
  Bacteria; Proteobacteria; Gammaproteteriaeria; Pseudomonadales; Pseudomuonadacaceae

*Halomonas aquamarina*:
  Bacteria; Proteobacteria; Gammaproteobacteria; Oceanospirillales: Halomnonadaceae

*Agrobacterium tumefaciens*:
  Bacteria; Proteobacteria; Alphaproteobacteria; Rhizobiales: Rhizobiaceae; Rhizobium/Agrobacterum Group In addition to using a disulfide tolerant expression strain, protein expression was optimized by back translating the amino acid sequence of the enzyme of choice using codons that are optimized for *E. coli*. This ensured the most efficient translation, avoided pausing, and increased yields of heterologous proteins. Each protein sequence was combined with the His6 (SEQ ID NO: 3) N-terminal fusion sequence and TEV protease cleavage site, MHHHHHHLEVLFQGP (SEQ ID NO: 2), after any identified N-ter signal sequence was removed. The sequences was optimized to *E. coli* codon usage by ATUM, Inc. and cloned into the IPTG inducible vector pD454, which had a medium strength ribosomal binding site sequence and codes for ampicillin resistance. The His6 (SEQ ID NO: 3) fusion was efficiently removed from the protein with TEV protease. The work in this TL was performed with purified and cleaved enzyme. For instance, the use of a His-6 tag (SEQ ID NO: 3) greatly simplified the purification process to two steps post the formation of the lysed bacterial crude extract. The proteins expressed between 25° C. and 35° C. with a 12-hour post induction growth period and yielded between 10-20 mg of purified/cleaved enzyme per one liter of starting culture.

The bioreactor 100 prototype was composed of two distinct vessels. The first vessel (106, 108) housed the input PHB sample where the thermophilic or halophilic depolymerase reaction occurred. After the reaction was complete, as measured by a decrease in optical density at 600 nm, visually when a PHB film disappears, or when the HB assay plateaued (FIG. 5), the reaction volume was pumped through a molecular weight cutoff filter ("MWCO") 112 (MWCO; 3 kDa) for thermophilic reaction or a MWCO filter 112 and then through a Dowex ion exchange bed 114 for a halophilic reaction. The MWCO filter 112 prevented enzyme and unreacted large material to pass to the second vessel 118. The Dowex ion exchange medium removed the NaCl from the halophilic depolymerase reaction. The reaction then entered the second vessel 118 that contained the other four PHB Cycle enzymes in buffer. This second reaction was run until the optical density at 600 nm maximized. A diagram of the bioreactor 100 is shown in FIG. 1.

The reaction in the first vessel (106, 108) was efficiently conducted at 50° C. for the thermophilic reaction or at 30° C. in the case of the halophilic reaction. The input PHB 124 material was converted to HB 126 in both reactions in approximately an hour. An identical reaction to that in the first vessel (106, 108) was conducted in an open container so that timed aliquots could be removed in order to assay for the presence of HB 126. This data is shown in FIG. 3 where PHB Depolymerase (reaction 1 in FIG. 6) enzymatic activity as a function of time in the fluorometric HB assay. Reaction conditions for the thermophilic reaction: 10 mM Na-acetate pH 6.0, 5 mM KCl, 5 mM MgCl2, 50° C. Reaction conditions for the halophilic reaction: 10 mM Na-acetate pH 6.0, 5 mM KCl, 5 mM MgCl2, 1.0 M NaCl, 37° C. Closed circles: thermophilic PHD; Open circles: halophilic PHD.

The thermophilic reaction reached linear phase within 10 minutes whereas the halophilic reaction was characterized by a pronounced (~20 min) lag phase before moving into the linear portion of the reaction. Both reactions were also characterized by solution clearing during the course of the reaction, indicating that insoluble PHB was being converted to soluble HB.

The second vessel 118 reactions (FIG. 6, reactions 2-5) were conducted in the second vessel 118 buffer: 10 mM Tris-HCl (pH 7.0), 10 mM MgCl2, 1 mM KCl, 2 mM COA, 5 mM ATP, 2 mM NAD+, 5 mM NADPH. The reaction was conducted at 37° C. for a total of five hours. Every five minutes, a 100 mL aliquot was removed from the reaction and split into four subsamples. These were assayed separately for the 4 enzymatic activities that constitute the second vessel 118. Optimization of the individual reactions in this example is envisaged.

Figure 4:
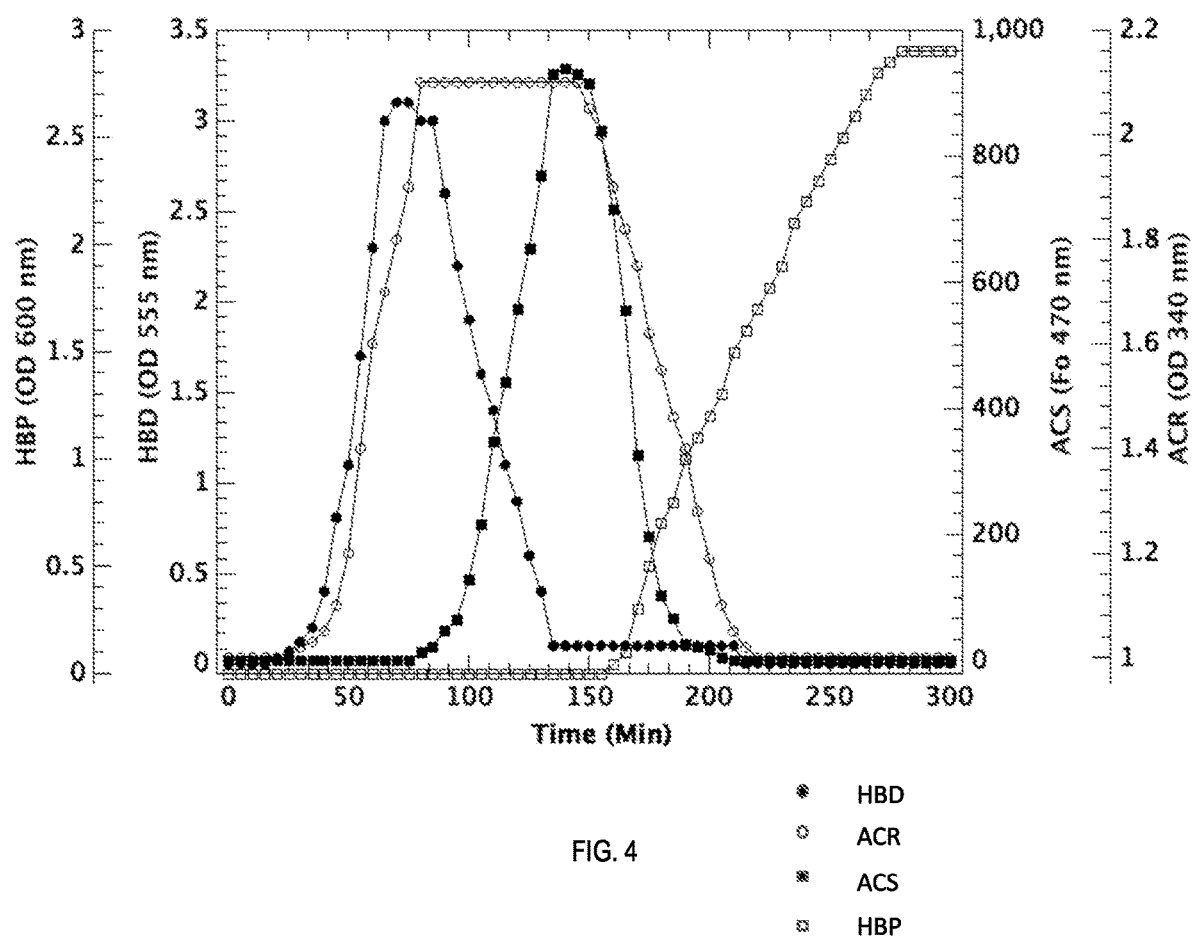
FIG. 4 is a graphical representation of the HBD and ACS reactions over time in vessel two of the bioreactor according to the Example.
Figure 5:
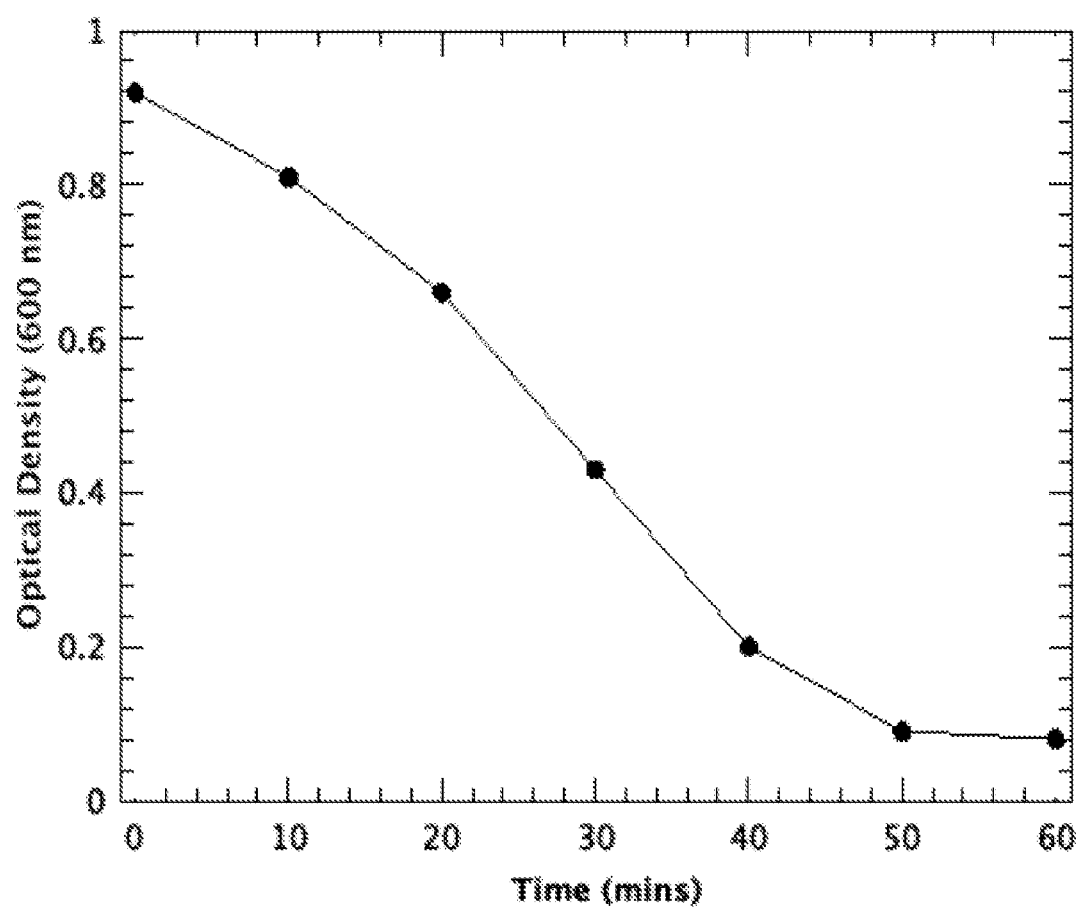
FIG. 5 is a graphical representation of the depolymerization over time of newly formed PHB by PHB depolymerase according to Example.

FIG. 4 shows the formation of PHB from the HB produced in the first vessel (106, 108) reaction. Initially the HB 126 is converted to acetoacetate 128 by the dehydrogenase (FIG. 4., closed circles). As the acetoacetate 128 is then converted (as the concentration approaches the Km of the ACS enzyme) into acetoacetyl-CoA 130 while utilizing ATP and CoA cofactors (FIG. 4., open circles). Acetoacetyl-CoA 130 is then reduced to hydroxybutyryl-CoA 132 by the reductase reaction (FIG. 6., closed squares) in the NADPH dependent portion of the overall reaction. Finally, insoluble PHB 120 is formed by the polymerase (FIG. 4., open squares). The PHB formation is accompanied by a clouding of the solution, reminiscent of the starting reaction in the first vessel (106, 108). Measuring the individual enzymatic reactions in the first vessel (106, 108) showed that the PHB Cycle was in fact operating as designed. The overall reaction started with a granulated PHB at the start of the first vessel (106, 108) reaction. As the depolymerase reaction proceeded (the thermophilic reaction in this example), the optical density at 600 nm decreases as soluble HB was formed. When the OD at 600 nm was near zero, the reaction was passed through the MWCO filter 112 and mixed with the second vessel 118 buffer. The solution become cloudy again as measured by an increase in optical density (600 nm). The precipitated material at the end of the second vessel 118 reaction was collected by centrifugation at 4,000 rpm, 10 minutes. The supernatant was removed, and the pellet was resuspended in PBS and recentrifuged. This was repeated twice. The final pellet was resuspended in the first buffer and the thermophilic depolymerase reaction was conducted as described. At 10-minute intervals, an aliquot was removed from the reaction and the optical density of the sample was measured. This result is shown in FIG. 5.

This result indicated that the material formed in the PHB Cycle reaction is indeed PHB, in that it can act as a substrate for PHB depolymerase.

In this example, different enzymes from various bacteria were tested for their applicability in the present disclosure. Bacteria that naturally produces enzymes in the present disclosure as well as bacteria that had been genetically modified to produce such enzymes were tested. The sequence of the *Pseudomonas* HB Polymerase (SEQ ID NO: 4) is as follows:

```
           10         20         30         40
    MDNNAHTFNT FWSGQVPFIA SFAVQQLPLW VSTNPWFTGQ 50         60         70         80
    EYEKWFDLPP TTLESLQAEY QTQWGLDGQR LLTGQPFSFE 90        100        110        120
    DRRFSSGNWS TPLFGSLAAF YLLNAGFLLK LLDKLPIKDK 130        140        150        160
    KPRQRLLYLV EQAIAAGAPS NFLASNPDAL QRVVDTQGGS 170        180        190        200
    LFTGLLHLAS DLQEGKMRQC DSGAFKVGVD LANTPGEVVF 210        220        230        240
    ENELFQLIQY YPQSETQYRR PVFIVPSSIN KYYILDLRPD 250        260        270        280
    NSMVPHLLQQ GHPVFLMSWP NFDQAHAGTT WDDLIDTGII 290        300        310        320
    KGLQVTREIS GEQRPNCVGF CIGSTLLSSA LAVLAAPGDK 330        340        350        360
    DIGSVSLLTT PLDYLDTGPI DIFVDEQLVA YRERTIGGQE 370        380        390        400
    GPIGLFKGED MGNTFSLLRP NDLWWNYNVD KYLKGQKPIP 410        420        430        440
    LDLLFWNNDS TNLPGPMYCW YLPHTYLQND LKSGELDCCG 450        460        470        480
    VKLNLRAIDA PAYILATHDD HIVPWRSAYA GTQLLSGTKR 490        500        510        520
    FVLGASGHIA GVINPPAREK RHYWTNNRVS KDPDTWFMNA 530        540        550        560
    QEQAGSWWND WFVWLADQAG ERQPSVSHIG NAHYPALESA

PGRYVMQ
```

The sequence of the *Pseudomonas* 3-hydroxybutyrate dehydrogenase (SEQ ID NO: 5) is as follows:

```
           10         20         30         40
    MEDQPKTVLV TGSTSGIGLA IAKRFAEAGF LVAVHGVETA 50         60         70         80
    AEGAQALEAV ATVARHRPVY FSANLAHYDE GAHLPEKVIA 90        100        110        120
    EFGHIDVLVN NAGIQKVAPI DEFDFADFSR IVAISLDSAF 130        140        150        160
    HTIHAALPGM KEPGWGRIVN IASAHGLPAS PFKAPYVATK 170        180        190        200
    HAVVGLTKSV ALEVAEGQIT CNAICPGYVW TPLVAAQVAD 210        220        230        240
    QARVHGMSED DVVKKVMLAP QPTPRFVQPE EVAEMALYLA 250        260
    GDMARSITGT TISIDGGWTA K
```

The sequence of the *Pseudomonas* Acetoacetyl-CoA synthetase (SEQ ID NO: 6) is as follows:

```
           10         20         30         40
    MSEVLWQPSA ERIGKTRMDA FRRFSNQRYN LTLADYPALH 50         60         70         80
    QWSIDQREDF WQAIIDFFEI NFHQQQSTVL PEGPQMPSAE 90        100        110        120
    NFPGATLNFA ERLLRRDDA TAVAIAIENG QRETLSYCEL 130        140        150        160
    AEHVAGLQKG LSAAGVGLGD RVAACMPNTW QTLVGMLATT 170        180        190        200
    SLGAIWSCSS PDFGTHGVVD RFGQIEPKVL ITCAGYRYAG 210        220        230        240
    KEFDQTTKVN EILERLPSLQ QLIIVPYARP QARVDEYKTQ 250        260        270        280
    ANVALWDSFY RPGGEPGFVA VPFAHPLYIL YSSGTTGVPK 290        300        310        320
    CIIHSVGGVL LQHVKEHGLH VDLGPDDRLF YYTTCQWMMW 330        340        350        360
    NWLVSALAVG SSVVLYDGSP LHPGPQRLID LIDSEAISVF 370        380        390        400
    GTSPKYLATL ESNEIQPRLS HDLSSLKALL STGSALSPQS 410        420        430        440
    YEYVYPEIKS DLCLSSMSGG TDIISCFLAG NPVLPVRRGE 450        460        470        480
    MQCKGLGMAV EVWNEAGQPV IGEKGELVCT RHFPAMPIGL 490        500        510        520
    WNDPQQEKLR ASYFSQFPGV WAQGDYAEQR PNGSWLIHGR 530        540        550        560
    SDAVLNPGGV RIGTAEIYPQ VEKVHQVLDS VAIGQQWQDD 570        580        590        600
    VRVVLFVRLP DGVTLDDNLE QQIRQVIRAN TTPRHVPAKI 610        620        630        640
    VAVTDIPRTI SGKVVELAVP NVVHGQPVKN TDALANPEAL

650
    EQFRDRPELQ R
```

The sequence of the *Pseudomonas* Acetoacetyl-CoA reductase (SEQ ID NO: 7) is as follows:

```
           10         20         30         40
    MGTASNAARI ALVTGGMGGI GTAISQRLHR DGFTVVVGCN 50         60         70         80
    PYSSRKASWI ATQLEAGFHF HCIDCDITDW DSTRQAFDMV
```

```
          90        100        110        120
HETVGPIDVL VNNAGITRDG TFRKNSPENW KAVIDTNLTG 130        140        150        160
LFNTTKQVIE GMLAKGWGRV INISSINGQR GQFGQTNYSA 170        180        190        200
AKAGIHGFSM ALAREVSGKG VTVNTVSPGY IKTDMTAAIR 210        220        230        240
PDILEDMITG IPVGRLGQPE EIASIVAWLA SDQSAYATGA

250
DFSVNGGMNM Q
```

The sequence of the *Pseudomonas* Phasin-A (SEQ ID NO: 8) is as follows:

```
          10         20         30         40
MAKVILKKKI DTQTNALSDV KIYAPKIWLA GLGAYAKVGS 50         60         70         80
EGSEYFKELV KTGQHVESKG KEVVNEQLDA ANSQTDYVKS 90        100        110        120
NVSSVKGRVE VQLDKVEKAF DARVASALNP IGIASKHDVE 130        140
TLSAKLDELT ALLERVARKH
```

The sequence of the *L. thermophila* PHB depolymerase (SEQ ID NO: 9) is as follows:

```
          10         20         30         40
MGQFIRDTAP DGPVYKLYIP SGYNGSTPLP LVVMLHGCTQ 50         60         70         80
NPDDFAAGTE MNVYAEQNNF LVAYPEQPSS ANLNKCWNWF 90        100        110        120
DSNHQSPGRG EPASIAGVVE DVKRNYSVDS RRVYAAGLSA 130        140        150        160
GGANSVIMGA TYPDVFAAIG VGSGLEYKAR TSMTSAYMAM 170        180        190        200
INGGPDPVQQ GNLAYQAMGS HARVVPVIVF HGTSDYTVYP 210        220        230        240
VNGHQVISQW AQTNDRAGDG VDNNHIDDQA DVTMNGSVPH 250        260        270        280
GRTYTRYLYR DQNGNVVMEK INVNGMGHAW SGGSTAGTYT 290        300
DPAGPEASSM MWSFFVNHPK
```

The sequence of *H. aquamarine* PHB depolymerase (SEQ ID NO: 10) is as follows:

```
          10         20         30         40
MEEEAPGLPA LGAANDQASV VGVSSGGYMA SQLAVAWPER 50         60         70         80
FSGVGMLAAG PWGCAQGALS LALNQCMMTR RGLPSLDELE 90        100        110        120
QRREPYLSLD QVGSQDASLQ LRAFVWHGDA DETVSPALGD 130        140        150        160
LLAQQWQGWL ESPEQQLRYV QPANTGHGWP VAMPKDAPID 170        180        190        200
PQSLGDCRNG GGSHVLACGE DVAGEMMAWL YPERETNASE 210        220        230        240
GELLAFDQSD FAAKGFADTG YVFVPEACEA GGCPVTVALH 250        260        270        280
GCQMNAEAID DTFVRYSGLN RWAAEHGQVV LYPQAESSMA 290        300        310        320
NPQACWDWWG FAESTWQINP LHDTRDGTQT QALMAMLDHL

330
QSATANKAAT AE
```

The production of expression vectors was as follows.

PHB Depolymerase: The amino acid sequence of the *Lihuaxuella thermophila* and the *Halomonas aquamarina* PHD enzymes were utilized to construct a recombinant DNA expression system. First, the identified signal sequence was removed from the enzyme sequences (the first 22 amino acids for the *L. thermophila* homolog and the first 24 amino acids from the *H. halomarina* homolog). A histidine expression sequence and a TEV protease cleavage signal sequence: MHHHHHHGSENLYFQG (SEQ ID NO: 1) were appended to the amino terminal portion of the enzyme sequence. Upon cleavage the recombinant proteins will have an N-ter sequence that begins with a glycine residue. This new amino acid sequence was reverse translated to DNA and codon optimized for expression in *E. coli* using the program Gene Designer from ATUM, Inc. The gene was assembled using standard PCR techniques by ATUM, Inc. and cloned into the expression vector p454-MR (ampr, medium strength ribosomal binding site). The insert was verified by DNA sequencing after construction. Expression plasmids for the second vessel 118 enzymes from *Agrobacterium* and *Pseudomonas* were constructed in a similar manner.

Expression and purification of the enzymes: Each of the expression plasmids was used to transform chemically competent Oragami2-(DE3) bacteria. Single colonies were selected from LB-Amp plates and used for expression screening. Colonies were grown at 37° C. for 12 hours in LB media supplemented with 100 □g/mL ampicillin. This culture was used to inoculate fresh LB-AMP flasks at a 1:100 inoculum. These cultures were grown at 37° C. until OD595=0.4 (typically 4 hours) at which time IPTG was added to a final concentration of 1 mM. Growth was continued for 12 hours. Cells were harvested by centrifugation at 10,000×g for 15 minutes and frozen at −80° C. until use (minimal time frozen was 24 hours). Cells were thawed on ice and were resuspended in Buffer A (0.5 M NaCl, 20 mM Tris-HCl, 5 mM imidazole, pH 7.9) (typically 1 mL per gram of cells). Cells were disrupted via two passes through a French Press followed by centrifugation at 30,000×g for 30 minutes. The crude extract was mixed with an equal volume of charged His-Bind resin slurry and the mixture was poured into 5 cm×4.9 cc column. The column was washed with 10 column volumes of was buffer (0.5 M NaCl, 20 mM Tris-HCl, 60 mM imidazole, pH 7.9) at a flow rate of 0.2 mL/min. Enzyme was eluted from the column with the addition of 3 column volumes of 0.5 M NaCl, 20 mM Tris-HCl, 1.0 M imidazole, pH 7.9. Fractions were collected (1.0 mL). Fractions containing enzyme were pooled after analysis by SDS PAGE. The pooled fractions were applied to a 70 cm×4.9 cc Sephadex G-75 column (10 mM Tris-HCl, pH 7.5, 1 mM EDTA). Fractions containing homogeneous protein were pooled (after inspection by SDS PAGE), concentrated to 5 mg/mL via Centricon filters. Enzyme was stored frozen at −20° C. until use. The histidine tag region was removed from the enzymes using TEV protease. Protein was diluted to 1.0 mg/mL into 10 mM Tris-HCl, pH 7.5, 25 mM NaCl. 100 U of TEV protease was added per mg of enzyme (approximate ratio of 1:100 (w/w). The reaction was allowed to proceed for 16 h at 4° C. The mixture was passed over a charged nickel column. One column volume of eluent was collected representing purified tag-free enzyme.

The enzymatic reaction conditions were as follows.

PHB depolymerase: A turbidimetric assay was employed to measure PHBDase activity under various conditions. The standard reaction (final volume=1.0 mL) contained 200 mg/L of PHB granules (that were previously stably suspended via sonication), 10 mM KCl, 10 mM MgCl2, 25 mM buffer at various pH values. The reaction was initiated after the addition of enzyme and monitored at 650 nm in Applied Photophysics spectropolarimeter in absorbance mode. The reaction was gently stirred with an agitator 110 and maintained at a constant temperature. OD measurements (typically starting in the range of 2-3) were converted to percent OD remaining as a function of time. Alternatively, a second assay was utilized to measure β-hydroxybutyrate directly using the Sigma-Aldrich hydroxybutyrate assay kit MAK272. HB was measured fluorometrically ($\lambda$ex=535 nm, $\lambda$em=587 nm). Aliquots (10 L) were removed from the PHB depolymerase reaction at various time points, mixed with 50 µL of the supplied HB assay buffer, and pipetted into a well of a black, flat bottomed, 96-well plate. The plate was incubated at room temperature in the dark for 30 minutes. Fluorescence emission intensity was measured using a Molecular Dynamics SpectraMax M5. Fluorescence readings were converted to HB concentration via comparison to a standard curve constructed from known concentrations of pure hydroxybutyrate. All kinetic parameters are calculated per Segel (1993).

Hydroxybutyrate dehydrogenase: The conversion of 3-hydroxybutyrate to acetoacetate 128 was monitored via an acetoacetate colorimetric assay (Sigma-Aldrich kit MAK199). At various time points during the enzyme reaction, 10 µL aliquots were removed from the reaction and chilled on ice for 5 minutes. The aliquot was then transferred into a well of a clear 96-well plate containing 90 µL of assay buffer. The plate was incubated at room temperature for 30 minutes in the dark. Optical density at 550 nm was measured using a Molecular Dynamics SpectraMax M5 spectrometer. Optical density readings were converted to acetoacetate 128 concentration via comparison to a standard curve constructed from known concentrations of pure acetoacetate. Alternatively, it is possible to simply measure the increase in optical density at 340 nm as NAD+ is converted to NADH in the course of the reaction. At various time points during the enzyme reaction, 10 L aliquots were removed from the reaction and chilled on ice for 5 minutes. The aliquot was then transferred into a well of a clear 96-well plate and optical density at 340 nm was measured using a Molecular Dynamics SpectraMax M5 spectrometer. Since the reaction stoichiometry is 1:1, the amount of NAD+ converted per unit time is equal to the amount of acetoacetate 128 formed.

Acetoacetyl-CoA synthetase: The assay measures the release of pyrophosphate (PPi) from the hydrolysis of ATP during the conversion of acetoacetate 128 to acetoacetyl-CoA 130. The High sensitivity Pyrophosphate Assay Kit from Sigma-Aldrich (MAK169) was employed. Pyrophosphate was measured fluorometrically ($\lambda$ex=370 nm, $\lambda$em=470 nm). Aliquots (10 µL) were removed from the reaction at various time points and mixed with 40 µL of the supplied assay buffer and pipetted into a well of a black, flat bottomed, 96-well plate. The plate was incubated at room temperature in the dark for 30 minutes. Fluorescence emission intensity was measured using a Molecular Dynamics SpectraMax M5. Fluorescence readings were converted to PPi concentration via comparison to a standard curve constructed from known concentrations of pure sodium pyrophosphate.

Acetoacetyl-CoA reductase: The assay measures the loss of optical density at 340 nm as NADPH is converted to NADP+. At various time points during the enzyme reaction, 10 µL aliquots were removed from the reaction and chilled on ice for 5 minutes. The aliquot was then transferred into a well of a clear 96-well plate and optical density at 340 nm was measured using a Molecular Dynamics SpectraMax M5 spectrometer. Since the reaction stoichiometry is 1:1, the amount of NADPH converted per unit time is equal to the amount of hydroxybutyryl-CoA 132 formed.

Hydroxybutyrate polymerase: A turbidimetric assay was employed to measure PHB polymerase activity. At various points in the assay, 10 µL aliquots were removed from the reaction and transferred into a well of a clear 96-well plate. Optical density was measured at 650 nm in a Molecular Dynamics SpectraMax M5 spectrometer.

Those of ordinary skill in the art will appreciate that an agitator 110 may be used to allow for stirring or mixing of any such reactions in the first vessel (106, 108) and/or the second vessel 118 of the bioreactor 100 and that a filter, a valve, or any such other precipitate collection-related device (122) may be utilized to collect newly formed PHB 120.

Bioreactor: A prototype bioreactor 100 was constructed utilizing 20 mL syringes, a chromatography column, and tubing. Everything was connected with Luer locks. The syringes served in lieu of pumps to move the reaction fluid from the first vessel (106, 108), through the chelation resin, and into the second reaction vessel. The first syringe contained a 200 mg PHB film or 200 mg/mL granulated PHB. The syringe was immersed in a water bath at the reaction temperature for the duration of the reaction (typically 2 hours). The plungers of both syringes were moved such that the reaction transferred from syringe 1, through the central column (that contained a MWCO filter 112 (3 kDa) and/or Dowex ion exchange resin) 114, and into syringe 2 which was preloaded with the second vessel 118 enzymes in the reaction buffer: 10 mM Tris-HCl (pH 7.0), 10 mM MgCl2, 2.0 mM ATP, 2.0 mM Coenzyme-A, 2 mM NAD+, 2.0 mM NADPH. All enzymes were added at 2.0 mM final concentration. The second vessel 118 reaction was run at 40° C. for 5 minutes. At various timepoints during the overall reaction, 100 mL aliquots were removed, split into 25 mL samples and assayed separately for the four enzyme activities that constitute the total second vessel 118 reaction.

This exemplifies a metabolic pathway that can depolymerize a PHB film or granule, convert the resulting hydroxybutyrate 126, in three steps, to hydroxybutyryl-CoA 132, and in turn polymerize that into PHB. Hence this work represents the first ever possibility that PHB can be a truly circular solution for the replacement of polypropylene.

These and other modifications and variations to the present invention may be practiced by those of ordinary skill in the art, without departing from the spirit and scope of the present invention, which is more particularly set forth in the appended claims. In addition, it should be understood that facets of the various aspects may be interchanged both in whole or in part. Furthermore, those of ordinary skill in the art will appreciate that the foregoing description is by way of example only, and is not intended to limit the invention so further described in such appended claims.

What is claimed is:

1. A process for recycling biopolymers in polyhydroxyalkanoate family from a polyhydroxyalkanoate-containing post-consumer product comprising:

within a first vessel, contacting a post-consumer product with an extremophilic microorganism suspension or an extremophilic depolymerase enzyme to supply a hydroxyalkanoate monomer, wherein the extremophilic depolymerase enzyme comprises 12 or less Cysteine residues, and wherein the extremophilic microorganism is either *Lihuaxuella thermophila* or *Halomonas aquamarine*;

pumping the monomer through a filter to a second bioreactor vessel; and within the second vessel, contacting the monomer with an enzyme, producing a recycled polyhydroxyalkanoate.

2. The process of claim 1, wherein the polyhydroxyalkanoate is polyhydroxybutyrate.

3. The process of claim 1, wherein the extremophilic depolymerase enzyme is obtained from a bacteria of the genera: *Halomonas, Lihuaxuella, Lysobacter, Alteromonas, Arthrobacter, Azospirillum, Empedobacter, Desulfovibrio, Halobacillus, Halobacteriovorax, Haloechinothrix, Halomarina, Halorussus, Haloterrigena, Isoptericola, Marinobacter, Methyloligella, Micromonospora, Natronococcus, Nocardiopsis, Paracoccus, Roseivivax, Saccharomonospora, Shewanella, Alicyclobacillus, Natranaerobius, Halobacteriaceae, Hyphomonas, Amycolatopsis, Georgenia, Acidothermus, Thermobifida*, or a combination thereof.

4. The process of claim 1, wherein the extremophilic microorganism or extremophilic depolymerase enzyme is either salt tolerant from about 0.5 molar to about 5 molar or temperature tolerant from about 40° C. to about 120° C., or a combination thereof.

5. The process of claim 1, wherein the extremophilic depolymerase enzyme is produced by a genetically modified microorganism that has been genetically modified to secrete the extremophilic depolymerase enzyme.

6. The process of claim 1, wherein the extremophilic depolymerase enzyme is produced by at least one type of a naturally occurring microorganism that naturally encodes the extremophilic depolymerase enzyme.

7. The process of claim 1, wherein the extremophilic depolymerase enzyme is purified from: *Lysobacter aestuarii, Lysobacter antibioticus, Lysobacter bugurensis, Lysobacter capsica, Lysobacter enzymogenes, Lysobacter lacus, Lysobacter lycopersici, Lysobacter maris, Lysobacter niastensis, Lysobacter profundi, Lysobacter* sp., *Lysobacter* sp. A03, *Lysobacter* sp. cf310, *Lysobacter* sp. H21R20, *Lysobacter* sp. H21R4, *Lysobacter* sp. H23M41, *Lysobacter* sp. R19, *Lysobacter* sp. Root604, *Lysobacter* sp. Root690, *Lysobacter* sp. Root916, *Lysobacter* sp. Root983, *Lysobacter* sp. TY2-98, *Lysobacter spongiae, Lysobacter spongiicola, Lysobacter, Lysobacter alkalisoli, Lysobacter arseniciresistens, Lysobacter daejeonensis, Lysobacter dokdonensis, Lysobacter enzymogenes, Lysobacter enzymogenes, Lysobacter gilvus, Lysobacter gummosus, Lysobacter maris, Lysobacter oculi, Lysobacter panacisoli, Lysobacter penaei, Lysobacter prati, Lysobacter psychrotolerans, Lysobacter pythonis, Lysobacter ruishenii, Lysobacter segetis, Lysobacter silvestris, Lysobacter silvisoli, Lysobacter soli, Lysobacter* sp., *Lysobacter* sp. 17J7-1, *Lysobacter* sp. Alg18-2.2, *Lysobacter* sp. Cm-3-T8, *Lysobacter* sp. H23M47, *Lysobacter* sp. HDW10, *Lysobacter* sp. II4, *Lysobacter* sp. N42, *Lysobacter* sp. OAE881, *Lysobacter* sp. Root494, *Lysobacter* sp. URHA0019, *Lysobacter* sp. WF-2, *Lysobacter* sp. yr 284, *Lysobacter tabacisoli, Lysobacter telluris, Lysobacter tolerans, Lysobacter tolerans, Lysobacter xinjiangensis*, unclassified *Lysobacter, Aliivibrio finisterrensis, Aliivibrio fischeri, Aliivibrio sifiae, Aliivibrio* sp., *Aliivibrio* sp. 1S128, *Aliivibrio* sp. EL58, *Aliivibrio* sp. SR45-2, *Caballeronia arvi, Caballeronia calidae, Caballeronia hypogeia, Caballeronia insecticola, Caballeronia pedi, Caballeronia terrestris, Dokdonella koreensis, Dyella caseinilytica, Dyella choica, Dyella dinghuensis, Dyella flava, Dyella jiangningensis, Dyella kyungheensis, Dyella mobilis, Dyella monticola, Dyella nitratireducens, Dyella psychrodurans, Dyella soli, Dyella solisilvae, Dyella* sp. 7MK23, *Dyella* sp. ASV21, *Dyella* sp. ASV24, *Dyella* sp. C11, *Dyella* sp. C9, *Dyella* sp. DHC06, *Dyella* sp. EPa41, *Dyella* sp. G9, *Dyella* sp. M7H15-1, *Dyella* sp. M7H15-1,

*Dyella* sp. OK004, *Dyella* sp. S184, *Dyella* sp. SG562, *Dyella* sp. SG609, *Dyella* sp. YR388, *Dyella tabacisoli, Fluoribacter bozemanae, Fluoribacter dumoffii* NY 23, *Fluoribacter gormanii, Microscilla marina, Pseudomonas aeruginosa, Pseudomonas thermotolerans, Pseudomonas mediterranea, Psychrobacter* sp., *Psychromonas* sp. MB-3u-54, *Psychromonas* sp. psych-6C06, *Psychromonas* sp. RZ22, *Psychromonas* sp. Urea-02u-13, *Rhodanobacter denitrificans, Rhodanobacter fulvus, Rhodanobacter glycinis, Rhodanobacter lindaniclasticus, Rhodanobacter panaciterrae, Rhodanobacter* sp. 7MK24, *Rhodanobacter* sp. A1T4, *Rhodanobacter* sp. B04, *Rhodanobacter* sp. B05, *Rhodanobacter* sp. C01, *Rhodanobacter* sp. C03, *Rhodanobacter* sp. C05, *Rhodanobacter* sp. C06, *Rhodanobacter* sp. DHB23, *Rhodanobacter* sp. DHG33, *Rhodanobacter* sp. L36, *Rhodanobacter* sp. MP 1X3, *Rhodanobacter* sp. OK091, *Rhodanobacter* sp. OR444, *Rhodanobacter* sp. PCA2, *Rhodanobacter* sp. Root480, *Rhodanobacter* sp. Root627, *Rhodanobacter* sp. Root627, *Rhodanobacter* sp. SCN 67-45, *Rhodanobacter* sp. SCN 68-63, *Rhodanobacter* sp. Soil772, *Rhodanobacter* sp. T12-5, *Rhodanobacter* sp. TND4EH1, *Rhodanobacter* sp. TND4FH1, *Rhodanobacter spathiphylli, Rhodanobacter thiooxydans, Stenotrophomonas chelatiphaga, Stenotrophomonas maltophilia, Stenotrophomonas panacihumi, Stenotrophomonas pavanii, Stenotrophomonas rhizophila, Stenotrophomonas* sp. DDT-1, *Stenotrophomonas* sp. RIT309, *Stenotrophomonas* sp. SKA14, *Vibrio aestuarianus, Vibrio antiquaries, Vibrio aquaticus, Vibrio tasmaniensis, Xanthomonadales bacterium, Xanthomonas albilineans, Xanthomonas arboricola, Xanthomonas axonopodis, Xanthomonas bromi, Xanthomonas campestris, Xanthomonas cannabis, Xanthomonas citri, Xanthomonas euvesicatoria, Xanthomonas fragariae, Xanthomonas hortorum, Xanthomonas hyacinthi, Xanthomonas oryzae, Xanthomonas phaseoli, Xanthomonas pisi, Xanthomonas sacchari, Xanthomonas* sp. Leaf131, *Xanthomonas* sp. NCPPB 1128, *Xanthomonas translucens, Xanthomonas vasicola, Xanthomonas vesicatoria*, or a combination thereof.

8. The process of claim 1, wherein the extremophilic depolymerase enzyme is purified from *Pseudomonas fluorescens* or *Agrobacterium tumefaciens*.

9. The process of claim 1, wherein the extremophilic depolymerase enzyme or the enzyme producing the recycled polyhydroxyalkanoate comprises 10 or less Cysteine residues.

10. The process of claim 1, wherein the extremophilic depolymerase enzyme has a molecular weight of about 3 kDa or less.

11. The process of claim 1, wherein the filter is a molecular weight cutoff filter of about 3 kDa to about 30 kDa, optionally followed by an ion exchange bed.

12. The process of claim 1, wherein the pumping through the filter of the hydroxyalkanoate monomer to the second bioreactor vessel occurs when a measured optical density at 600 nm of the first bioreactor vessel contents is about less than 0.4 or when at least 40% of polyhydroxyalkanoate in the post-consumer product has been depolymerized to the monomer, or a combination thereof.

13. The process of claim 1, wherein the post-consumer product may contain urine, menses, feces, or a combination thereof or is selected from the group comprising incontinence products, baby and childcare products, feminine care products, and family care products, or a combination thereof.

14. A process for recycling biopolymers in polyhydroxyalkanoate family from a polyhydroxyalkanoate-containing post-consumer product comprising:
  within a first vessel, contacting a post-consumer product with an extremophilic microorganism suspension or an extremophilic depolymerase enzyme to supply a hydroxyalkanoate monomer, wherein the extremophilic microorganism or the extremophilic depolymerase enzyme is either *Lihuaxuella thermophila* or *Halomonas aquamarine* or purified therefrom;
  pumping the monomer through a filter to a second bioreactor vessel; and
  within the second vessel, contacting the monomer with an enzyme, producing a recycled polyhydroxyalkanoate.

\* \* \* \* \*